(12) United States Patent
Durairaj et al.

(10) Patent No.: US 7,705,088 B2
(45) Date of Patent: Apr. 27, 2010

(54) RESORCINOL-BLOCKED ISOCYANATE COMPOSITIONS AND THEIR APPLICATIONS

(75) Inventors: Raj B. Durairaj, Monroeville, PA (US); Gary A. Jesionowski, Pittsburgh, PA (US); Mark A. Lawrence, Murrysville, PA (US)

(73) Assignee: INDSPEC Chemical Corporation, Pittsburgh, PA (US)

( * ) Notice: Subject to any disclaimer, the term of this patent is extended or adjusted under 35 U.S.C. 154(b) by 661 days.

(21) Appl. No.: 11/564,686

(22) Filed: Nov. 29, 2006

(65) Prior Publication Data

US 2007/0205393 A1  Sep. 6, 2007

Related U.S. Application Data

(60) Provisional application No. 60/779,343, filed on Mar. 3, 2006.

(51) Int. Cl.
*C08G 18/08* (2006.01)
(52) U.S. Cl. .................................... 524/589
(58) Field of Classification Search ............. 524/589
See application file for complete search history.

(56) References Cited

U.S. PATENT DOCUMENTS

| | | | |
|---|---|---|---|
| 2,994,671 A | 8/1961 | Thompson | |
| 3,226,276 A | 12/1965 | Rye et al. | |
| 3,268,467 A | 8/1966 | Rye et al. | |
| 3,307,966 A | 3/1967 | Snoaf | |
| 3,431,241 A | 3/1969 | Moult et al. | |
| 3,433,768 A | 3/1969 | Muhlberher et al. | |
| 3,933,677 A | 1/1976 | Aufdermarsh, Jr. | |
| 3,997,592 A | 12/1976 | Aufdermarsh, Jr. | |
| 4,031,288 A | 6/1977 | Bhakuni et al. | |
| 4,344,892 A | 8/1982 | Sanns, Jr. | |
| 4,396,647 A | 8/1983 | Linden | |
| 4,444,845 A | 4/1984 | Dunwald | |
| 5,296,160 A | 3/1994 | Tirpak et al. | |
| 5,470,945 A | 11/1995 | Markle et al. | |
| 5,624,765 A | 4/1997 | Toukairin et al. | |
| 5,889,125 A | 3/1999 | Neumann et al. | |
| 6,051,674 A | 4/2000 | Yezrielev et al. | |
| 2002/0122938 A1 | 9/2002 | Fisher | |
| 2003/0232915 A1 | 12/2003 | Corvasce et al. | |
| 2005/0165192 A1 | 7/2005 | Rosen et al. | |

FOREIGN PATENT DOCUMENTS

| | | |
|---|---|---|
| EP | 1 371 680 A1 | 12/2003 |
| EP | 1 529 827 A1 | 5/2005 |
| GB | 1 349 740 | 4/1974 |

OTHER PUBLICATIONS

Zeno W. Wicks, Blocked Isocyanates, Progress in Organic Coatings, vol. 3 (1975), 73-99, Elsevier Sequoia S.A., Lausanne, Netherlands.
Notification of Transmittal of the International Search report and the Written Opinion of the International Searching Authority for PCT/US2006/061348, mailed on Jun. 4, 2007.
International Search Report for PCT/US2006/061348, mailed on Jun. 4, 2007.
Written Opinion of the International Searching Authority for PCT/US2006/061348, mailed on Jun. 4, 2007.

*Primary Examiner*—Edward J Cain

(57) ABSTRACT

Resorcinol-blocked isocyanate compositions are derived from the reaction between a resorcinol compound and at least two different isocyanate compounds. The resorcinol-blocked isocyanate compositions may have two or more unblocking temperatures and/or melting characteristics that may provide some unique properties, such as improved adhesion of rubber reinforcing materials to rubber materials or compounds. The resorcinol-blocked isocyanate compositions can be used in fabric dipping formulations and/or rubber compositions with improved properties.

58 Claims, 1 Drawing Sheet

RESORCINOL-BLOCKED ISOCYANATE COMPOSITIONS AND THEIR APPLICATIONS

PRIOR RELATED APPLICATIONS

This application claims priority to U.S. Provisional Application No. 60/779,343, filed Mar. 3, 2006. For purposes of United States patent practice, the contents of the provisional application are herein incorporated by reference in their entirety.

FEDERALLY SPONSORED RESEARCH STATEMENT

Not applicable.

REFERENCE TO MICROFICHE APPENDIX

Not applicable.

FIELD OF THE INVENTION

This invention relates to resorcinol-blocked isocyanate compositions comprising at least a reaction product derived from the reaction between a resorcinol compound and at least two different isocyanate compounds, methods for their synthesis and applications thereof, particularly their applications in rubber compound formulations and fabric dipping formulations for treating fibers, filaments, fabrics or cords to enhance their adhesion to rubber compounds.

BACKGROUND OF THE INVENTION

Resorcinol compounds have been widely used in various applications including rubber compounding and fabric dipping technologies. In rubber compound formulations, resorcinol resins have been widely used as methylene acceptors. Although the resorcinol resins generally provide sufficient adhesion properties, it is still desirable to improve the dynamic properties, such as storage modulus and tangent delta, of the rubber compounds by using novel resorcinol compounds.

The dipping technology has been extensively used throughout the rubber and tire industries to enhance the adhesion of rubber reinforcing materials such as fibers, filaments, fabrics or cords of polyesters (such as polyethylene terephthalate (PET) and polyethylene naphthalate (PEN)), polyamides (such as nylons and aramids), carbon or polybenzoxazole (PBO) to natural as well as synthetic rubbers. For improving the adhesion of rubbers to fibers of polyesters or polyamides, numerous modifications have been made in the dipping formulations. Among these modifications, the addition of blocked aromatic diisocyanates appeared to enhance the adhesion of PET to rubbers. In general, blocked diisocyanates, particularly the caprolactam- and phenol-blocked diisocyanate have been widely used by the rubber and tire industries. Some common examples of caprolactam- and phenol-blocked diisocyanates are caprolactam- and phenol-blocked 4,4'-diphenylmethane diisocyanate (4,4'-MDI).

The use of phenol-blocked diisocyanates such as phenol-blocked 4,4'-MDI have been restricted in dipping formulations, possibly due to their high unblocking temperatures. Further, under the process temperature of the fabric-treating technology, which generally is between 150° C. and 240° C., the unblocking reaction produces phenol from the phenol-blocked aromatic diisocyanates and thus may pose toxic and hazardous problems. Further, the liberated phenol may remain unreacted and produce a possibly corrosive phenolic environment in the fabric treater and other equipment.

Caprolactam-blocked diisocyanates, such as caprolactam-blocked 4,4'-MDI (e.g., GRILBOND® IL-6 from EMS-Primid), have been extensively used as ingredients in dipping formulations for isocyanate treatment of rubber reinforcing materials without a resorcinol-formaldehyde-latex (RFL); or as dip additives in other dipping formulations such as the single- and double-step RFL dipping formulations for treating rubber reinforcing materials. Like phenol-blocked 4,4'-MDI, the caprolactam-blocked 4,4'-MDI generally has a high unblocking temperature. In some instances, the adhesion of PET cords to rubber compounds may be enhanced by blending the phenol- and caprolactam-blocked 4,4'-MDIs together and using in RFL formulations.

In addition to phenol- and caprolactam-blocked diisocyanates, resorcinol-blocked diisocyanates such as 4,4'-MDI can be used in fabric dipping formulations. The resorcinol-blocked diisocyanates may provide some unique characteristics as an ingredient or additive in the dipping formulations. For example, the resorcinol liberated from the unblocking reaction of a resorcinol-blocked diisocyanate is more reactive than most other blocking agents, such as phenol or caprolactam. Therefore, resorcinol-blocked diisocyanate provides additional reactive resorcinol which is the major reactive component in the RFL-type formulations. Further, resorcinol-blocked diisocyanates have terminal phenolic hydroxyl groups which can promote the reaction between the resorcinol-blocked diisocyanates and epoxy compounds present in dipping formulations.

Although some of the problems associated with the use of phenol-blocked or caprolactam-blocked isocyanates in dipping formulations can be overcome by the use of resorcinol-blocked diisocyanates, all current blocked diisocyanates have the same characteristic of having only one unblocking temperature and/or one melting characteristic. However, in some high performance applications, it may be desirable to use a blocked diisocyanate having two or more unblocking temperatures and/or melting characteristics that may provide some unique properties, such as improved adhesion of various synthetic fiber materials to rubber compounds.

SUMMARY OF THE INVENTION

Disclosed herein are resorcinol-blocked isocyanate compositions that have unique properties, such as improved adhesion of rubber reinforcing materials to rubber materials or compounds. In one aspect, disclosed herein are resorcinol-blocked isocyanate compositions comprising:

(a) a first compound having Formula (IIA):

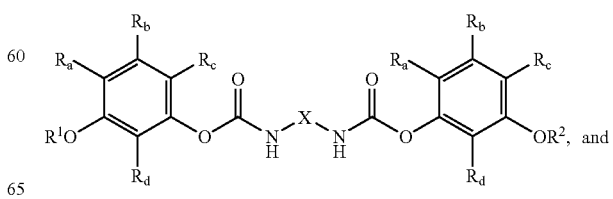

(b) a second compound having Formula (IIIA):

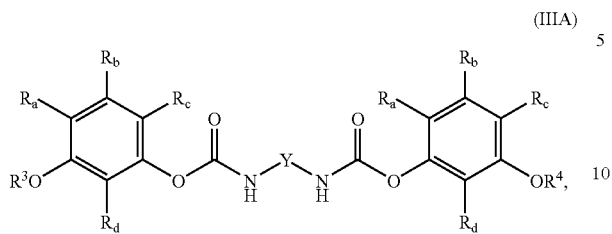
(IIIA)

wherein X and Y are different and each of X and Y is or comprises independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

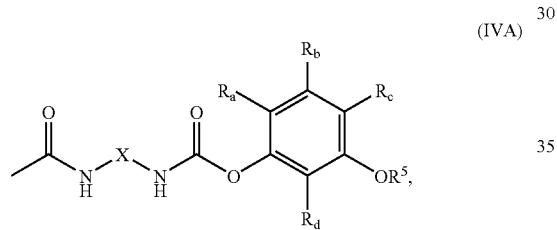
(IVA)

-continued

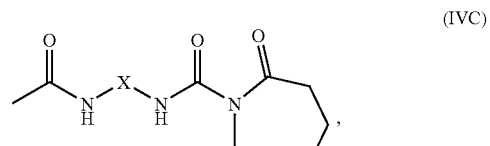
(IVB)

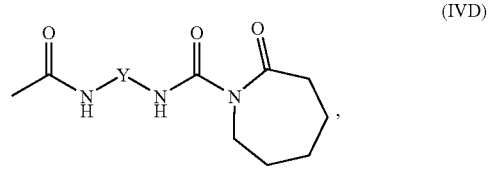
(IVC)

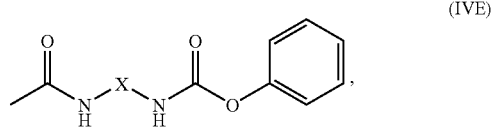
(IVD)

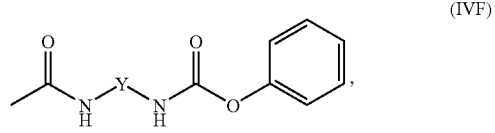
(IVE)

(IVF)

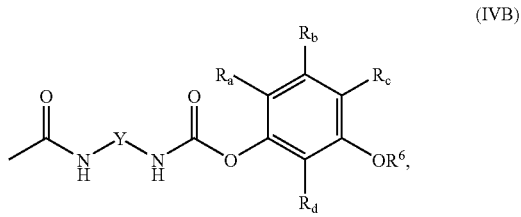

wherein each of $R^5$ and $R^6$ is independently H, acrylate, methacrylate, silyl ether, siloxanyl, aryl, aralkyl, acyl, alkyl or alkenyl.

In one embodiment, the resorcinol-blocked isocyanate composition further comprises a third compound having Formula (IIB):

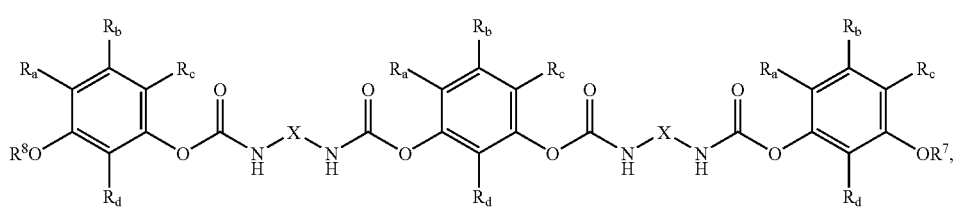
(IIB)

wherein X is or comprises alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^7$ and $R^8$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF), with the proviso that Formula (IIA), Formula (IIB) and Formula (IIIA) are different from each other.

In a further embodiment, the resorcinol-blocked isocyanate composition further comprises a fourth compound having Formula (IIIB):

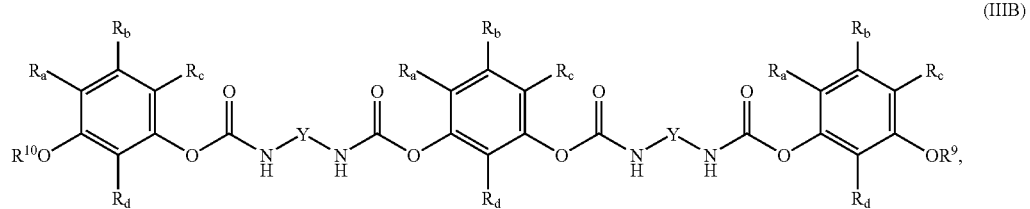

(IIIB)

wherein Y is or comprises alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^9$ and $R^{10}$ is independently H, acrylate, methacrylate, silyl ether, siloxanyl, aryl, aralkyl, acyl, alkyl, alkenyl, Formula (IVA) or Formula (IVB), with the proviso that Formula (IIA), Formula (IIB), Formula (IIIA) and Formula (IIIB) are different from each other.

In a further embodiment, the resorcinol-blocked isocyanate composition further comprises a fifth compound having Formula (IIC):

wherein X and Y are as defined above; each of $R_a$, $R_b$, $R_c$ and $R_d$ is independently hydrogen, hydroxyl, halide, nitro, benzo, carboxy, acrylate, methacrylate, silyl ether, siloxanyl, aryl, acyl, alkyl, aryl, aralkyl, or alkaryl; and each of $R^{11}$ and $R^{12}$ is independently H, acrylate, methacrylate, silyl ether, siloxanyl, aryl, aralkyl, acyl, alkyl, alkenyl, Formula (IVA) or Formula (IVB), with the proviso that Formula (IIA), Formula (IIB), Formula (IIC), Formula (IIIA) and Formula (IIIB) are different from each other.

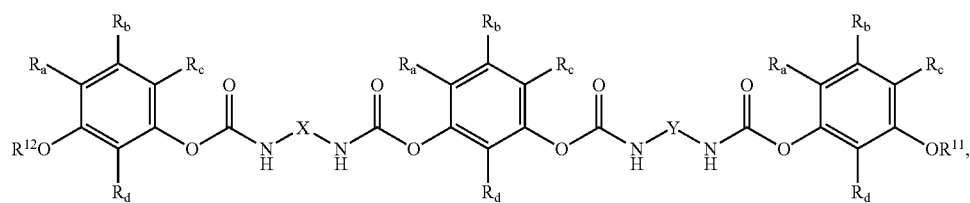

(IIC)

In a further embodiment, the resorcinol-blocked isocyanate composition comprises Compounds (1)-(5) having the formulae:

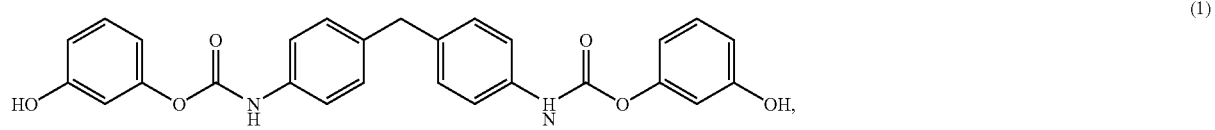

(1)

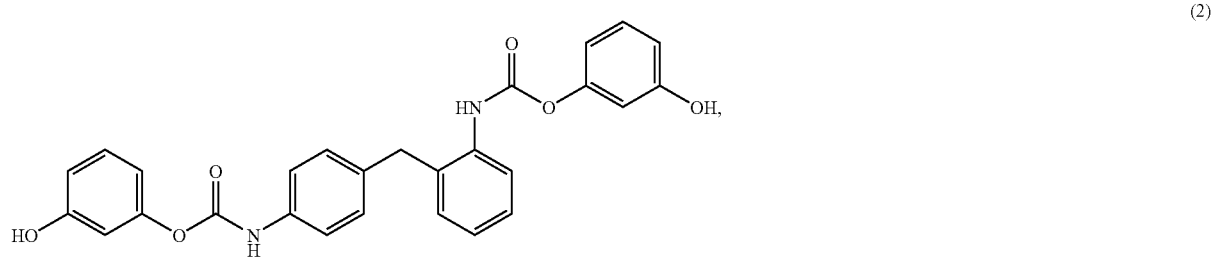

(2)

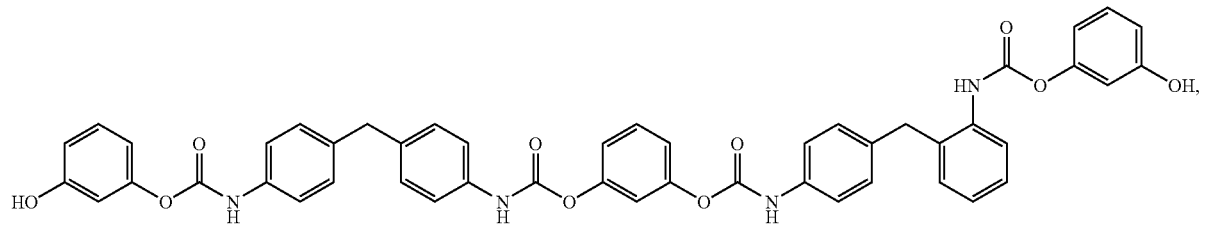
(3)

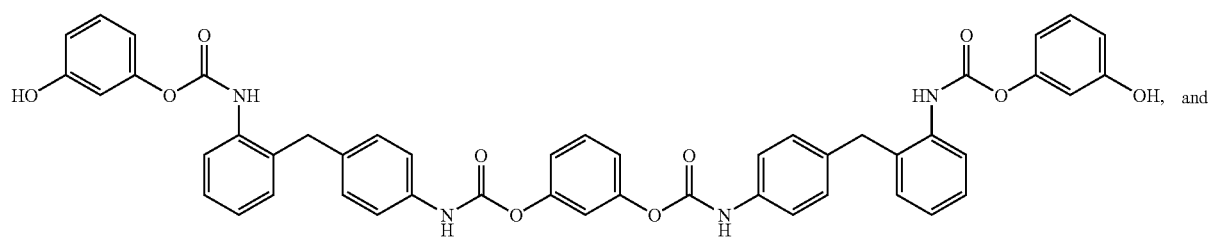
(4)

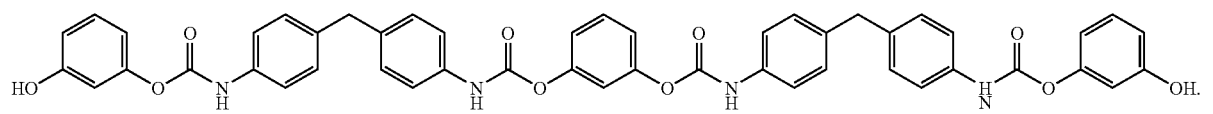
(5)

In a further embodiment, each of Compounds (1)-(5) is optionally substituted.

In a further embodiment, the resorcinol-blocked isocyanate composition has at least two melting temperatures or at least two unblocking temperatures.

In a further embodiment, the mole ratio of Formula (IIA) to Formula (IIIA) is from about 10:90 to about 90:10 or from about 35:65 to about 65:35.

In another aspect, disclosed herein are processes for preparing resorcinol-blocked isocyanate compositions comprising reacting at least two different isocyanate compounds with a resorcinol compound of Formula (I):

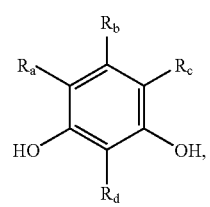
(I)

wherein each of $R_a$, $R_b$, $R_c$, and $R_d$ is independently hydrogen, hydroxyl, halide, nitro, benzo, carboxy, acyl, alkyl, aryl, aralkyl, or alkaryl.

In one embodiment, the reaction of the process occurs in the absence of a solvent.

In a further embodiment, the reaction occurs in the presence of a catalyst which may be 3-methyl-1-phenyl-2-phospholene-1-oxide or dibutyltin dilaurate.

In a further embodiment, the resorcinol compound in the process is resorcinol.

In a further embodiment, the at least two isocyanate compounds in the process have the formulae O═C═N—X—N═C═O and O═C═N—Y—N═C═O wherein X and Y are as defined above.

In a further embodiment, each of X and Y of the at least two isocyanate compounds and Formulae (IIA), (IIB), (IIC), (IIIA), (IIIB), (IVA), (IVB), (IVC), (IVD), (IVE) and (IVF) is independently a divalent radical having one of the following formulae:

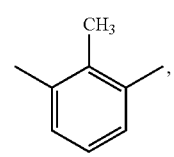
(A)

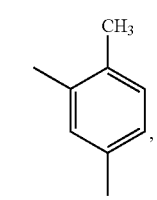
(B)

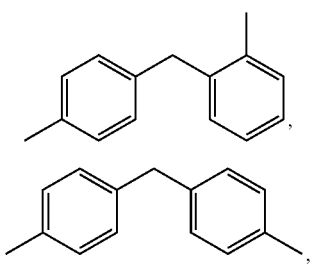
(C)

(D)

-continued (E) 

(F) 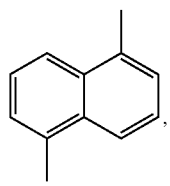

(G) 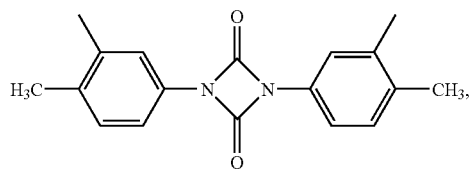

(H) 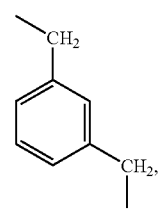

(I) 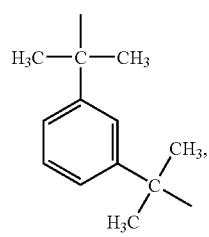

(J) 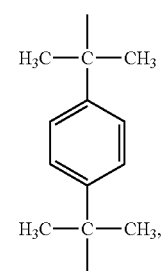

(K) 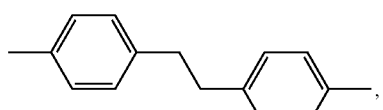

(L) 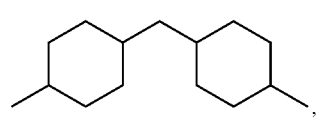

(M) 

(N) 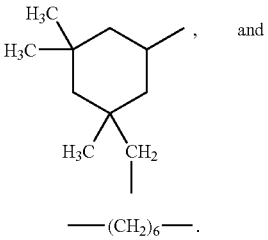 and (O) —(CH$_2$)$_6$—.

In a further embodiment, the reaction temperature of the process is above the melting point of the resorcinol compound.

In a further embodiment, at least a portion of the resorcinol compound of Formula (I) in the process is replaced with a different blocking agent which may be caprolactam, a phenol compound or a combination thereof; wherein the phenol compound may have Formula (IA):

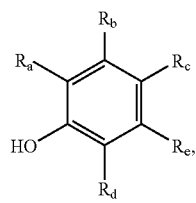

(IA)

wherein each of $R_a$, $R_b$, $R_c$, $R_d$ and $R_e$ of the phenol compound of Formula (IA) is independently hydrogen, halide, nitro, benzo, carboxy, acrylate, methacrylate, silyl ether, siloxanyl, acyl, alkyl, aryl, aralkyl, or alkaryl.

In another aspect, disclosed herein are vulcanizable rubber compositions comprising a rubber material, a methylene donor and a methylene acceptor comprising the resorcinol-blocked isocyanate composition comprising Formula (IIA), (IIB), (IIC), (IIIA), (IIIB), or a combination thereof. In one embodiment, the resorcinol-blocked isocyanate composition comprises Formula (IIA) and (IIIA).

In a further embodiment, the rubber material in the vulcanizable rubber composition is a natural or synthetic rubber.

In a further embodiment, the vulcanizable rubber composition further comprises a rubber reinforcement material which may be in the form of fibers, filaments, fabrics or cords.

In a further embodiment, the rubber reinforcing material may be made of a polyester, a polyamide, carbon, glass, steel, polybenzoxazole or rayon. In a further embodiment, the reinforcing material is steel.

In a further embodiment, the vulcanizable rubber composition further comprises a vulcanizing agent.

In a further embodiment, the vulcanizable rubber composition further comprises at least an additive, wherein the additive is carbon black, zinc oxide, silica, an antioxidant, a stearate, an accelerator, an adhesion promoter, a cobalt salt, stearic acid, a filler, a plasticizer, a wax, a processing oil, a retarder, an antiozonant or a combination thereof.

In another aspect, disclosed herein are dipping formulations comprising the resorcinol-blocked isocyanate composition comprising Formula (IIA), (IIB), (IIC), (IIIA), (IIIB), or a combination thereof. In one embodiment, the resorcinol-blocked isocyanate composition comprises Formula (IIA) and (IIIA).

In a further embodiment, the dipping formulation further comprises a solvent.

In a further embodiment, the dipping formulation further comprises an additive which may be an epoxy-containing compound, a thickener, an antifoam or a combination thereof.

In a further embodiment, the dipping formulation further comprises a poly(vinyl pyridine/butadiene/styrene) latex.

In a further embodiment, the dipping formulation further comprises a resin solution which may be a resorcinol-formaldehyde solution.

In a further embodiment, the dipping formulation further comprises an additive which may be an antifoam.

In another aspect, disclosed herein are fabricated articles comprising a rubber material and a rubber reinforcing material treated with the dipping formulations disclosed herein.

In one embodiment, the rubber material in the fabricated article is a natural or synthetic rubber.

In one embodiment, the rubber reinforcing material in the fabricated article is in the form of fibers, filaments, fabrics or cords which may be made of a polyester, a polyamide, carbon, glass, steel, a polybenzoxazole or rayon.

In a further embodiment, the fabricated article is a tire, power transmission belt, conveyor belt, V-belt, hose printing roll, rubber shoe heel, rubber shoe sole, automobile floor mat, truck mud flap or ball mill liner.

In another aspect, disclosed herein are coatings comprising a resin prepared by curing Formula (B), (B'), (C) or a combination thereof:

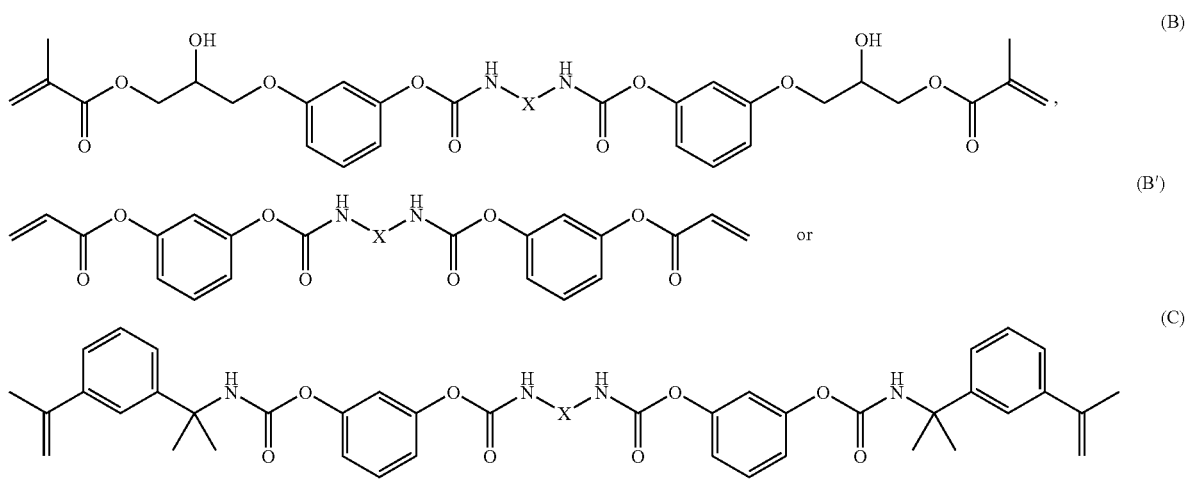

by heat, radiation or a combination thereof, wherein X is as defined above.

In one embodiment, the coating is cured in the presence of an initiator.

In a further embodiment, the coating further comprises an additive which may be a filler, rheology modifier, thickener, surfactant, wetting agent, cross-linking agent, coupling agent, colorant, lubricant, leveling agent, antioxidant, UV stabilizer, plasticizer or a combination thereof.

In another aspect, disclosed herein are coatings comprising a resin prepared by curing Formula (B), (E) or a combination thereof:

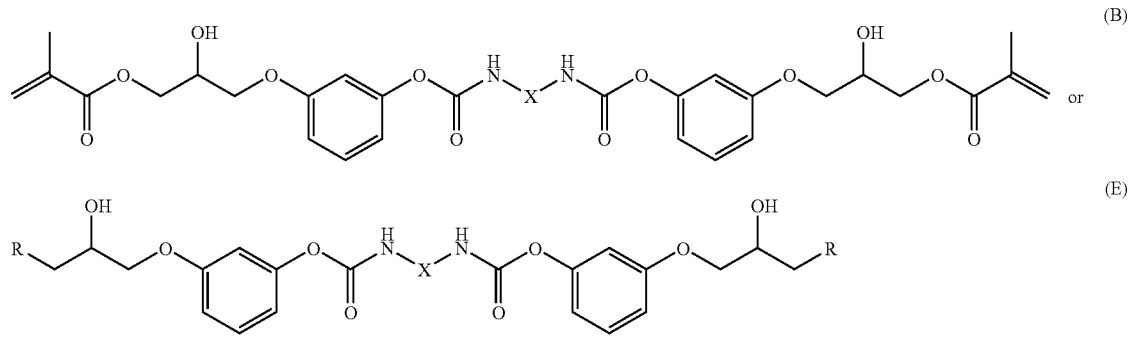

with a diisocyante, a polyisocyanate or a combination thereof, wherein X is as defined above; and R is alkyl, aryl, aralkyl, siloxanyl, silyl ether or a combination thereof.

In one embodiment, the coating further comprises an additive which may be a filler, rheology modifier, thickener, surfactant, wetting agent, cross-linking agent, coupling agent, colorant, lubricant, leveling agent, antioxidant, UV stabilizer, plasticizer or a combination thereof.

In another aspect, disclosed herein are resorcinol-blocked isocyanate compositions comprising a compound having Formula (IIC):

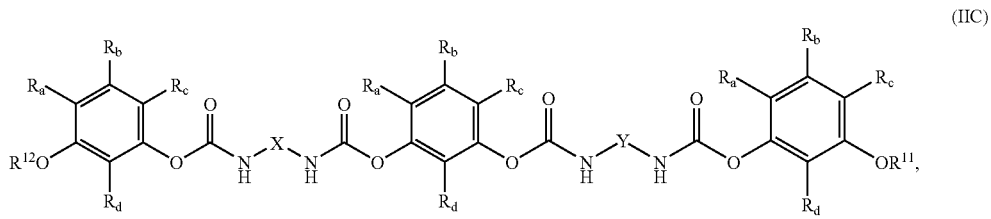

(IIC)

wherein X and Y are as defined above; each of $R_a$, $R_b$, $R_c$, and $R_d$ is independently hydrogen, hydroxyl, halide, nitro, benzo, carboxy, acyl, alkyl, aryl, aralkyl, or alkaryl; and each of $R^{11}$ and $R^{12}$ is independently H, acyl, alkyl, alkenyl, Formula (IV) or Formula (V):

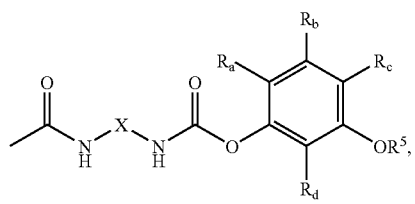

(IV)

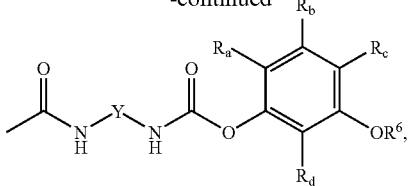

(V)

wherein each of $R^5$ and $R^6$ is independently H, acyl, alkyl or alkenyl.

In one embodiment, the resorcinol-blocked isocyanate composition has at least two melting temperatures or at least two unblocking temperatures.

In a further embodiment, the resorcinol-blocked isocyanate composition further comprises Formula (IIA), Formula (IIIA), Formula (IIB), Formula (IIIB):

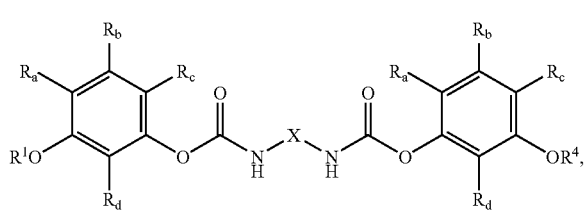

(IIA)

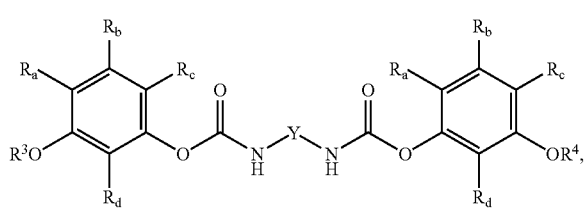

(IIIA)

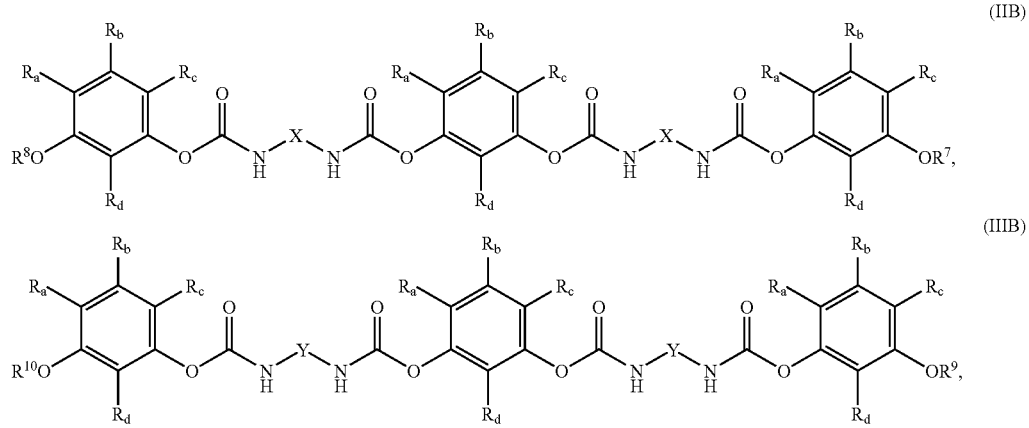

or a combination thereof; wherein X and Y are as defined above; each of $R_a$, $R_b$, $R_c$ and $R_d$ is independently hydrogen, hydroxyl, halide, nitro, benzo, carboxy, acyl, alkyl, aryl, aralkyl, or alkaryl; and each of $R^1$, $R^2$, $R^3$, $R^4$, $R^7$, $R^8$, $R^9$ and $R^{10}$ is independently H, acyl, alkyl, alkenyl, Formula (IV) or Formula (V).

In a further embodiment, the resorcinol-blocked isocyanate composition comprises Formula (IIC), Formula (IIA) and Formula (IIIA).

DESCRIPTION OF EMBODIMENTS OF THE INVENTION

Figure 1:
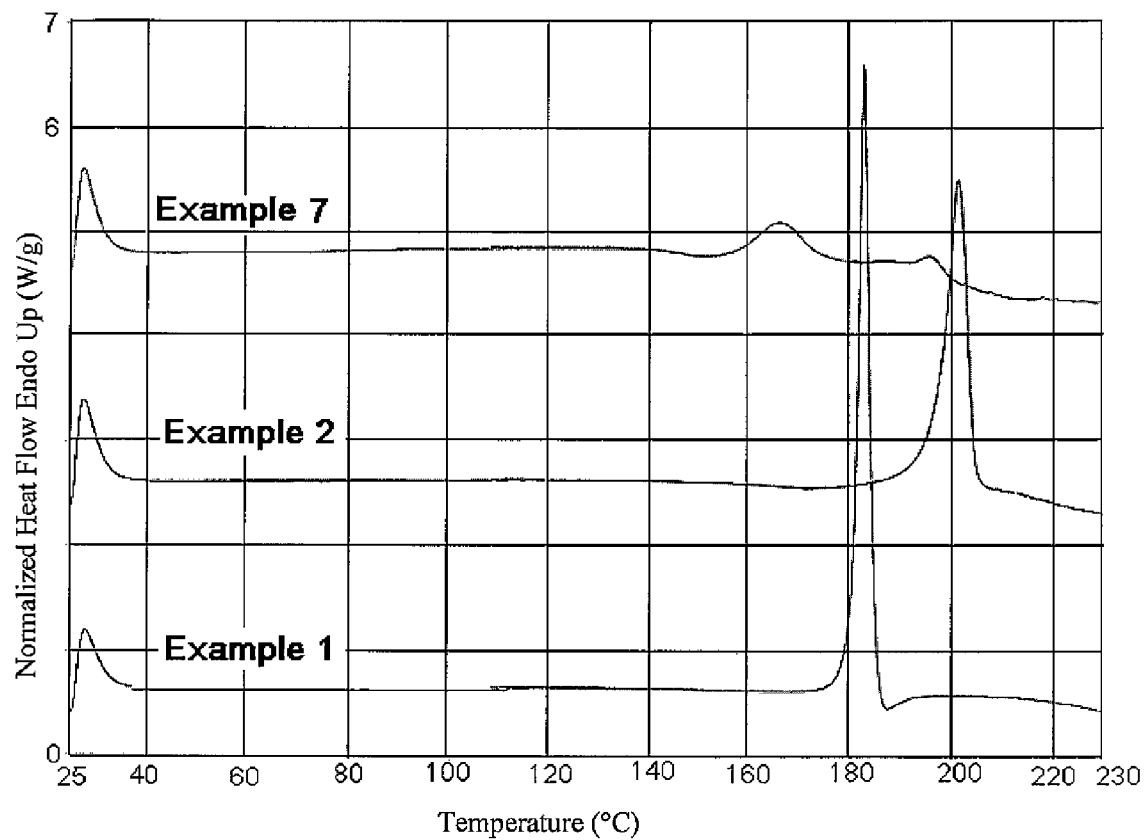
FIG. 1 depicts the DSC curves of Examples 1, 2 and 7.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, ..., 50 percent, 51 percent, 52 percent, ..., 95 percent, 96 percent, 97 percent, 98 percent, 99 percent, or 100 percent. Moreover, any numerical range defined by two R numbers as defined in the above is also specifically disclosed.

Disclosed herein are new resorcinol-blocked isocyanate compositions having two or more unblocking temperatures and/or melting temperatures. Generally, the resorcinol-blocked isocyanate compositions disclosed herein can improve the adhesion of various synthetic fiber materials to rubber compounds. In some embodiments, the resorcinol-blocked isocyanate compositions may be preparable or obtainable by reacting a resorcinol compound with at least two different isocyanate compounds.

For the purpose of blocking an isocyanate compound stoichiometrically with a resorcinol compound, the required amount of the resorcinol compound in moles generally depends on the isocyanate functionality of the isocyanate compound. The isocyanate functionality of the isocyanate compound is the number of isocyanate groups in each molecule of the isocyanate compound. For example, the isocyanate functionality of a monoisocyanate, diisocyanate or triisocyanate is 1, 2 or 3, respectively. Generally, it requires about 1, 2 or 3 moles of the resorcinol compound to block stoichiometrically a monoisocyanate, diisocyanate or triisocyanate, respectively. In some embodiments, the stoichiometric molar amounts of the resorcinol compound and the isocyanate compound are used. In other embodiments, a stoichiometric excess amount of the resorcinol compound is used. In further embodiments, a stoichiometric excess amount of the isocyanate compound is used.

When two or more isocyanate compounds are used, the required molar amount of the resorcinol compound for blocking stoichiometrically the two or more isocyanate compounds generally depends on the average isocyanate functionality of the two or more isocyanate compounds. The average isocyanate functionality of the two or more isocyanate compounds is the average of the isocyanate functionalities of the two or more isocyanate compounds. For example, the average isocyanate functionality of a mixture of two diisocyanates is 2 and the average isocyanate functionality of a mixture of a diisocyanate and a triisocyanate at a mole ratio of 50:50 is 2.5. Generally, for the purpose of blocking the two or more isocyanate compounds stoichiometrically, the mole ratio of the resorcinol compound to the two or more isocyanate compounds is about x:1 where x is the value of the average isocyanate functionality of the two or more isocyanate compounds. For example, it requires about 1, 1.5, 2, 2.5 or 3 moles of the resorcinol compound to block stoichiometrically the two or more isocyanate compounds having an average isocyanate functionality of 1, 1.5, 2, 2.5 or 3, respectively. In some embodiments, the stoichiometric molar amounts of the resorcinol compound and two or more isocyanate compounds are used. In some embodiments, a stoichiometric excess amount of the resorcinol compound is used. In other embodiments, a stoichiometric excess amount of the two or more isocyanate compounds is used. The stoichiometric excess amount of either the resorcinol compound or the two or more isocyanate compounds can be in the amount of 1%, 2%, 5%, 10%, 15%, 20%, 25%, 30%, 40%, 50%, 75%, 100%, 150% or 200% by mole.

Any resorcinol compound that is reactive toward isocyanates may be used to prepare the resorcinol-blocked isocyanate compositions disclosed herein. The resorcinol compound is described in Raj B. Durairaj, "*Resorcinol: Chemistry, Tech-* nology and Applications," Chapters 1-4, pp. 1-175 (2005), which is incorporated herein by reference. In some embodiments, the resorcinol compound may have Formula (I):

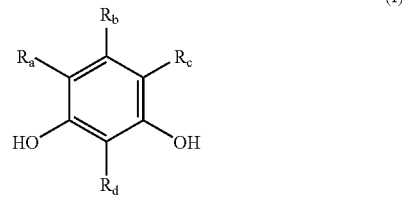

wherein each of $R_a$, $R_b$, $R_c$, and $R_d$ is independently hydrogen; hydroxy; halide such as fluoride, chloride, bromide and iodide; nitro; benzo; carboxy; acyl such as formyl, alkylcarbonyl (e.g. acetyl) and arylcarbonyl (e.g., benzoyl); alkyl such as methyl, ethyl, propyl, butyl, pentyl, hexyl, heptyl, octyl, nonyl, decyl, and the like; alkenyl such as unsubstituted or substituted vinyl and allyl; unsubstituted or substituted methacrylate; unsubstituted or substituted acrylate; silyl ether; siloxanyl; aryl such as phenyl and naphthyl; aralkyl such as benzyl; or alkaryl such as alkylphenyls.

In some embodiments, each of $R_a$, $R_b$, $R_c$ and $R_d$ of the resorcinol compound of Formula (I) is independently H, hydroxy, nitro, chloride, methyl, ethyl, vinyl, allyl, acrylate, methacrylate, aryl, alkaryl, silyl ether, siloxanyl, formyl, acetyl or carboxy. In other embodiments, each of $R_a$, $R_b$, $R_c$ and $R_d$ of the resorcinol compound of Formula (I) is independently H, hydroxyl, methyl or ethyl. In further embodiments, each of $R_a$, $R_b$, $R_c$ and $R_d$ of the resorcinol compound of Formula (I) is H.

In some embodiments, the resorcinol compound of Formula (I) is not functionalized, i.e., each of $R_a$, $R_b$, $R_c$ and $R_d$ of the resorcinol compound of Formula (I) is H. Generally, when a non-functionalized resorcinol compound is used to react with the isocyanates, non-functionalized resorcinol-blocked isocyanates can be obtained. In other embodiments, the resorcinol compound of Formula (I) is functionalized where at least one of $R_a$, $R_b$, $R_c$ and $R_d$ is a functional group such as hydroxy; halide such as fluoride, chloride, bromide and iodide; nitro; benzo; carboxy; acyl such as formyl, alkylcarbonyl (e.g. acetyl) and arylcarbonyl (e.g., benzoyl); alkyl such as methyl, ethyl, propyl, butyl, pentyl, hexyl, heptyl, octyl, nonyl, decyl, and the like; alkenyl such as unsubstituted or substituted vinyl and allyl; unsubstituted or substituted methacrylate; unsubstituted or substituted acrylate; silyl ether; siloxanyl; aryl such as phenyl and naphthyl; aralkyl such as benzyl; or alkaryl such as alkylphenyls. Generally, when a functionalized resorcinol compound is used to react with the isocyanates, functionalized resorcinol-blocked isocyanates can be obtained.

The functionalized resorcinol-blocked isocyanates can be used as curing agents for both rubber and non-rubber applications such as polyurethane and polyurea applications. Further, as described later, the functionalized resorcinol-blocked isocyanates can also be used to prepare functionalized derivatives such as functionalized methacrylate, acrylate, alkenyl such as vinyl and allylic, alkyl, aryl, aralkyl, siloxanyl, and silyl ether compounds for a variety of applications such as coating applications.

Some non-limiting suitable examples of the resorcinol compound include non-functionalized resorcinol compounds such as resorcinol; and functionalized resorcinol compounds such as orcinol, 2-methylresorcinol, phloroglucinol, 1,2,4-benzenetriol, pyrogallol, 3,5-dihydroxybenzaldehyde, 2,4-dihydroxybenzaldehyde, 4-ethylresorcinol, 2,5-dimethylresorcinol, 5-methylbenzene-1,2,3-triol, 3,5-dihydroxybenzyl alcohol, 2,4,6-trihydroxytoluene, 4-chlororesorcinol, 2',6'-dihydroxyacetophenone, 2',4'-dihydroxyacetophenone, 3',5'-dihydroxyacetophenone, 2,4,5-trihydroxybenzaldehyde, 2,3,4-trihydroxybenzaldehyde, 2,4,6-trihydroxybenzaldehyde, 3,5-dihydroxybenzoic acid, 2,4-dihydroxybenzoic acid, 2,6-dihydroxybenzoic acid, 1,3-dihydroxynaphthalene, 2',4'-dihydroxypropiophenone, 2',4'-dihydroxy-6'-methylacetophenone, 1-(2,6-dihydroxy-3-methylphenyl)ethanone, 3-methyl 3,5-dihydroxybenzoate, methyl 2,4-dihydroxybenzoate, gallacetophenone, 2,4-dihydroxy-3-methylbenzoic acid, 2,6-dihydroxy-4-methylbenzoic acid, methyl 2,6-dihydroxybenzoate, 2-methyl-4-nitroresorcinol, 2,4,5-trihydroxybenzoic acid, 3,4,5-trihydroxybenzoic acid, 2,3,4-trihydroxybenzoic acid, 2,4,6-trihydroxybenzoic acid, 2-nitrophloroglucinol or a combination thereof. In some embodiments, the resorcinol compound is resorcinol, orcinol, 2-methylresorcinol, phloroglucinol, 1,2,4-benzenetriol, pyrogallol, 3,5-dihydroxybenzaldehyde, 2,4-dihydroxybenzaldehyde, 4-ethylresorcinol, 4-chlororesorcinol or a combination thereof. In further embodiments, the resorcinol compound is resorcinol.

The resorcinol compound can be optionally replaced partially or completely with at least another isocyanate blocking agent such as phenol compounds (e.g., phenol, p-chlorophenol, o-nitrophenol and m-cresol), alcohols, oximes, beta-dicarbonyl compounds (e.g., diethyl malonate, ethyl acetoacetate, acetyl acetone, and malononitrile), lactams (e.g., caprolactam), mercaptans, amines, carbamates, amides, imines, carboxylic acids, imidazoles (e.g., benzimidazole, 2-phenylimidazole), and the like. In some embodiments, the resorcinol compound is replaced partially or completely with caprolactam, a phenol compound, or a combination thereof. In other embodiments, the resorcinol compound is replaced partially or completely with a phenol compound having Formula (IA):

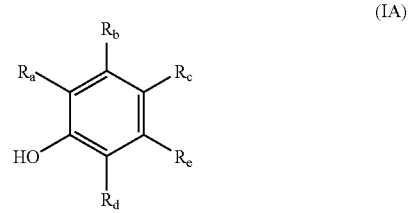

wherein each of $R_a$, $R_b$, $R_c$, $R_d$ and $R_e$ of the phenol compound of Formula (IA) is independently hydrogen; hydroxy; halide such as fluoride, chloride, bromide and iodide; nitro; benzo; carboxy; acyl such as formyl, alkylcarbonyl (e.g. acetyl) and arylcarbonyl (e.g., benzoyl); alkyl such as methyl, ethyl, propyl, butyl, pentyl, hexyl, heptyl, octyl, nonyl, decyl, and the like; aryl such as phenyl and naphthyl; aralkyl such as benzyl; or alkaryl such as alkylphenyls. In other embodiments, each of $R_a$, $R_b$, $R_c$, $R_d$ and $R_e$ of the phenol compound of Formula (IA) is independently H, halide, or alkyl. In a particular embodiment, each of $R_a$, $R_b$, $R_c$, $R_d$ and $R_e$, of the phenol compound of Formula (I) is H. Some blocking agents are disclosed in Zeno W. Wickes, Jr., "Blocked Isocyanates," *Progress in Organic Coatings*, Volume 3, Pages 73-79 (1973), which is incorporated herein by reference. Some blocking agents are also disclosed in U.S. Pat. Nos. 6,509, 433; 6,368,669; 6,242,530; 6,063,860; 5,986,033; 5,352,755; 5,246,557; 4,976,837; and 3,987,033, all of which are incorporated herein by reference.

The mole ratio of the resorcinol compound to the at least another isocyanate blocking agent can be from about 1:99 to about 99:1 or any other ratios that is recognized by a skilled artisan. In some embodiments, the mole ratio of the resorcinol compound to the at least another isocyanate blocking agent is from about 5:95 to about 95:5, from about 10:90 to about 90:10, from about 15:85 to about 85:15, from about 20:80 to about 80:20, from about 25:75 to about 75:25, from about 70:30 to about 30:70, from about 40:60 to about 60:40 or at about 50:50. In other embodiments, the resorcinol compound is completely replaced with the at least another isocyanate blocking agent. In further embodiment, the resorcinol compound is not replaced with another isocyanate blocking agent.

Any isocyanate compound that can react with a hydroxyl compound may be used for the preparation of the resorcinol-blocked isocyanate compositions. Some non-limiting examples of suitable isocyanate compounds include monoisocyanates such as alkyl isocyanates (e.g., methyl isocyanate and ethyl isocyanate), cycloalkyl isocyanate (e.g., cyclopropyl isocyanate, cyclobutyl isocyanate, cyclopentyl isocyanate, cyclohexyl isocyanate and trans-4-methylcyclohexyl isocyanate), aryl isocyanates (e.g., phenyl isocyanate, 4-chlorophenyl isocyanate, 2,4-difluorophenyl isocyanate, 2,6-dimethylphenyl isocyanate, 2,6-diisopropylphenyl isocyanate, tolyl isocyanate, and naphthyl isocyanate), aralkyl isocyanates (e.g., methylbenzyl isocyanate), unsaturated isocyanates, halogenated alkyl and aryl isocyanates, carbonyl, thiocarbonyl and imidoyl isocyanates, sulfur isocyanates, phosphorous isocyanates, and inorganic isocyanates; diisocyanates such as aliphatic diisocyanates and aromatic diisocyanates; triisocyanates such as 4,4',4"-triphenylmethane triisocyanates (e.g., DESMODUR® R from Bayer MaterialScience, Pittsburgh, Pa.), tris-(4-isocyanatophenyl) thiophosphate (e.g., DESMODUR® RF from Bayer MaterialScience) and biuret of hexamethylene diisocyanate (e.g., DESMODUR® N from Bayer MaterialScience); and other polyisocyanates such as MONDUR® MRS, MONDUR® MR Light, MONDUR® MRS 2, MONDUR® MRS 4, MONDUR® MRS 5, BAYHYDUR®, BAYMIDUR® and DESMODUR® polyisocyanates from Bayer MaterialScience and TOLONATE® X C3 polyisocyanate from Rhodia, Cranbury, N.J. In some embodiments, the polyisocyanates are MDI-based polyisocyanates (PMDIs) including MONDUR® MRS, MONDUR® MR Light, MONDUR® MRS 2, MONDUR® MRS 4 and MONDUR® MRS 5. Some isocyanates suitable for this invention are disclosed in Henri Ulrich, "*Chemistry and Technology of Isocyanates*," John Wiley & Sons (1997), which is incorporated herein by reference in its entirety.

Some non-limiting examples of suitable aromatic diisocyanates include 2,4-toluene diisocyanate (2,4-TDI; e.g., MONDUR® TDS from Bayer MaterialScience), 2,6-toluene diisocyanate (2,6-TDI), 2,2'-diphenylmethane diisocyanate (2,2'-MDI), 4,4'-diphenylmethane diisocyanate (4,4'-MDI, e.g., MONDUR® M and MONDUR® CD from Bayer MaterialScience and ISONATE® 125 from Dow), 2,4'-diphenylmethane diisocyanate (2,4'-MDI), 1,5-naphthylene diisocyanate (NDI; e.g., DESMODUR® 15 from Bayer and TAKENATE® 700 from Mitsui Takeda Chemicals, Inc., Tokyo, Japan), 1,4-phenylene diisocyanate (PDI), dimerized toluene diisocyanate (e.g., DESMODUR® TT from Bayer MaterialScience), ethylene diphenylene diisocyanate (EDI), and combinations thereof (e.g., an isocyanate mixture comprising 2,4'-MDI and 4,4'-MDI such as MONDUR® ML from Bayer MaterialScience.

Some non-limiting examples of suitable aliphatic diisocyanates or triisocyanates include 4,4'cyclohexylmethane diisocyanate ($H_{12}MDI$; e.g., DESMODUR® W from Bayer), hexamethylene 1,6-diisocyanate (1,6-HDI; e.g., MONDUR® HX from Bayer MaterialScience and COSMONATE® ND from Mitsui Takeda Chemicals, Inc.), isophorone diisocyanate (IPDI; available from Huels America Inc., Somerset, N.J.), 2,2,4-trimethyl-hexamethylene diisocyanate (2,2,4-TMDI; available from Huels America Inc.), 2,4,4-trimethyl-hexamethylene diisocyanate (2,4,4-TMDI; available from Huels America Inc.), trimer of hexamethylene 1,6-diisocyanate (e.g., DESMODUR® N 3300 from Bayer MaterialScience), trimer of isophorone diisocyanate (e.g., ISOCYANATE® T 1890 from Huels America Inc.), 1,4-cyclohexane diisocyanate (CHDI; available from Akzo, Chicago, Ill.), m-tetramethylxylene diisocyanate (m-TMXDI; available from American Cyanamid, Wayne, N.J.), p-tetramethylxylene diisocyanate (p-TMXDI; available from American Cyanamid), xylene diisocyanate (XDI; e.g., TAKENATE® 500; available from Mitsui Takeda Chemicals, Inc), norbornanediisocyanate (NBDI; e.g., COSMONATE® NBDI from Mitsui Takeda Chemicals, Inc.), and 1,3-bis(isocyanatomethyl)cyclohexane ($H_6XDI$; e.g., TAKENATE® 600; available from Mitsui Takeda Chemicals, Inc).

In some embodiments, each of the at least two isocyanate compounds is independently a monoisocyanate, a diisocyanate, a triisocyanate or a higher polyisocyanate. In other embodiments, one of the at least two isocyanate compounds is a monoisocyanate and another is a diisocyanate. In further embodiments, one of the at least two isocyanate compounds is a monoisocyanate and another is a triisocyanate. In further embodiments, one of the at least two isocyanate compounds is a diisocyanate and another is a triisocyanate.

In certain embodiments, each of the at least two isocyanate compounds is a diisocyanate. In further embodiments, each of the two diisocyanate compounds is an aromatic diisocyanate such as MDI, TDI, PDI and EDI. In further embodiments, each of the two diisocyanate compounds is an aliphatic diisocyanate such as $H_{12}MDI$, 1,6-HDI, IPDI, 2,2,4-TMDI, 2,4,4-TMDI, CHDI, m-TMXDI, p-TMXDI, XDI and $H_6XDI$. In further embodiments, one of the two diisocyanate compounds is an aromatic diisocyanate and another is an aliphatic diisocyanate. In further embodiments, one of the two diisocyanate compounds is or comprises an MDI (e.g., 2,4'-MDI and 4,4'-MDI) and another is or comprises a TDI (e.g., 2,4-TDI and 2,6-TDI). In particular embodiments, the two diisocyanate compounds are or comprise 2,4'-MDI and 4,4'-MDI, such as MONDUR® ML from Bayer MaterialScience.

When two isocyanate compounds are used, the mole ratio of the two isocyanate compounds can be between about 99:1 and about 1:99, between about 95:5 and about 5:95, or between about 90:10 and about 10:90. In some embodiments, the mole ratio of the two isocyanate compounds is between about 85:15 and about 15:85 or between about 80:20 and about 20:80. between about 75:25 and about 25:75. In further embodiments, the mole ratio of the two isocyanate compounds is between about 70:30 and about 30:70. In further embodiments, the mole ratio of the two isocyanate compounds is between about 65:35 and about 35:65. In further embodiments, the mole ratio of the two isocyanate compounds is between about 60:40 and about 40:60, between about 55:45 and about 45:55 or at about 50:50.

When two or more isocyanate compounds are used, the mole fraction of each isocyanate compound with respect to all isocyanate compounds can be greater than or equal to about 0.01, about 0.02, about 0.04, about 0.05, about 0.075, about 0.10, about 0.15, about 0.20 or about 0.25. In some embodiments, the mole fraction of each isocyanate compounds with respect to all isocyanate compounds is greater than or equal to about 0.05, about 0.15 or about 0.25. When two or more isocyanate compounds are used, the mole fraction of each isocyanate compound with respect to all isocyanate compounds can be less than or equal to about 0.99, about 0.975, about 0.95, about 0.90, about 0.85, about 0.80, about 0.75, about 0.70, about 0.65, about 0.60, about 0.55, or about 0.50. In some embodiments, the mole fraction of each isocyanate compound with respect to all isocyanate compounds is less than or equal to about 0.85, about 0.75, about 0.65. In further embodiments, the mole fraction of each isocyanate compound with respect to all isocyanate compounds is between about 0.01 and about 0.99, between about 0.02 and about 0.98, between about 0.05 and about 0.95, between about 0.10 and about 0.90, between about 0.15 and about 0.85, between about 0.20 and about 0.80 or between about 0.25 and about 0.75.

The reaction between the resorcinol compound of Formula (I) with the at least two isocyanate compounds can occur in the presence or absence of a solvent. In some embodiments, the reaction occurs in a solvent such as tetrahydrofuran, diethyl ether, methyl ethyl ketone, acetone acetonitrile, N,N-dimethyl formamide or a combination thereof. In other embodiments, the reaction occurs in the absence of a solvent.

Any reaction temperature that is suitable for the reaction between the resorcinol compound of Formula (I) with the at least two isocyanate compounds can be used. In some embodiments, the reaction temperature can be higher than about 25° C., about 35° C., about 45° C., about 55° C., about 65° C., about 75° C., about 80° C., about 85° C., about 90° C., about 95° C., about 100° C., about 105° C., about 110° C., about 115° C., or about 120° C. In the presence of a solvent, the reaction temperature can be the boiling point of the solvent. In the absence of a solvent, the reaction temperature can be above the melting point of the resorcinol compound or the melting point of one of the at least two isocyanate compounds. In some embodiments, the reaction occurs without a solvent and the reaction temperature is above the melting point of the resorcinol compound.

Any catalyst that is suitable for the reaction between the resorcinol compound of Formula (I) with the isocyanate compounds can be used. In some embodiments, the catalyst is 3-methyl-1-phenyl-2-phospholene-1-oxide, dibutyltin dilaurate, a urethane catalyst, a tertiary amine catalyst, a tin salt or a combination thereof. In other embodiments, the catalyst is 3-methyl-1-phenyl-2-phospholene-1-oxide or dibutyltin dilaurate.

In some embodiments, the resorcinol-blocked isocyanate composition is obtainable or preparable by reacting the resorcinol compound of Formula (I) with a diisocyanate mixture comprising formulae O=C=N—X—N=C=O and O=C=N—Y—N=C=O wherein X and Y are different and each of X and Y is or comprises independently alkylene, cycloalkylene, arylene, cycloalkarylene, alkarylene, aralkylene, heterocyclylene, heteroarylene or a combination thereof. The alkylene, cycloalkylene, arylene, alkarylene, cycloalkarylene, aralkylene, heterocyclylene, heteroarylene radicals can be optionally substituted with alkyl, aryl, alkaryl, cycloalkaryl, aralkyl, alkenyl, alkynyl, acyl, carboxy, heterocyclyl, halide, nitro, hydroxy, —N=C=O, —N=C=S or a combination thereof. In other embodiments, each of X and Y is independently a divalent radical having one of the following the formulae:

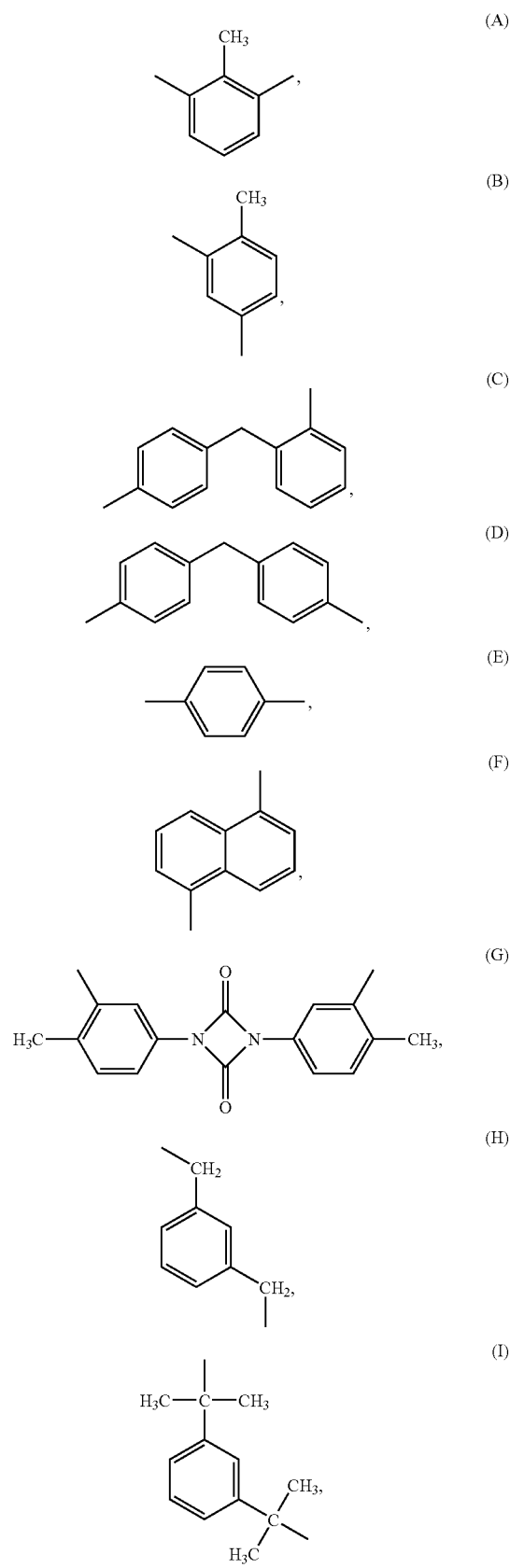

-continued (J) 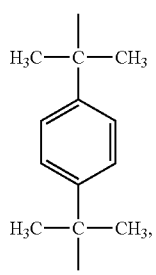

(K) 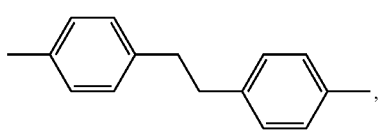

(L) 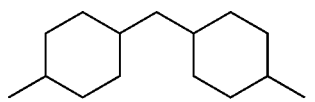

(M) 

(N) 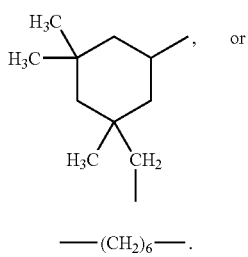

or (O) —(CH$_2$)$_6$—.

The resorcinol-blocked isocyanate composition preparable or obtainable from the reaction between Formula (I) and a mixture of O=C=N—X—N=C=O and O=C=N—Y—N=C=O may comprise a first compound having Formula (IIA):

(IIA) 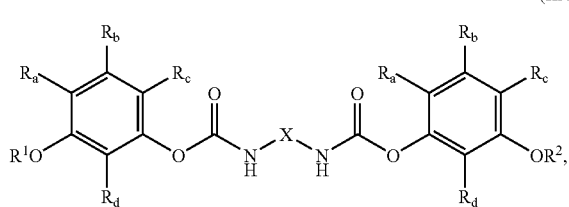

and a second compound having Formula (IIIA):

(IIIA) 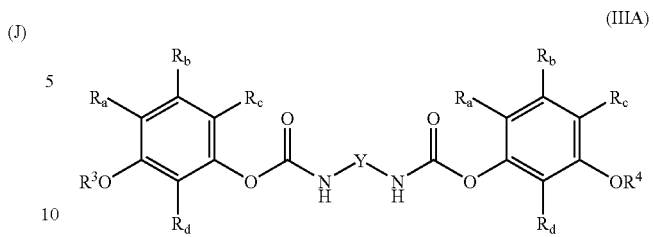

wherein $R_a$, $R_b$, $R_c$, $R_d$, X and Y are as defined above; and each of $R^1$, $R^2$, $R^3$ and $R^4$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (IVA), Formula (IVB), Formula (IVC), Formula (IVD), Formula (IVE) or Formula (IVF):

(IVA) 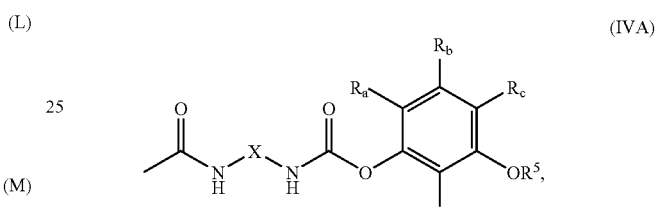

(IVB) 

(IVC) 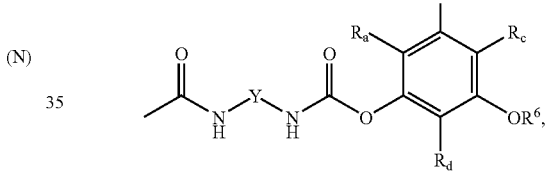

(IVD) 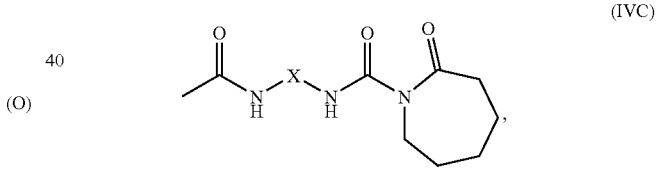

(IVE) 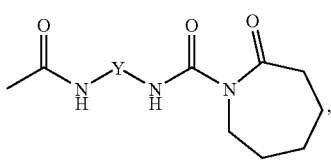

(IVF) 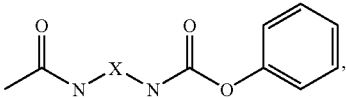

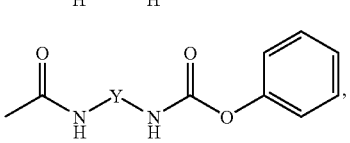

wherein each of X, Y, $R_a$, $R_b$, $R_c$ and $R_d$ is as defined above; and each of $R^5$ and $Re^6$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (IVA), Formula (IVB), Formula (IVC), Formula (IVD), Formula (IVE) or Formula (IVF). In some embodiments, each of $R^5$ and $R^6$ is independently H, acyl, alkyl or alkenyl. In other embodiments, each of $R^5$ and $R^6$ is H. In other embodiments, X of Formula (IVC) or Formula (IVE) is a divalent radical having Formula (C) and X of Formula (IVD) or Formula (IVF) is a divalent radical having Formula (D).

The mole ratio of Formula (IIA) to Formula (IIIA) can be from about 1:99 to about 99:1. In some embodiments, the mole ratio of Formula (IIA) to Formula (IIIA) is between about 5:95 and about 95:5, between about 10:90 and about 90:10, between about 15:85 and about 85:15, between about 20:80 and about 80:20, between about 25:75 and about 75:25, between about 30:70 and about 70:30, between about 35:65 and about 65:35 or between about 40:60 and about 60:40. In other embodiments, the mole ratio of Formula (IIA) to Formula (IIIA) is between about 10:90 and about 90:10. In other embodiments, the mole ratio of Formula (IIA) to Formula (IIIA) is between about 10:90 and about 90:10. In further embodiments, the mole ratio of Formula (IIA) to Formula (IIIA) is between about 20:80 and about 80:20. In further embodiments, the mole ratio of Formula (IIA) to Formula (IIIA) is between about 35:65 and about 65:35.

In addition to Formulae (IIA) and (IIIA), the resorcinol-blocked isocyanate composition may further comprise a third compound having Formula (IIB):

wherein each of $R_a$, $R_b$, $R_c$ and $R_d$ is as defined above; and each of $R^7$, $R^8$, $R^9$, $R^{10}$, $R^{11}$ and $R^{12}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (IVA), Formula (IVB), Formula (IVC), Formula (IVD), Formula (IVE) or Formula (IVF), with the proviso that the compounds of Formulae (IIA), (IIB), (IIC), (IIIA) and (IIIB) are different from each other.

In some embodiments, the resorcinol-blocked isocyanate composition comprises a compound having Formula (IIA), (IIB), (IIC), (IIIA), (IIIB) or a combination thereof. In further embodiments, the resorcinol-blocked isocyanate composition comprises Formula (IIA) and (IIIA). In further embodiments, the resorcinol-blocked isocyanate composition comprises Formula (IIC). In further embodiments, the resorcinol-blocked isocyanate composition comprises Formulae (IIA), (IIC) and (IIIA). In further embodiments, the resorcinol-blocked isocyanate composition comprises Formulae (IIA), (IIB), (IIC), (IIIA) and (IIIB).

In some embodiments of the resorcinol-blocked isocyanate composition, each of $R_a$, $R_b$, $R_c$ and $R_d$ of Formulae (IIA), (IIB), (IIC), (IIIA) or (IIIB) is hydrogen. In other embodiments, each of $R^1$, $R^2$, $R^3$ and $R^4$ is H. In further embodiments, each of $R^7$, $R^8$, $R^9$, $R^{10}$, $R^{11}$ and $R^{12}$ is hydrogen. In further embodiments, each of $R_a$, $R_b$, $R_c$, $R_d$, $R^1$, $R^2$, $R^3$, $R^4$, $R^7$, $R^8$,

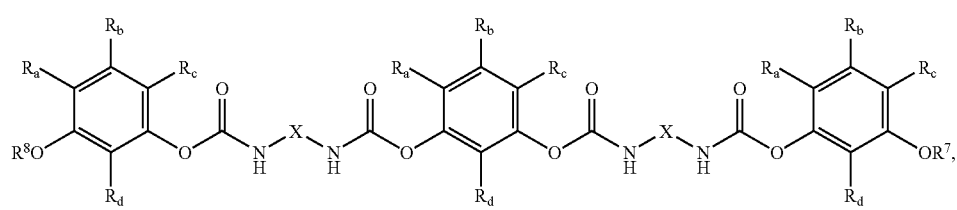

and/or a fourth compound having Formula (IIC):

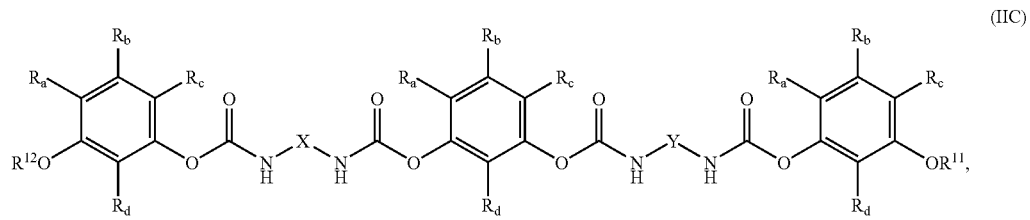

and/or a fifth compound having Formula (IIIB):

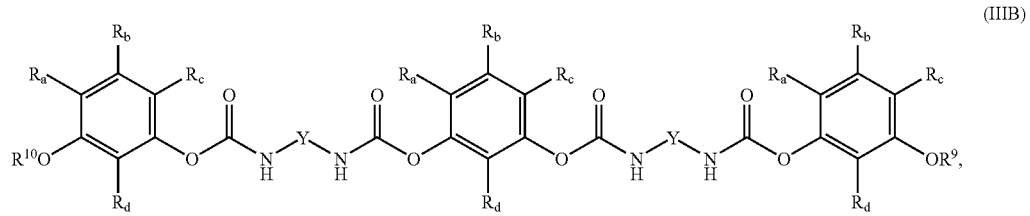

$R^9$, $R^{10}$, $R^{11}$ and $R^{12}$ is hydrogen. In particular embodiments, X of Formulae (IIA), (IIB) and (IIC) is a divalent radical having Formula (C) and Y of Formulae (IIC), (IIIA) and (IIIB) is a divalent radical having Formula (D). In further embodiments, X of Formulae (IIA), (IIB) and (IIC) comprises at least a divalent radical having Formula (C) and/or Formula (D) and Y of Formulae (IIC), (IIIA) and (IIIB) comprises at least a divalent radical having Formula (A) and/or Formula (B). In a particular embodiment of the resorcinol-blocked isocyanate composition comprising Formulae (IIA), (IIB), (IIC), (IIIA) and (IIIB), each of $R_a$, $R_b$, $R_c$, $R_d$, $R^1$, $R^2$, $R^3$, $R^4$, $R^7$, $R^5$, $R^9$, $R^{10}$, $R^{11}$ and $R^{12}$ is hydrogen; X is a divalent radical having Formula (C); Y is a divalent radical having Formula (D).

The resorcinol-blocked isocyanate composition may be obtainable or preparable by reacting the resorcinol compound of Formula (I) with a mixture of MDI isomers such as 2,4'-MDI [i.e., O=C=N—X—N=C=O where X is Formula (C)] and 4,4'-MDI [i.e., O=C=N—Y—N=C=O where Y is Formula (D)]; a mixture of TDI isomers such as 2,4-TDI [i.e., O=C=N—X—N=C=O where X is Formula (B)] and 2,6-TDI [i.e., O=C=N—Y—N=C=O where Y is Formula (A)] or a mixture of an MDI isomer and a TDI isomer. In other embodiments, the resorcinol-blocked isocyanate composition is preparable from the reaction between Formula (I) and a diisocyanate mixture comprising 2,4'-MDI and 4,4'-MDI and the composition may comprise a first compound having Formula (VIA):

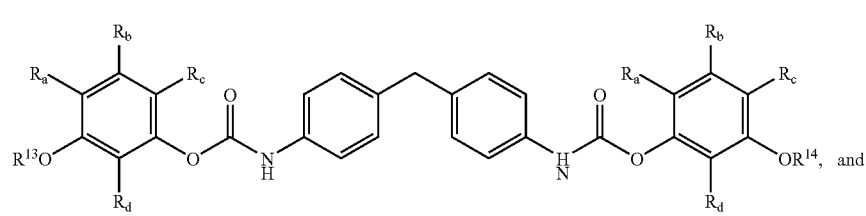

a second compound having Formula (VIIA):

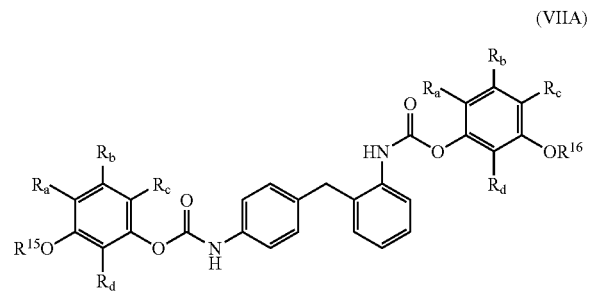

wherein each of $R_a$, $R_b$, $R_c$ and $R_d$ is defined above; and each of $R^{13}$, $R^{14}$, $R^{15}$ and $R^{16}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (VIII) or Formula (IX) or Formula (X):

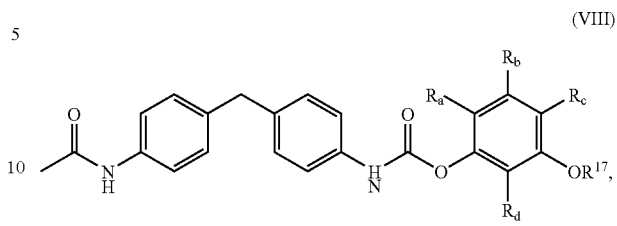

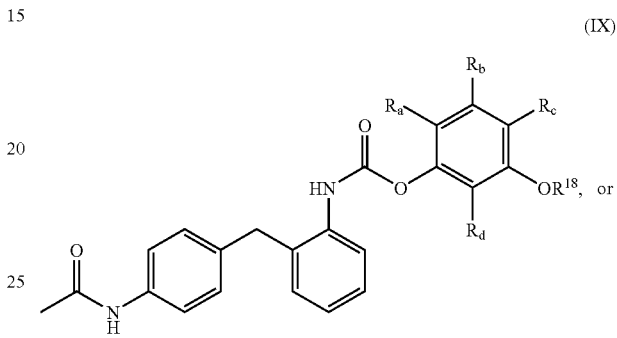

-continued

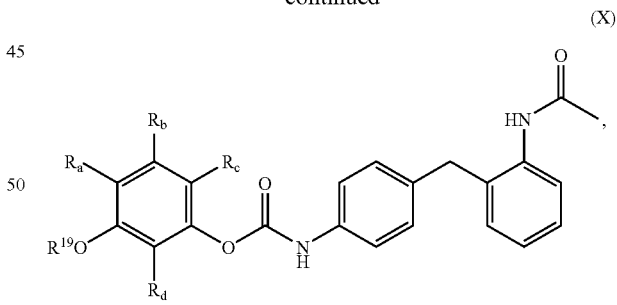

wherein each of $R^{17}$, $R^{18}$ and $R^{19}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (VIII) or Formula (IX) or Formula (X). In some embodiments, each of $R^{17}$, $R^{18}$ and $R^{19}$ is independently H, acyl, alkyl or alkenyl. In other embodiments, each of $R^{17}$, $R^{18}$ and $R^{19}$ is H.

In addition to Formula (VIA) and (VIIA), the resorcinol-blocked isocyanate composition may further comprise a third compound having Formula (VIB):

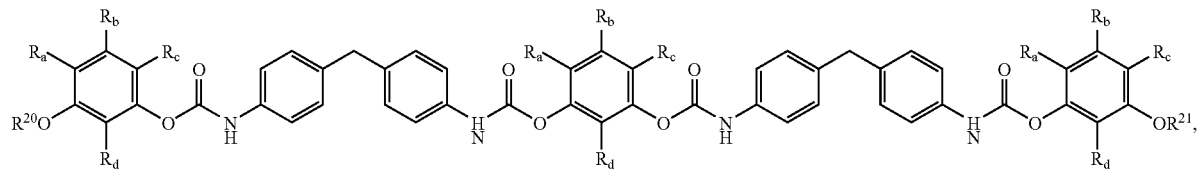

(VIB)

and/or a fourth compound having Formula (VIC):

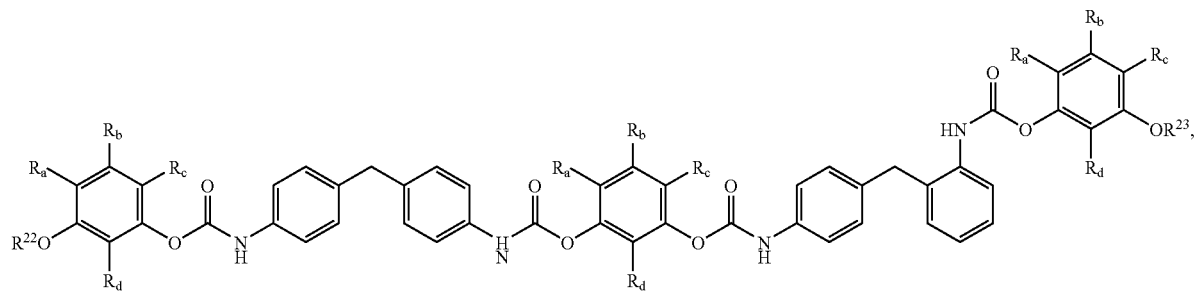

(VIC)

and/or a fifth compound having Formula (VIIB):

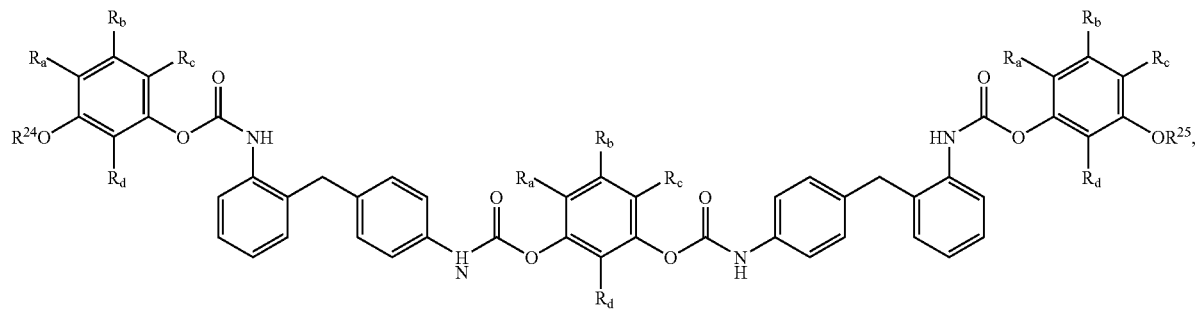

(VIIB)

wherein each of $R_a$, $R_b$, $R_c$ and $R_d$ is defined above; and each of $R^{20}$, $R^{21}$, $R^{22}$, $R^{23}$, $R^{24}$ and $R^{25}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (VIII), Formula (IX) or Formula (X), with the proviso that the compounds of Formulae (VIA), (VIB), (VIC), (VIIA) and (VIIB) are different from each other.

In some embodiments, the resorcinol-blocked isocyanate composition comprises Formula (VIA), (VIB), (VIC), (VIIA), (VIIB) or a combination thereof. In further embodiments, the resorcinol-blocked isocyanate composition comprises Formulae (VIA) and (VIIA). In further embodiments, the resorcinol-blocked isocyanate composition comprises Formula (VIC). In further embodiments, the resorcinol-blocked isocyanate composition comprises Formulae (VIA), (VIC) and (VIIA). In further embodiments, the resorcinol-blocked isocyanate composition comprises Formulae (VIA), (VIB), (VIC), (VIIA) and (VIIB).

In some embodiments of the resorcinol-blocked isocyanate composition, each of $R_a$, $R_b$, $R_c$ and $R_d$ of Formulae (VIA), (VIB), (VIC), (VIIA) or (VIIB) is hydrogen. In other embodiments, each of $R^{13}$, $R^{14}$, $R^{15}$ and $R^{16}$ is H. In further embodiments, each of $R^{20}$, $R^{21}$, $R^{22}$, $R^{23}$, $R^{24}$ and $R^{25}$ is hydrogen. In particular embodiments, each of $R_a$, $R_b$, $R_c$, $R_d$, $R^{13}$, $R^{14}$, $R^{15}$, $R^{16}$, $R^{20}$, $R^{21}$, $R^{22}$, $R^{23}$, $R^{24}$ and $R^{25}$ is hydrogen.

The resorcinol-blocked isocyanate composition may be prepared by reacting resorcinol (i.e., Formula (I) where each of $R_a$, $R_b$, $R_c$ and $R_d$ is H) with a mixture of MDI isomers such as 2,4'- and 4,4'-MDI, a mixture of an MDI and a TDI, or a mixture of TDI isomers such as 2,4-TDI and 2,6-TDI. In other embodiments, the resorcinol-blocked isocyanate composition is prepared from the reaction between resorcinol and a diisocyanate mixture comprising 2,4'-MDI and 4,4'-MDI and the composition may comprise a first compound having Formula (XIA):

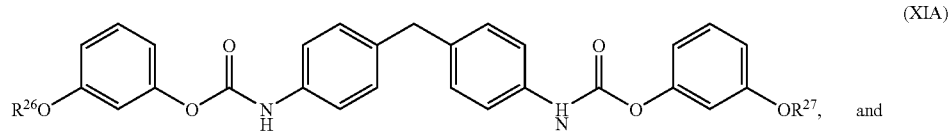

a second compound having Formula (XIIA):

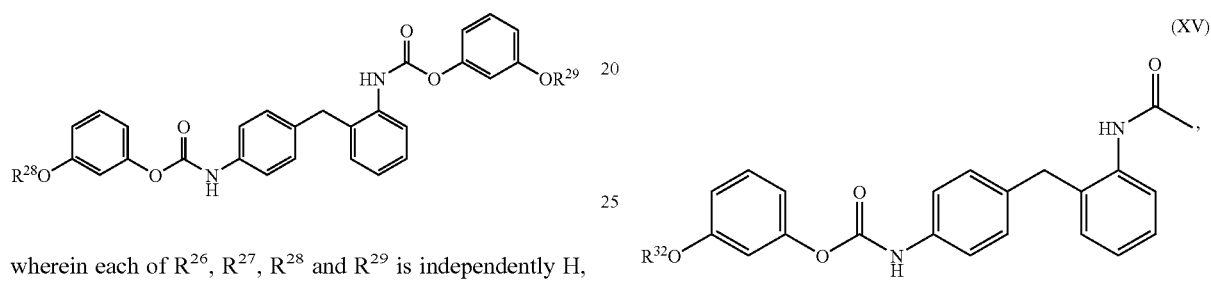

wherein each of $R^{26}$, $R^{27}$, $R^{28}$ and $R^{29}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (XIII) or Formula (XIV) or Formula (XV):

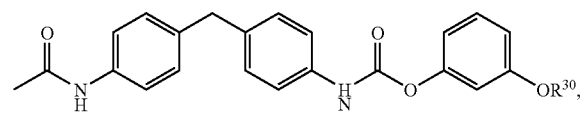

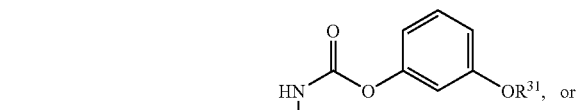

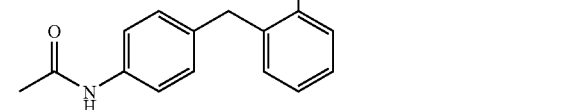

wherein each of $R^{30}$, $R^{31}$ and $R^{32}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (XIII) or Formula (XIV) or Formula (XV). In some embodiments, each of $R^{30}$, $R^{31}$ and $R^{32}$ is independently H, acyl, alkyl or alkenyl. In other embodiments, each of $R^{30}$, $R^{31}$ and $R^{32}$ is H.

In addition to Formula (XIA) and (XIIA), the resorcinol-blocked isocyanate composition may further comprise a third compound having Formula (XIB):

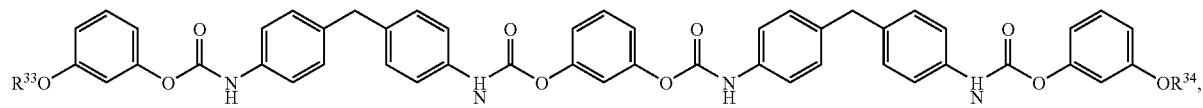

and/or a fourth compound having Formula (XIIC):

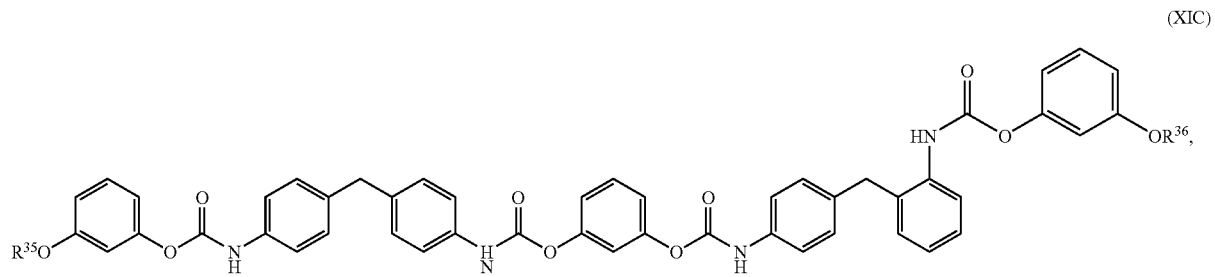

and/or a fifth compound having Formula (XIIIB):

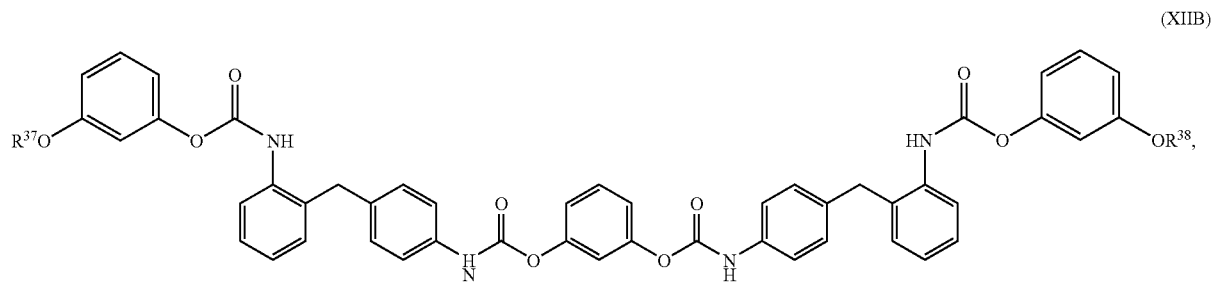

wherein each of $R^{33}$, $R^{34}$, $R^{35}$, $R^{36}$, $R^{37}$ and $R^{38}$ is independently H, acyl, alkyl, alkenyl such as unsubstituted or substituted vinyl and allyl, aryl, aralkyl, unsubstituted or substituted methacrylate, unsubstituted or substituted acrylate, silyl ether, siloxanyl, Formula (XIII), Formula (XIV) or Formula (XV), with the proviso that the compounds of Formulae (XIA), (XIB), (XIC), (XIIA) and (XIIB) are different from each other.

In some embodiments, the resorcinol-blocked isocyanate composition comprises Formula (XIA), (XIB), (XIC), (XIIA), (XIIB) or a combination thereof. In further embodiments, the resorcinol-blocked isocyanate composition comprises Formulae (XIA) and (XIIA). In further embodiments, the resorcinol-blocked isocyanate composition comprises Formula (XIC). In further embodiments, the resorcinol-blocked isocyanate composition comprises Formulae (XIA), (XIC) and (XIIA). In further embodiments, the resorcinol-blocked isocyanate composition comprises Formulae (XIA), (XIB), (XIC), (XIIA) and (XIIB).

In some embodiments of the resorcinol-blocked isocyanate composition comprising Formulae (XIA), (XIB), (XIC), (XIIA) and (XIIB), each of $R^{26}$, $R^{27}$, $R^{28}$, $R^{29}$, $R^{33}$, $R^{34}$, $R^{35}$, $R^{36}$, $R^{37}$ and $R^{38}$ is hydrogen. In other embodiments, the resorcinol-blocked isocyanate composition comprises Compound (1), Compound (2), Compound (3), Compound (4), Compound (5) or a combination thereof. Compounds (1)-(5) have the following formulae:

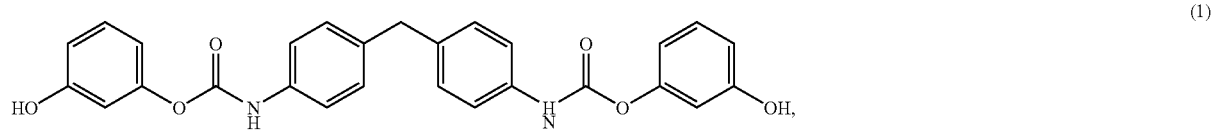

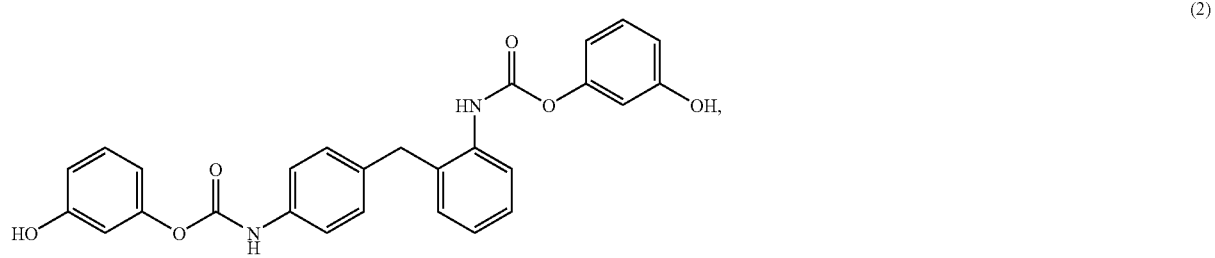

-continued

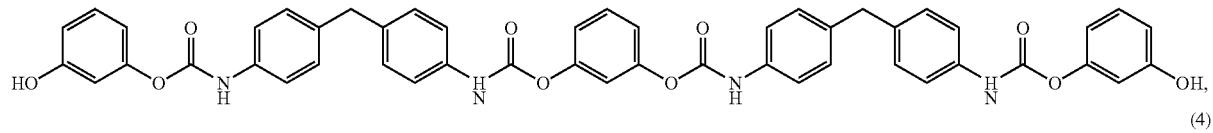

(3)

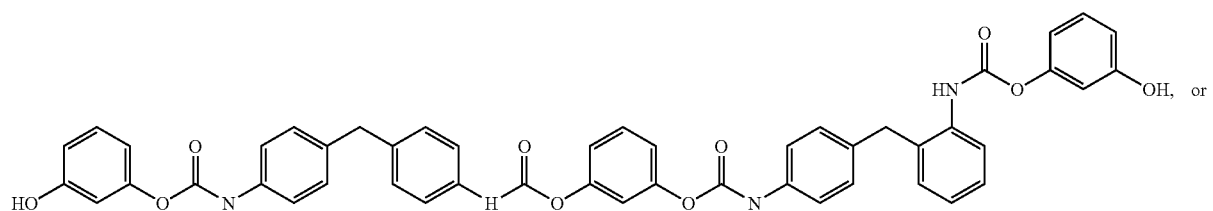

(4)

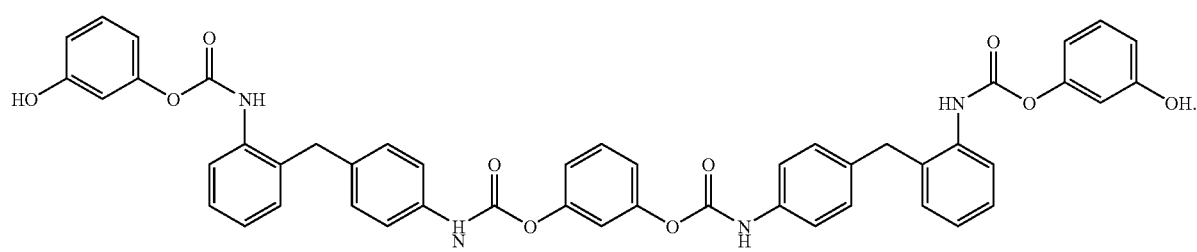

(5)

In some embodiments, the resorcinol-blocked isocyanate composition comprises Compounds (1) and (2). In further embodiments, the resorcinol-blocked isocyanate composition comprises Compound (4). In further embodiments, the resorcinol-blocked isocyanate composition comprises Compounds (1), (2) and (4). In a particular embodiment, the resorcinol-blocked isocyanate composition comprises Compounds (1), (2), (3), (4) and (5).

Each of Compounds (1)-(5) and Formulae (VIA), (VIB), (VIC), (VIIA), (VIIB), (XIA), (XIB), (XIC), (XIIA) and (XIIB) can be optionally substituted. Some non-limited examples of suitable substituents include alkyl, aryl, alkaryl, cycloalkaryl, aralkyl, alkenyl such as unsubstituted or substituted vinyl and allyl, alkynyl, unsubstituted or substituted methacrylate, unsubstituted or substituted acrylate, silyl ether, siloxanyl, acyl, carboxy, heterocyclyl, halide, nitro, hydroxy, —N=C=O, —N=C=S or a combination thereof.

When any of $R^1$-$R^{38}$ is hydrogen, a skilled artisan can recognize that such phenolic acidic hydrogen can be functionalized or converted into another chemical group such as acyl, alkyl or alkenyl by known reactions of phenols. For example, each of the phenolic acidic hydrogen can be optionally and independently converted into an alkyl or alkenyl group by reacting with (1) a diazoalkane; (2) an alkyl or alkenyl halide; alkyl or alkenyl sulfate; alkyl or alkenyl sulfite in the presence of a base; or (3) an olefin in the presence of an acid catalyst. Similarly, the phenolic acidic hydrogen can be converted into an acyl group by reacting with an acyl halide or a carboxylic acid anhydride in the presence of a base.

Similarly, each of the above-mentioned phenolic acidic hydrogen can be optionally and independently functionalized or converted into a substituted or unsubstituted methacrylate or acrylate group by reacting the phenolic acidic hydrogen with the epoxy group of an epoxy compound that also comprises a methacrylate or an acrylate group. Some non-limiting examples of suitable epoxy compounds include glycidyl methacrylate, and glycidyl acrylate, both of which can be obtained from a commercial supplier such as Aldrich, Milwaukee, Wis. A possible reaction between the resorcinol-blocked isocyanate of Formula (A) where X is as defined above with glycidyl methacrylate is shown below.

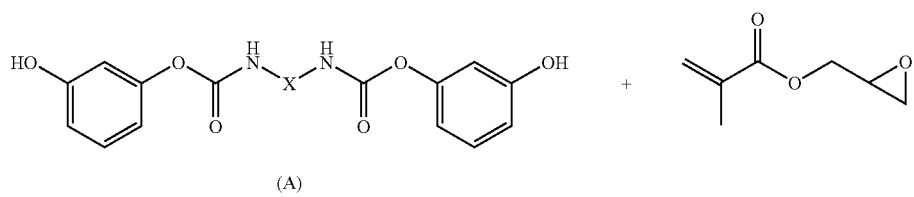

(A)

↓

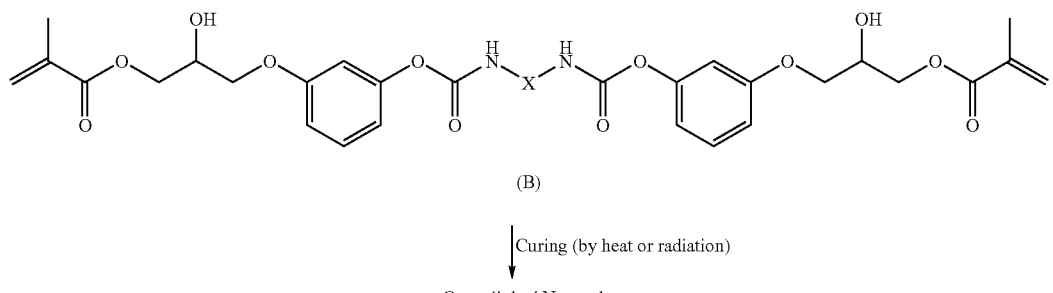

(B)

Curing (by heat or radiation)

Cross-linked Networks

Alternatively, each of the phenolic acidic hydrogen can be optionally and independently converted into a substituted or unsubstituted methacrylate or acrylate group by reacting the phenolic acidic hydrogen with substituted or unsubstituted methacryloyl halide or acryloyl halide. Some non-limiting examples of suitable substituted or unsubstituted methacryloyl halide or acryloyl halide include acryloyl chloride, 3,3-dimethylacryloyl chloride, methacryloyl chloride, crotonoyl chloride, and cinnamoyl chloride, all of which can be obtained from commercial suppliers such as Aldrich, Milwaukee, Wis. A possible reaction between the resorcinol-blocked isocyanate of Formula (A) where X is as defined above with acryloyl chloride is shown below.

Further, each of the above-mentioned phenolic acidic hydrogen can be optionally and independently functionalized or converted into a substituted or unsubstituted alkene by reacting the phenolic acidic hydrogen with the isocyanate of an isocyanate compound that also comprises an alkenyl group. A non-limiting example of suitable isocyanate compound includes 3-isopropenyl-alpha,alpha-dimethylbenzyl isocyanate, which can be obtained from a commercial supplier such as Aldrich, Milwaukee, Wis. A possible reaction between the resorcinol-blocked isocyanate of Formula (A) where X is as defined above with 3-isopropenyl-alpha,alpha-dimethylbenzyl isocyanate is shown below.

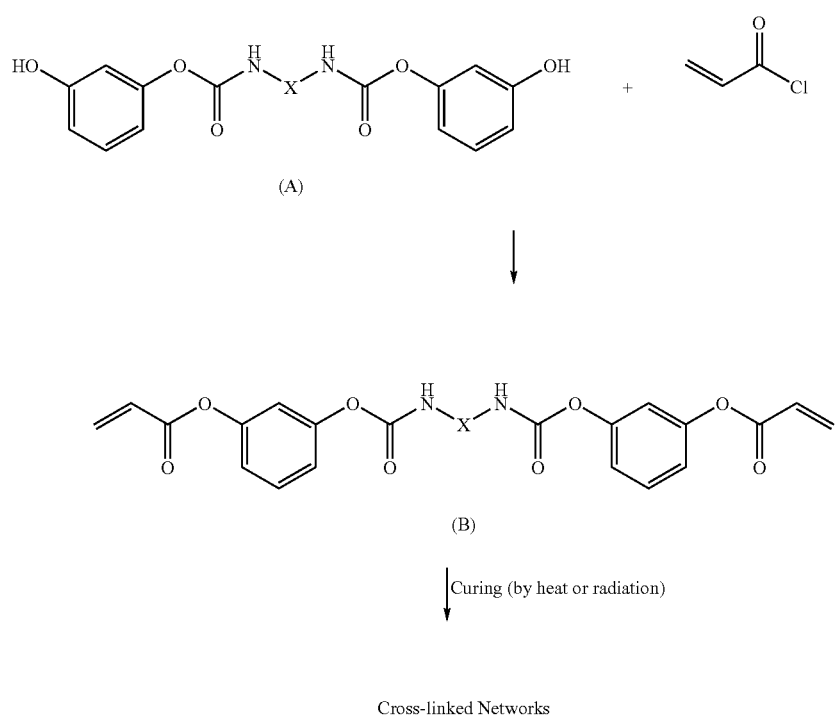

(A)

(B)

Curing (by heat or radiation)

Cross-linked Networks

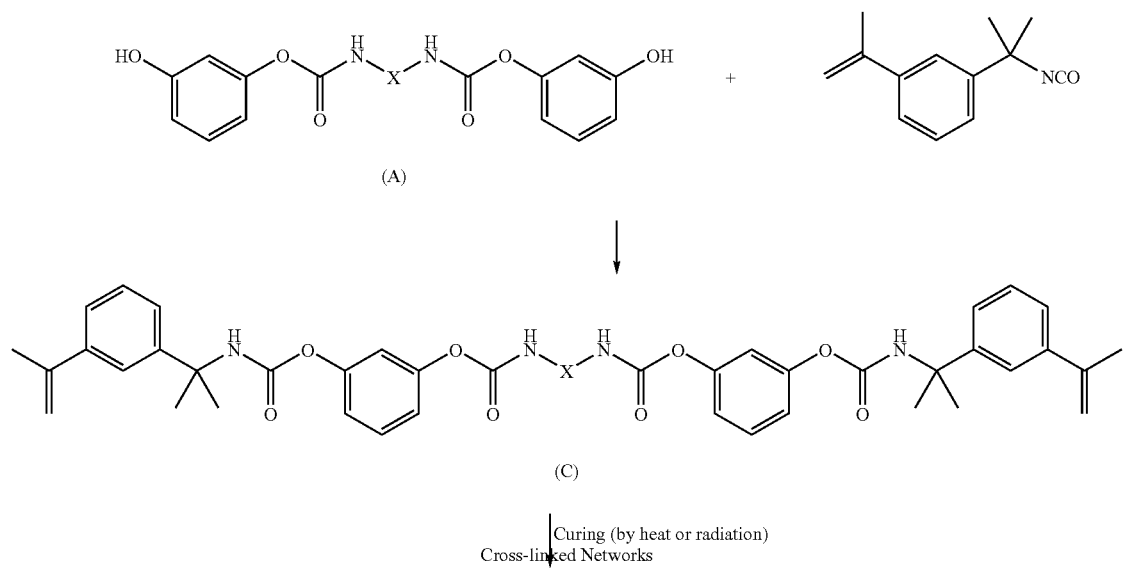

(A)

(C)

Curing (by heat or radiation)

Cross-linked Networks

The above-mentioned functionalized methacrylate, acrylate and alkenyl, compounds such as the compounds represented by Formulae (B), (B') and (C) can be cross-linked by heat or radiation, such as UV light and e-beam, in the presence or absence of an initiator to form a resin or polymeric material that can be used as a binder in various coating formulations. Some non-limiting examples of suitable initiators include peroxides such as acyl peroxides (e.g., acetyl and benzoyl peroxides), alkyl peroxides (e.g., t-butyl peroxide and cumyl peroxide), hydroperoxides (e.g., t-butyl hydroperoxide and cumyl hydroperoxide), peresters (e.g., t-butyl perbenzoate), azo compounds (e.g., 2,2'-azobisisobutyronitrile), disulfides, tetrazenes and combinations thereof. Further, Formula (B) can be cured by any of to the diisocyanates or polyisocyantes disclosed herein. Optionally, the coating formulations may comprise one or more suitable additives such as solvents, fillers, rheology modifiers, thickeners, surfactants, wetting agents, cross-linking agents, coupling agents, colorants, lubricants, leveling agents, antioxidants, UV stabilizers, plasticizers, and the like.

Further, each of the above-mentioned phenolic acidic hydrogen can be optionally and independently functionalized or converted into an alkyl, aryl, aralkyl, vinyl, siloxanyl, or silyl ether group by reacting the phenolic acidic hydrogen with the epoxy group of an epoxy compound that also comprises an alkyl, aryl, aralkyl, vinyl, siloxanyl, or silyl ether group respectively. These functionalized alkyl, aryl, aralkyl, vinyl, siloxanyl, or silyl ether compounds can be used in various coating applications. The chemistry of the phenolic acidic hydrogen is described in Zvi Rappoport, "The Chemistry of Phenols," John Wiley & Sons, pp. 199-258, 605-660 and 1015-1106 (2003), which is incorporated herein by reference in its entirety. A possible reaction between the resorcinol-blocked isocyanate (A) where X is as defined above with an epoxy compound (D) where R is alkyl, aryl, aralkyl, vinyl, siloxanyl, or silyl ether is shown below.

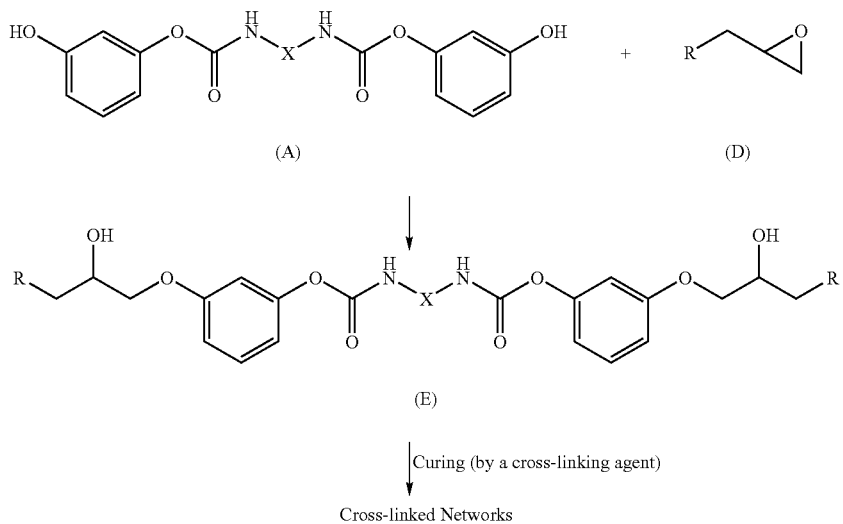

(A)        (D)

(E)

Curing (by a cross-linking agent)

Cross-linked Networks

The above-mentioned functionalized alkyl, aryl, aralkyl, vinyl, siloxanyl, and silyl ether compounds such as the compounds represented by Formula (E) can be cross-linked by a curing agent, such as the diisocyanates and polyisocyantes disclosed herein, to form a resin or polymeric material that can be used as a binder in various coating formulations. Optionally, the coating formulations may comprise one or more suitable additives such as solvents, fillers, rheology modifiers, thickeners, surfactants, wetting agents, cross-linking agents, coupling agents, colorants, lubricants, leveling agents, antioxidants, UV stabilizers, plasticizers, and the like.

The resorcinol-blocked isocyanate composition can be used as a methylene acceptor in rubber composition formulations. Any rubber or rubber material, such as a natural rubber, a synthetic rubber or a combination thereof, can be used for the rubber composition disclosed herein. Non-limiting examples of suitable synthetic rubber polymers include the butadiene polymers such as polybutadiene, isobutylene rubber (butyl rubber), ethylene-propylene rubber (EPDM), neoprene (polychloroprene), polyisoprene, copolymers of 1,3-butadiene or isoprene with monomers such as styrene, acrylonitrile and methyl methacrylate as well as ethylene/propylene/diene monomer (EPDM) and in particular ethylene/propylene/dicyclopentadiene terpolymers. Non-limiting examples of suitable butadiene polymers include those polymers having rubber-like properties, prepared by polymerizing butadiene alone or with one or more other polymerizable ethylenically unsaturated compounds, such as styrene, methylstyrene, methyl isopropenyl ketone and acrylonitrile. The butadiene may be present in the mixture in an amount of at least 40% of the total polymerizable material.

Any suitable methylene donor known in the art can be optionally added to the rubber composition. Generally, methylene donors are capable of generating formaldehyde by heating during the vulcanization of the rubber material. Non-limiting examples of suitable methylene donors include hexamethylenetetramine (HMTA), di- to hexamethylolmelamines or completely or partially etherified or esterified derivatives thereof, for example, hexamethoxy methylmelamine (HMMM), oxazolidine derivatives, N-methyl-1,3,5-dioxazine and the like.

In addition to the resorcinol-blocked isocyanate disclosed herein being used as a first methylene acceptor in the rubber composition, a second suitable methylene acceptor that can react with formaldehyde can be optionally added to the rubber composition. Some non-limiting examples of suitable second methylene acceptors include resorcinol resin-blocked isocyanate compositions; various resorcinol-formaldehyde resins such as PENACOLITE® resins B-16 and B-1A; PENACOLITE® resins B-18-S, B-19-S and B-19-M; and PENACOLITE® resins B-20-S and B-21-S. All of the above-mentioned PENACOLITE® resins are commercially available from INDSPEC Chemical Corporation, Pittsburgh, Pa. In some embodiments, the methylene acceptor is the resorcinol-blocked isocyanate composition disclosed herein, without the second methylene acceptor. In other embodiments, the second methylene acceptor is present and may be PENACOLITE® B-20-S. In further embodiments, the first methylene acceptor is incorporated into the rubber component in an amount from about 1 to 5 parts by weight based on 100 parts by weight of the rubber component (i.e., 1 to 5 phr).

Generally, the weight ratio of methylene acceptor to methylene donor is from about 1:10 to 10:1, more preferably 1:3 to 3:1. When the methylene donor is HMTA, the weight ratio is preferably at least about 2:1.

The rubber composition may include a cross-linking or vulcanizing agent such as sulfur. Examples of suitable sulfur vulcanizing agents include elemental sulfur or sulfur donating vulcanizing agents. In some embodiments, the sulfur vulcanizing agent is elemental sulfur. Other cross-linking agents may also be used.

The rubber composition may also include one or more additives such as carbon black, zinc oxide, silica, antioxidants, stearates, accelerators, oils, adhesion promoters, cobalt salts, stearic acid, fillers, plasticizers, waxes, processing oils, retarders, antiozonants and the like. Accelerators can be used to control the time and/or temperature required for the vulcanization and to improve the properties of the vulcanizate. Suitable accelerators include, but are not limited to, amines, disulfides, guanidines, thioureas, thiazoles, thiurams, sulfenamides, dithicarbonates and zanthates. In some embodiments, the primary accelerator is a sulfenamide such as N,N-dicylohexyl-2-benzenethiazole sulfenamide. Any cobalt compound that can promote the adhesion of rubber to metal, such as stainless steel, may be used. Suitable cobalt compounds include, but are not limited to, cobalt salts of fatty acids and other carboxylic acids, such as stearic acid, palmitic, oleic, linoleic, and the like; cobalt salts of aliphatic or alicyclic carbocylic acids having 6 to 30 carbon atoms such as cobalt neodecanoate; cobalt salts of aromatic carbocylic acids such as cobalt naphthenate; cobalt halides such as cobalt chloride; and organo-cobalt-boron complexes such as MANOBOND® 680C from OM Group, Inc., Cleveland, Ohio.

The rubber composition can be prepared by mixing a rubber material, carbon black, zinc oxide, lubricants and a methylene acceptor in a Banbury mixer at a temperature of about 150° C. The resulting masterbatch is then compounded on a standard 2-roll rubber mill with at least a sulfur accelerator and a methylene donor. Next, the rubber composition can be shaped and cured. Other methods of preparing of rubber compositions and their formulations are described in U.S. Pat. Nos. 6,875,807; 6,605,670; 6,541,551; 6,472,457; 5,945,500; and 5,936,056; all of which are incorporated herein by reference.

In some embodiments, the rubber composition is a vulcanizable rubber composition comprising (a) a rubber material, (b) a methylene donor compound which generates formaldehyde by heating; (c) a methylene acceptor which is or comprises the resorcinol-blocked isocyanate composition disclosed herein; and (d) a cross-linking or vulcanizing agent. In further embodiments, the rubber material is natural rubber, styrene-butadiene rubber, butadiene rubber, isoprene rubber, acrylonitrile-butadiene rubber, chloroprene rubber, butyl rubber, halogenated butyl rubber, ethylene-propylene-diene monomer (EPDM) rubber, or a mixture thereof.

In some embodiments, the vulcanizable rubber composition further comprises a rubber reinforcing material. Any rubber reinforcing material that can strengthen rubber materials can be used, including, but not limited to, polyesters, polyamides (e.g., nylons and aramid), polyvinyl alcohol, carbon, glass, steel (brass, zinc or bronze plated), polybenzoxazole, rayon, and other organic or inorganic compositions. These rubber reinforcing materials may be in the form of filaments, fibers, cords, or fabrics. In some embodiments, the rubber reinforcing material can be a steel cord coated by brass, zinc, bronze or a combination thereof.

While not necessary, the rubber reinforcing material can be coated with an adhesive composition before it is combined with an uncured rubber composition. Any adhesive composition that can enhance the adhesion between the reinforcing material and the cured rubber component can be used. For examples, certain suitable adhesive compositions for enhancing the adhesion between rubber materials and rubber reinforcing materials are disclosed in U.S. Pat. Nos. 6,416,869; 6,261,638; 5,789,080; 5,126,501; 4,588,645; 4,441,946; 4,236,564; 4,051,281; 4,052,524; and 4,333,787, which are incorporated herein by reference in their entirety. These adhesive compositions can be used according to the methods taught therein, with or without modifications.

Fabricated articles can be made from the vulcanizable rubber composition disclosed herein. Non-limiting examples of the fabricated article include tires, belts such as power transmission belts, conveyor belts and V-belts, hoses such as pneumatic and hydraulic hoses, printing rolls, rubber shoe heels, rubber shoe soles, automobile floor mats, truck mud flaps and ball mill liners.

In some embodiments, the fabricated rubber article can be prepared according to the following method which comprises the steps of (1) obtaining a vulcanizable rubber composition as described above mixed with a cross-linking agent; (2) embedding in the vulcanizable rubber composition a rubber reinforcing material; and (3) effecting cross-linking of the rubber composition, wherein the reinforcing material is embedded in the vulcanizable rubber composition before the cross-linking.

In many instances, the dynamic properties and/or adhesive properties of the vulcanizable rubber compositions can be improved by replacing a conventional methylene acceptor with the resorcinol-blocked isocyanate composition disclosed herein. In some embodiments, the storage modulus (G') of the vulcanizable rubber composition having the resorcinol-blocked isocyanate composition as the methylene acceptor is at least about 0.5%, about 1%, about 2.5%, about 5%, about 7.5%, about 10%, about 15%, about 20%, about 25%, about 30%, about 40% or about 50% higher than those of the corresponding vulcanizable rubber composition where another methylene acceptor is used. The dynamic properties of the vulcanizable rubber compositions can be measured according to ASTM D5992 or by using a TA Instruments ARES-RDA at different temperatures such as 23° C. and 60° C., a frequency of 1.0 Hz, and different strains such as 0.2%, 2.0%, 5.0% and 9.8% strain. Rectangular specimen 18 mm long, 12 mm wide and 4 mm thick were used for the measurement.

The resorcinol-blocked isocyanate composition disclosed herein can also be used to prepare various dipping formulations for treating rubber reinforcing materials. In some embodiments, the dipping formulation comprises the resorcinol-blocked isocyanate composition without a resorcinol-formaldehyde-latex. In other embodiments, the dipping formulation is a single dip (i.e., single step) or double dip (i.e., double step) formulation comprising a resorcinol-formaldehyde-latex (RFL) for various industrial applications. For example, either the single dip or double dipping RFL formulation can be used to treat rubber reinforcing materials in rubber compositions comprising a rubber material and at least one of the rubber reinforcing materials. Any rubber reinforcing material known in the art can be used, including, but not limited to, polyesters, polyamides (e.g., nylons and aramid), polyvinyl alcohol, carbon, glass, polybenzoxazole, rayon, and other organic or inorganic compositions. These rubber reinforcing materials may be in the form of filaments, fibers, cords, or fabrics.

The adhesive properties provided by a single or double dipping formulation, such as the H-pull adhesion properties, can be improved by using the resorcinol-blocked isocyanate composition disclosed herein in the formulation. In a single dipping formulation, the resorcinol-blocked isocyanate of the invention is used as an additive to the standard RFL formulation. Optionally, the resorcinol-blocked isocyanate can be used as the sole resorcinol source in the RFL formulation. Furthermore, the resorcinol-blocked isocyanate can be used as the sole ingredient in the dipping formulation In a double dipping formulation, the resorcinol-blocked isocyanate is used in the first dip, often with other materials such as a solvent, a thickener, an epoxy, and the like, followed by a conventional RFL formulation as the second dip. In some applications, such as in power transmission belts, the resorcinol-blocked isocyanate dip is the only treatment; the second, RFL treatment is not used. The H-pull adhesion properties, such as % of rubber coverage, peak load, energy required for the test, and % of broken cords, can be measured according to ASTM D 4776. The samples can be vulcanized and tested for unaged condition, steam-aged condition and/or humidity-aged condition. In resorcinol-formaldehyde-latex (RFL) formulations, the resorcinol-blocked isocyanate composition can replace phenol-blocked or caprolactam-blocked isocyanates either partially or completely. Also, if the resorcinol-blocked isocyanate composition partially replaces an R/F resin in the formulation, the flexibility of the formulation may be improved due to the replacement of some of the rigid methylene bridged structures with flexible longer chain bridged resorcinol.

In some single dip methods, an aqueous alkaline dipping formulation can be made by mixing a resin solution, such as a resorcinolic novolak resin solution, with sufficient water to reduce the concentration of resin solids to less than about 10 weight %. The pH adjustment can be made by the addition of an aqueous caustic solution. An alkaline substance, such as sodium hydroxide or ammonium hydroxide can be added to the dip to adjust the pH to about 7.0 to about 12.0. After adjusting the solution pH, an aqueous formaldehyde solution may be added. A synthetic rubber latex can then be added to the resin solution. The RFL dip thus prepared can be ready for an immediate use, but dips generally show better results if they are aged for about 16 to 24 hours at room temperature prior to use. In the preparation of a single dipping formulation, the resorcinol-blocked isocyanate composition disclosed herein can be used as an adhesion promoter. Optionally, other adhesion promoters, such as polyepoxide compounds, other blocked isocyanate compounds or ethylene-urea compounds, may be employed. Generally, the adhesion promoters in the RFL may improve the bonding of the rubber material to the rubber reinforcing material by surface diffusion or penetration, or by chemical and physical interactions.

The rubber latex used in the dip may be a natural rubber latex, a styrene-butadiene rubber latex, an acrylonitrile-butadiene rubber latex, a chloroprene rubber latex and a vinylpyridine-styrene-butadiene rubber latex. These latices can be used alone or as mixtures. There is no limitation on the type of rubber latex use in the dipping formulation. In general, vinylpyridine-styrene-butadiene copolymer latices are preferably used as the main rubber component of the rubber latex.

In some single dip treatments, no resorcinol-formaldehyde-latex is used. The single dipping formulation may contain only the resorcinol-blocked isocyanate disclosed herein and optionally a solvent. Further, this type of single dipping formulation may optionally contain an epoxy-containing compound, a thickener, an antifoam or one or more other additives. Generally, the adhesion of rubber reinforcing materials such as cords and fabrics to rubber materials may be enhanced by dipping the rubber reinforcing materials in such a single dipping formulation without a resorcinol-formaldehyde-latex.

In the double dip method, the rubber reinforcing materials are treated with the first dip solution comprising the resorcinol-blocked isocyanate composition disclosed herein. Optionally, other adhesion promoters, such as polyepoxide compounds, other blocked isocyanate compounds or ethylene-urea compounds, may be employed. The polyepoxide compounds suitable for use generally comprise molecules containing one or more epoxy groups and may include epoxy compounds made from glycerol, pentaerythritol, sorbitol, ethylene glycol, polyethylene glycol and resorcinol. In some embodiments, the polyepoxide compounds are the polyepoxides of polyalcohols. In other embodiments, the blocked isocyanate is selected from lactams, phenols and oximes blocked isocyanates comprising toluene diisocyanate, metaphenylene diisocyanate, diphenylmethane diisocyanate, triphenylmethane triisocyanate and hexamethylene diisocyanate. This first dip treatment generally can activate the fiber surface to enhance the interaction with the second dip solution, i.e. the RFL formulation. The further use of the resorcinol-blocked isocyanate composition disclosed herein in the RFL of a double dipping formulation can further improve the adhesion of the rubber reinforcing material to rubber compounds.

The single dip or double dipping formulation can be used for various applications. For example, they can be used to bond polyester tire cords to the rubber material with improved results than the conventional formulation.

In one process for adhering polyester cords to rubber compounds, a conventional dipping machine is employed whereby the cords are continuously drawn through a dip bath containing the one step dipping formulation prepared using the resin made in accordance with embodiments of the invention. The excess dip is removed by blowing the cord with air jets and then dried the cord in an oven set at 170° C. for 120 seconds. Then the cords are cured at 230° C. for a sufficient time necessary for the penetration of the dip into the polyester cord. An acceptable cure time of about 60 seconds has been found to be suitable.

In the process of testing the successful bonding of polyester cords to the rubber material, the adhesive treated cords are embedded in a formulated and uncured compound and then the rubber compound is vulcanized for a sufficient time and pressure to promote good adhesion. The H-pull adhesion test has been employed to determine the static adhesion of textile tire cords to the rubber material. This test is specified as ASTM D-4776 method and is used for testing purposes.

Though the adhesive containing polyester reinforcing fibers or cords can be adhered to a rubber material such as vulcanizable compounds of natural rubber, polybutadiene rubber and rubbery butadiene-styrene copolymer, it is understood that polyester reinforcing fibers or cords can also be adhered to other vulcanizable rubbery materials from the group comprising nitrile rubbers, chloroprene rubbers, polyisoprenes, acrylic rubbers, ethylene-propylene-diene monomer (EPDM) rubber and isoprene-acrylonitrile rubbers. These rubbers prior to curing can be mixed with the usual compounding ingredients comprising sulfur, stearic acid, zinc oxide, accelerators, antioxidants, antiozonants, and other curatives.

Polyester fibers, yarns, filaments, cords or fabric coated with the dipping formulations comprising the resorcinol-blocked isocyanate composition disclosed herein can be used in the manufacture of radial, bias, or belted-bias passenger tires, truck tires, motorcycle or bicycle tires, off-the-road tires, airplane tires, transmission belts, V-belts, conveyer belts, hose, and gaskets.

In addition to their use as ingredients in rubber compounding and fabric dipping formulations, the resorcinol-blocked isocyanate composition disclosed herein could be used in various curing reactions involving the phenolic hydroxyl groups, particularly with a reactive ring group such as epoxy ring. Non-limiting examples of suitable reactive ring groups include heterocyclic ring groups that have a higher strain energy than their corresponding open-ring structures. The conventional definition of strain energy is that it represents the difference in energy between the actual molecule and a completely strain-free molecule of the same constitution. More information about the origin of strain energy can be found in the article by Wiberg et al., "A Theoretical Analysis of Hydrocarbon Properties: II Additivity of Group Properties and the Origin of Strain Energy," *J. Am. Chem. Soc.* 109, 985 (1987), which is incorporated herein by reference. The heterocyclic ring group may have 3, 4, 5, 7, 8, 9, 10, 11, or 12 members, in further embodiments 3, 4, 5, 7, or 8 members, in some embodiments 3, 4, or 8 members, and in additional embodiments 3 or 4 members. Non-limiting examples of such heterocyclic ring are cyclic ethers (e.g., epoxides and oxetane), cyclic amines (e.g., aziridine), cyclic sulfides (e.g., thiirane), cyclic amides (e.g., 2-azetidinone, 2-pyrrolidone, 2-piperidone, caprolactam, enantholactam, and capryllactam), N-carboxy-α-amino acid anhydrides, lactones, and cyclosiloxanes. The chemistry of the above heterocyclic rings is described in George Odian, "Principle of Polymerization," second edition, Chapter 7, p. 508-552 (1981), which is incorporated herein by reference.

In additional examples, the reactive ring may be a 5 or 7-membered ring comprising a —COO— group or a —CONR— group, such as butyrolactone, N-methylbutyrolactam, N-methylcaprolactam, and caprolactone.

In some embodiments, the non-functionalized or functionalized resorcinol-blocked isocyanate composition prepared from a diisocyanate or polyisocyanate compound can be used as a masked diisocyanate or polyisocyanate compound. The masked diisocyanate or polyisocyanate compound can react upon heating with a difunctional compound such as a diol, a dithiol, a diamine, a dicarboxylic acid, a hydroxylamine, an amino acid, a hydroxyl acid, a thiol acid, a hydroxythiol, or a thioamine to form a polymeric material or article. For example, when a diol or diamine is used, a polyurethane or a polyurea material may form respectively. Non-limiting examples of suitable dithiol are 3,6-dioxa-1,8-octanedithiol, erythro-1,4-dimercapto-2,3-butanediol, (±)-threo-1,4-dimercapto-2,3-butanediol, 4,4'-thiobisbenzenethiol, 1,4-benzenedithiol, 1,3-benzenedithiol, sulfonyl-bis(benzenethiol), 2,5-dimecapto-1,3,4-thiadiazole, 1,2-ethanedithiol, 1,3-propanedithiol, 1,4-butanedithiol, 2,3-butanedithiol, 1,5-pentanedithiol, and 1,6-hexanedithiol. Non-limiting examples of suitable diols are 2,2'-bi-7-naphtol, 1,4-dihydroxybenzene, 1,3-dihydroxybenzene, 10,10-bis(4-hydroxyphenyl)anthrone, 4,4'-sulfonyldiphenol, bisphenol, 4,4'-(9-fluorenylidene)diphenol, 1,10-decanediol, 1,5-pentanediol, diethylene glycol, 4,4'-(9-fluorenylidene)-bis(2-phenoxyethanol), bis(2-hydroxyethyl) terephthalate, bis[4-(2-hydroxyethoxy)phenyl]sulfone, hydroquinone-bis-(2-hydroxyethyl)ether, and bis(2-hydroxyethyl)piperazine. Non-limiting examples of suitable diamine are diaminoarenes such as 1,4-phenylenediamine, 4,4-diaminobenzophenone and 4,4-diaminodiphenyl sulfone, and diaminoalkanes such as 1,2-ethanediamine and 1,4-butanediamine, dibenzo[b,d]furan-2,7-diamine, and 3,7-diamino-2(4),8-dimethyldibenzothiophene-5,5-dioxide. Non-limiting examples of suitable dicarboxylic acid are phthalic acid, terephthalic acid, adipic acid, and 4,4'-biphenyldicarboxylic acid. Non-limiting examples of suitable hydroxylamine are p aminophenol and fluoresceinamine. Non-limiting examples of suitable amino acid are 4-aminobutyric acid, phenylalanine, and 4-aminobenzoic acid. Non-limiting examples of suitable hydroxyl acid are salicylic acid, 4-hydroxybutyric acid, and 4-hydroxybenzoic acid. Non-limiting examples of suitable hydroxythiol are monothiohydroquinone and 4-mercapto-1-butanol. Non-limiting example of suitable thioamine is p-aminobenzenethiol. Non-limiting examples of suitable thiol acid are 4-mercaptobenzoic acid and 4-mercaptobutyric acid. Almost all of the above bridging compounds are available commercially from Aldrich Chemicals and other chemical suppliers.

Further, the functionalized resorcinol-blocked isocyanate composition may contain useful functional groups such as hydroxyl, carboxyl, amine, epoxy, that may be used for other applications such as coatings and composites. The functionalized methacrylate or acrylate, alkenyl, alkyl, aryl, vinyl, aralkyl, siloxanyl and silyl ether compounds such as compounds of Formulae (B), (B'), (C), and (E) mentioned previously may also be cross-linked to form a resin or polymeric materials suitable for various coating applications.

The following examples are presented to exemplify embodiments of the invention. All numerical values are approximate. When numerical ranges are given, it should be understood that embodiments outside the stated ranges may still fall within the scope of the invention. Specific details described in each example should not be construed as necessary features of the invention.

EXAMPLES

Example 1

SCHEME A

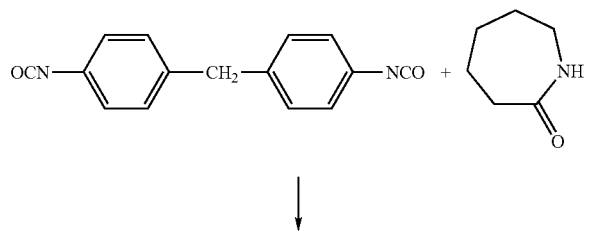

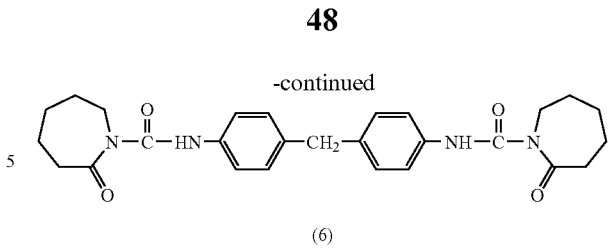

(6)

A mixture of 24.9 grams (0.22 mole) of caprolactam and 45 ml of dry toluene was charged into a 250 ml four-necked round bottomed flask equipped with a mechanical stirrer, a thermometer, an addition funnel and a reflux condenser. After purging the flask with nitrogen gas, the contents of the flask were heated to about 60° C. Then, an MDI solution, prepared by dissolving 25 grams (0.1 mole) of 4,4'-diphenylmethane diisocyanate (4,4'-MDI) in 38.9 grams of dry toluene, was added slowly from the addition funnel into the flask for a period of about 30 to 60 minutes at 60 to 75° C. with good stirring. After the addition of the MDI solution, the stirring of the reaction mixture was continued at about 60 to 80° C. for an additional period of 4 to 6 hours to complete the reaction. Then the reaction mixture was cooled slowly with continued stirring. The fine white precipitate that separated out from the reaction mixture was filtered and washed with fresh toluene first and then several times with methanol. Finally, the product was dried in a vacuum oven at 60 to 70° C. The yield of Example 1 was 42 grams.

Example 1 was characterized with FT-IR and $^1$H- and $^{13}$C-NMR, all of which confirmed the structure of caprolactam-blocked 4,4'-diphenylmethane diisocyanate [i.e., Compound (6)]. No extraneous organic components, including unreacted caprolactam or NCO groups, were detected in Example 1.

A DSC analysis of Example 1 showed a very sharp peak in the 170 to 190° C. range with an onset temperature of 180° C. and peak temperature of 183° C. (see FIG. 1). The DSC characteristics of Example 1 are similar to those of a dried sample of GRILBOND® IL-6 (a 50% aqueous dispersion of a caprolactam-blocked 4,4'-MDI available from EMS-CHEMIE (North America) Inc., Sumter, S.C.).

Example 2

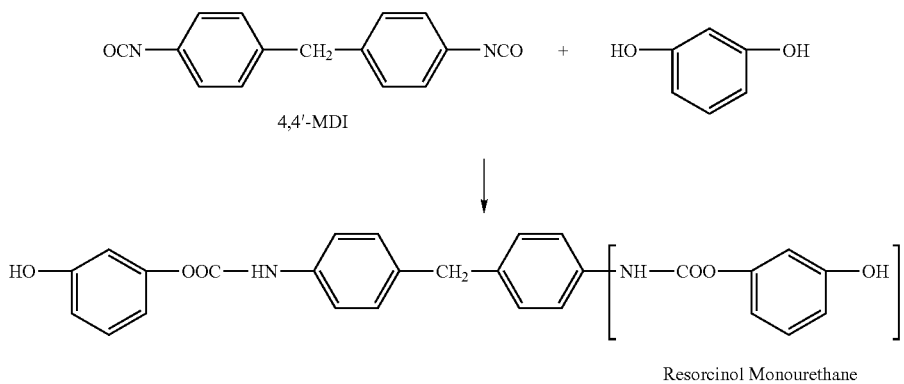

Resorcinol Monourethane (1)

+

-continued

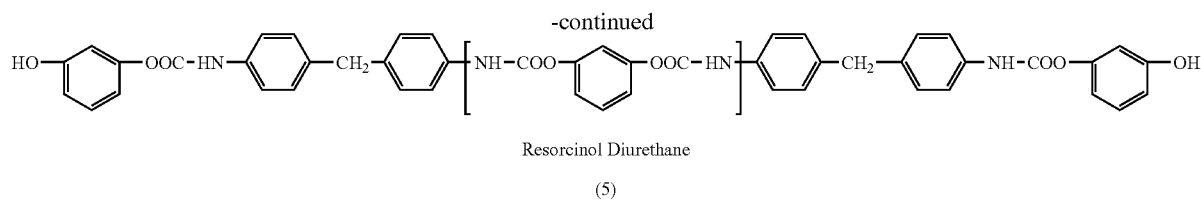

Resorcinol Diurethane (5)

A mixture of 20.6 grams (0.19 mole) of resorcinol, 1.5 grams of AEROSOL® OT (sodium dioctyl sulfosuccinate, 75% concentration, obtained from Cytec Industries Inc., Stamford, Conn.), 1.5 grams of 10% sodium hydroxide solution and 100 ml of distilled water was charged into a 250 ml four-necked round bottomed flask equipped with a mechanical stirrer, a thermometer, an addition funnel and a reflux condenser. The contents of the flask were heated to 40 to 45° C. Separately, an MDI solution of 4,4'-diphenylmethane diisocyanate (4,4'-MDI; 10 gm, 0.04 mole) in 10 gm of methyl ethyl ketone (MEK) was prepared. The MDI solution was added quickly into the reaction flask with good agitation at about 40 to 45° C. After the addition, the reaction mixture was stirred at 25 to 45° C. for an additional period of about 3 hours to form suspended solids. The solids were filtered, washed several times with warm water, and then dried in a vacuum oven at 80° C. The yield of Example 2 was 16.7 grams.

Example 2 was characterized by ET-IR and $^1$H-NMR. The following structures listed in Table 1 were identified and their relative amounts were measured semi-quantitatively by $^1$H-NMR.

TABLE 1

| Structure | Mole Ratio |
| --- | --- |
| Total MDI structures | 35 |
| Resorcinolic diurethanes | 6 |
| Resorcinolic monourethanes | 59 |
| Unreacted resorcinol | Trace* |

Note:
*Free resorcinol is detected, but is too low in concentration to measure. The sample exhibits infrared absorptions as expected for a resorcinolic urethane.

The data in Table 1 indicated that the reaction between resorcinol and 4,4'-MDI forms Example 2 which may comprise a mixture of at least Compounds (1) and (5) in Scheme B above. Both Compounds (1) and (5) have resorcinolic urethane groups.

A DSC analysis of Example 2 showed a sharp peak in the 170 to 210° C. temperature range with an onset at 197° C. and peak at 201° C. (see FIG. 1). This analysis was performed in the presence of nitrogen atmosphere and at a heating rate of 10° C./minute Example 3

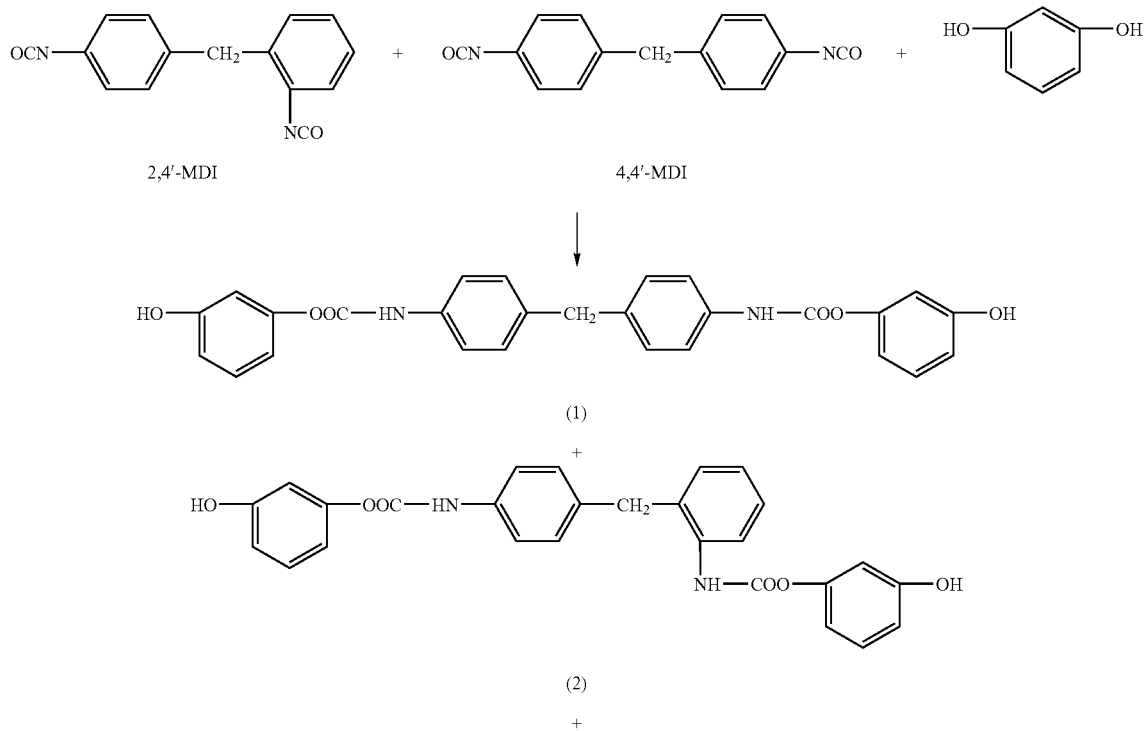

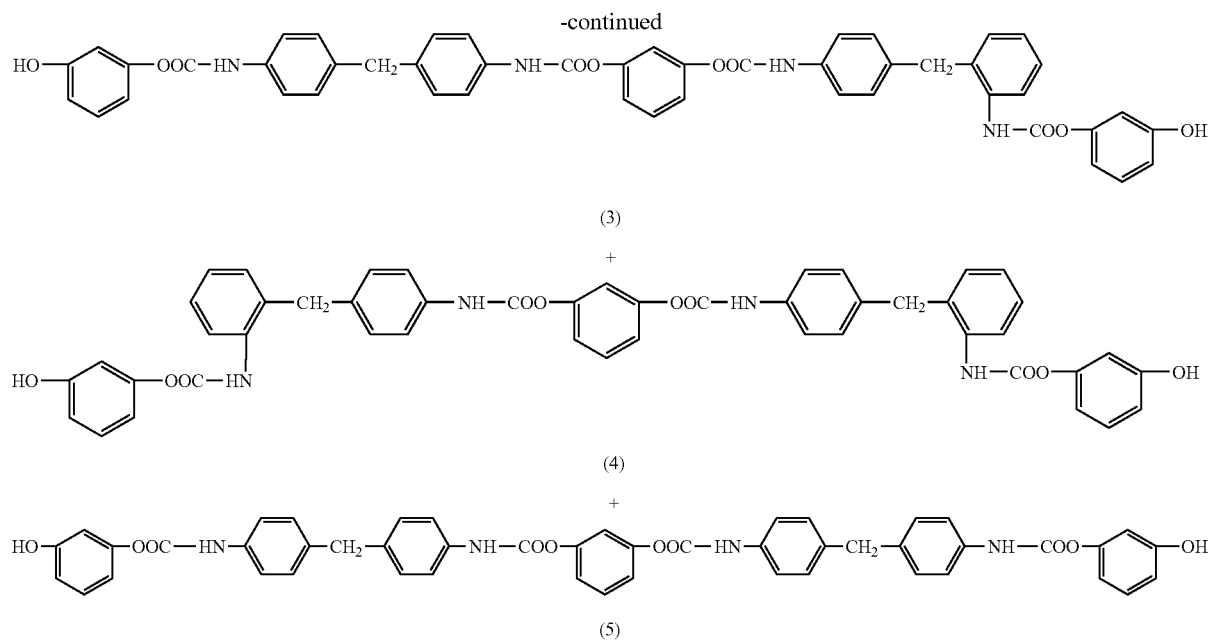

(3)

(4)

(5)

A mixture of resorcinol (0.8 mole, 88 grams) and 3-methyl-1-phenyl-2-phospholene-1-oxide (catalyst, 0.57 gram) was charged into a 500 ml four-necked glass reactor equipped with a mechanical stirrer, a thermometer, an addition funnel and a reflux condenser connected to a $CaCl_2$ guard tube. The reactor was then purged with nitrogen. After the reaction mixture was heated to about 120 to 125° C. to melt the resorcinol, 100 grams (0.4 mole) of MONDUR® ML (a mixture of 2,4'- and 4,4'-diphenylmethane diisocyanate obtained from Bayer Corporation, Pittsburgh, Pa.) was added slowly into the molten resorcinol with good stirring over a period of about 1 to 2 hours at 130 to 160° C. At the end of MONDUR® ML addition, the reaction mixture appeared as a viscous clear orange solution. Stirring and heating were continued for an additional period of about 1 to 3 hours to complete the reaction between resorcinol and MONDUR® ML. Finally, the material was poured onto a tray and cooled. The final product appeared as a yellow colored brittle resin, which was then crushed into a yellow powder. The yield of Example 3 was 186.5 grams.

Example 3 was characterized by FT-IR and $^1$H-NMR. The following structures listed in Table 2 were identified and their relative amounts were measured semi-quantitatively by $^1$H-NMR.

TABLE 2

| Structure | Mole Ratio |
|---|---|
| Total MDI structures | 34 |
| Unreacted resorcinol | 16 |
| Resorcinolic monourethanes | 37 |
| Resorcinolic diurethanes | 13 |
| Resorcinol/MDI mole ratio | 1.96 |

The FT-IR analysis indicated no unreacted NCO structure. A single carbonyl absorption is observed at 1718 wavenumbers. Based on the FT-IR and $^1$H-NMR structural characterization, the reaction between resorcinol and MONDUR® ML in the presence of 3-methyl-1-phenyl-2-phospholene-1-oxide yielded Example 3 which may comprise a mixture of at least Compounds (1) to (5) in Scheme C above.

Example 4

A mixture of resorcinol (0.8 mole, 88 grams) and dibutyltin dilaurate (catalyst, 0.088 gram) was charged into a 500 ml four-necked glass reactor equipped with a mechanical stirrer, a thermometer, an addition funnel and a reflux condenser connected to a $CaCl_2$ guard tube. The reactor was then purged with nitrogen. After the reaction mixture was heated to about 120 to 125° C. to melt the resorcinol, 100 grams (0.4 mole) of MONDUR® ML was added slowly into the molten resorcinol with good stirring over a period of about 1 to 2 hours at 130 to 160° C. At the end of the addition, the reaction mixture appeared as a viscous clear orange solution. Stirring and heating were continued for an additional period of about 1 to 3 hours to complete the reaction between resorcinol and MONDUR® ML. Finally, the material was poured onto a tray and cooled. The final product appeared as a yellow colored brittle resin, which was then crushed into a yellow powder. The yield of Example 4 was 185.2 grams.

Example 4 was characterized by FT-IR and $^1$H-NMR. The following structures listed in Table 3 were identified and their relative amounts were measured semi-quantitatively by $^1$H-NMR. The FT-IR analysis indicated no unreacted NCO structures.

TABLE 3

| Structure | Mole Ratio |
|---|---|
| Total MDI structures | 35 |
| Unreacted resorcinol | 15 |
| Resorcinolic monourethanes | 32 |
| Resorcinolic diurethanes | 18 |

Example 5

A mixture of resorcinol (2.0 moles, 220.2 grams) and dibutyltin dilaurate (catalyst, 0.22 gram) was charged into a 500 ml four-necked glass reactor equipped with a mechanical stirrer, a thermometer, an addition funnel and a reflux condenser connected to a $CaCl_2$ guard tube. The reactor was then purged with nitrogen. After the reaction mixture was heated to about 120 to 125° C. to melt the resorcinol, 250 grams (1.0 mole) of MONDUR® ML was added slowly into the molten resorcinol with good stirring over a period of about 1 to 2 hours at 130 to 160° C. At the end of the addition, the reaction mixture appeared as a viscous clear orange solution. Stirring and heating were continued for an additional period of about 1 to 3 hours to complete the reaction between resorcinol and MONDUR® ML. Finally, the material was poured onto a tray and cooled. The final product appeared as a yellow colored brittle resin, which was then crushed into a yellow powder. The yield of Example 5 was 461 grams. The softening point determined by a modified Mettler Softening Point technique showed a value of 111.8° C. for this brittle resin material.

Example 5 was characterized by FT-IR and $^1$H-NMR. The following structures listed in Table 4 were identified and their relative amounts were measured semi-quantitatively by $^1$H-NMR.

TABLE 4

| Structure | Mole Ratio |
| --- | --- |
| Total MDI structures | 34 |
| Unreacted resorcinol | 14 |
| Resorcinolic monourethanes | 38 |
| Resorcinolic diurethanes | 14 |

A Differential Scanning Calorimetric (DSC) analysis of Example 5 was performed in a Perkin Elmer DSC 7 analyzer in the presence of nitrogen atmosphere and at a heating rate of 10° C./minute. The DSC results showed endothermic peaks at 76, 102 and 140° C. in the thermogram. The peak appearing at 76° C. might be due to the presence of unreacted resorcinol in the resorcinol-blocked isocyanate compound.

Example 6

Example 5 was dissolved in 49 grams of N,N-dimethylformamide (DMF). After the DMF solution was added slowly into 450 grams of distilled water for a period of 60 to 90 minutes with good stirring, the slurry was stirred for an additional period of 2 to 4 hours at room temperature. The solids in the slurry were collected by filtration, washed several times with warm water and dried in a vacuum oven at about 65° C. to form Example 6.

Example 6 was characterized $^1$H-NMR. The following structures listed in Table 5 were identified and their relative amounts were measured semi-quantitatively by $^1$H-NMR.

TABLE 5

| Structure | Mole Ratio |
| --- | --- |
| Total MDI structures | 40 |
| Resorcinolic monourethanes | 43 |
| Resorcinolic diurethanes | 17 |
| Unreacted resorcinol | none |

A Differential Scanning Calorimetric (DSC) analysis of Example 6 was performed in a Perkin Elmer DSC 7 analyzer in the presence of nitrogen atmosphere and at a heating rate of 10° C./minute. The DSC analysis of Example 6 showed endothermic peaks at 88, 120 and 155° C.

A thermogravimetric analysis (TGA) was performed in a Perkin Elmer TGA 7 instrument and in the temperature range of between 25 to 500° C. It was done at a heating rate of 10° C./minute and in the presence of nitrogen atmosphere. The TGA results are presented in Table 6 below.

TABLE 6

| Temperature (° C.) | Weight Loss (%) |
| --- | --- |
| 50 | 0.1 |
| 75 | 0.2 |
| 100 | 0.5 |
| 125 | 0.9 |
| 150 | 1.1 |
| 175 | 1.4 |
| 200 | 2.7 |
| 250 | 20.6 |
| 275 | 48.4 |
| 300 | 60.4 |
| 400 | 69.0 |
| 500 | 75.2 |

Example 7

Example 5 was placed in a 150 ml beaker and stirred with about 100 ml of methanol in a warm hot plate to dissolve the unreacted resorcinol present in Example 5. The liquid was decanted and discarded. This process was repeated several times with additional quantities of methanol. Finally, the remained solids was filtered, washed with methanol and dried completely to form Example 7.

Example 7 was characterized by FT-IR, $^1$H-NMR and $^{13}$C-NMR. The following structures listed in Table 7 were identified and their relative amounts were measured semi-quantitatively by $^1$H-NMR. No NCO structure was detected by FT-IR.

TABLE 7

| Structure | Mole Ratio |
| --- | --- |
| Total MDI structures | 44 |
| Resorcinolic diurethanes | 37 |
| Resorcinolic monourethanes | 19 |
| Unreacted resorcinol | none |
| 4,4'-/2,4'-MDI isomer ratio | 35/65 |

A Differential Scanning Calorimetric (DSC) analysis of Example 7 was performed in a Perkin Elmer DSC 7 analyzer in nitrogen atmosphere and at a heating rate of 10° C./minute. The DSC analysis of Example 6 showed broad endothermic peaks appeared in the region of between 150 to 250° C. with three apparent peak maxima appearing at 166, 188 and 196° C. (See FIG. 1).

By comparing the DSC results of Examples 2 and 7 (see FIG. 1), it is believed that the endothermic peak appearing at 196° C. in the DSC curve may be associated with the presence of resorcinolic urethane groups formed with 4,4'-MDI. Similarly, the endothermic peak observed at 166° C. may be associated with the presence of urethane groups formed between resorcinol and 2,4'-MDI. These results strongly suggests that MONDUR® ML-based resorcinol-blocked isocyanate adducts, such as Example 7, may have lower melting and/or unblocking temperatures than resorcinol- or caprolactam-blocked 4,4'-MDI (see FIG. 1).

Melting Temperatures of Phenol-Blocked 4,4'-MDI, And Examples 1, 2 and 7

A summary of the melting temperatures (i.e., possible unblocking temperatures) of different blocked diphenylmethane diisocyanate (MDI) compounds determined by the DSC analysis is shown in Table 8 below.

TABLE 8

Melting Temperatures of Phenol-Blocked 4,4'-MDI, Examples 1, 2 and 7 by DSC.

| Sample | Blocking Agent Used | Diisocyanate Used | DSC Endotherm Temperature (° C., Peak Maximum) |
|---|---|---|---|
| Comp. Example | Phenol* | 4,4'-MDI | 220** |
| Example 1 | Caprolactam | 4,4'-MDI | 183 |
| Example 2 | Resorcinol | 4,4'-MDI | 201 |
| Example 7 | Resorcinol | 2,4'- and 4,4'-MDI | 166, 196 |

Note:
*W. Thompson, et al, Adhesives Age, February 1959, page 30;
**Heating of phenol-blocked MDI in the vicinity of 220° C. regenerated the isocyanate.

The DSC results in Table 8 and FIG. 1 indicate that the major melting temperatures of resorcinol-blocked MDI compounds (such as Example 7) prepared from a mixture of 2,4'- and 4,4'-MDI are lower than the phenol-, resorcinol- and caprolactam-blocked 4,4'-MDI. The multiple melting temperatures observed in such resorcinol-blocked MDI compounds from a mixture of 2,4'- and 4,4'-MDI can provide multiple possible unblocking temperatures that may improve the performance of products or formulations containing these materials.

Example 8

A dispersion of Example 5 was prepared using an attritor (Model # 01-HD obtained from Union Process Corporation, Akron, Ohio). The media (i.e., stainless steel beads having a diameter of ⅛") in a 1400 ml stainless steel tank of the attritor were rapidly stirred using an agitator shaft with arms driven by a variable frequency drive. The stainless steel tank was jacketed to allow for cooling water. The action of the moving media created shear and impact forces on the sample that grind particles of samples into desirable sizes.

Prior to grinding in the attritor, Example 5 appeared initially as large chunks of brittle resin which were ground into a powder less than 10 mesh in size using a mortar and pestle. A wet grind method in water was applied for all tests on the attritor. The procedure used in the grinding process is as follows. First, the stainless steel media was charged into the stainless steel tank and the stirrer was turned on. Next, water was added to the tank. Finally, the powder prepared by the mortar and pestle was added while stirring.

Samples were taken periodically from each run and were analyzed for particle size distribution by laser diffraction using a Microtrac particle size analyzer (Model # 53000). The MV (mean diameter of the volume distribution), 90% less than, and 50% less than values were reported. A Microtrac analysis of the GRILBOND® IL-6 control showed the following results: MV=1.464 μm, 90%<2.537 μm, and 50%<1.260 μm.

The jacket of the stainless steel tank was cooled by running tap water to prevent any overheating of the samples while grinding. The temperature reading of the sample in the tank was about 72° F. The surfactant used was AEROSOL® OT.

The dispersion mixture in the attritor contained 200 grams of Example 5, 350 grams of distilled water, 22.8 grams of AEROSOL® OT surfactant, and 10 drops of AF 9000 silicone antifoam (available from GE Advanced Materials, Wilton, Conn.). The attritor ran for 6 hours at 600 rpm. The final particle size analysis is as follows: MV=3.145 μm, 90%<6.228 μm, 50%<2.422 μm. The final dispersion product appeared as a stiff paste (Example 8).

Example 8 was used in the preparation of single- and double-step RFL dipping formulations and in the evaluation of its performance against GRILBOND® IL-6 (caprolactam-blocked 4,4'-MDI) in improving the adhesion of PET tire cords to rubber compounds.

Example 9

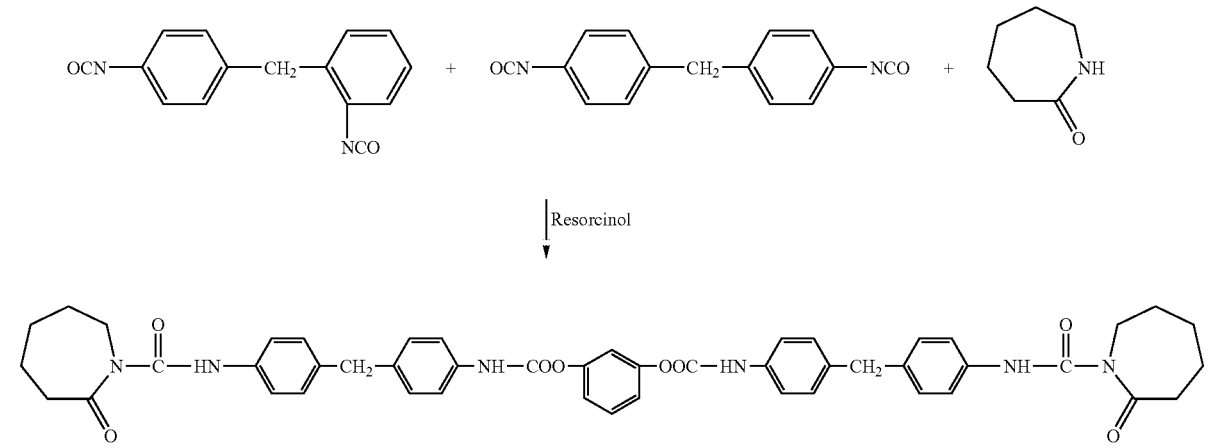

SCHEME D

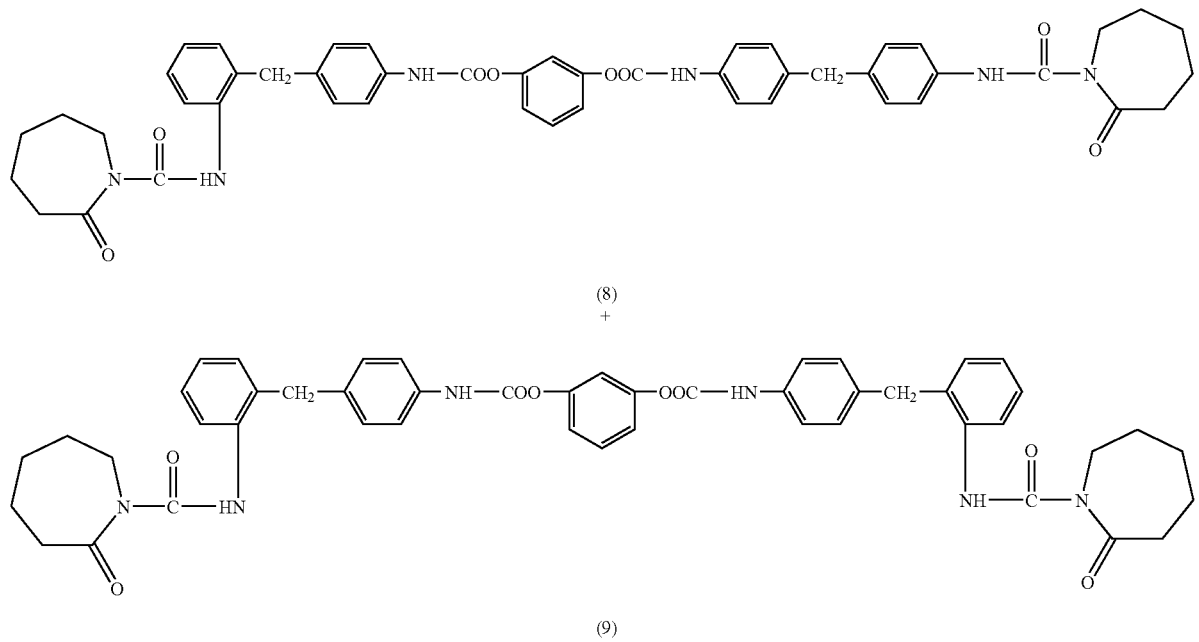

(8)

+

(9)

A mixture of resorcinol (0.4 mole, 44 grams), caprolactam (0.8 mole, 90.6 grams) and dibutyltin dilaurate (catalyst, 0.046 gram) was charged into a 500 ml four-necked glass reactor equipped with a mechanical stirrer, a thermometer, an addition funnel and a reflux condenser connected to a $CaCl_2$ guard tube. The reactor was then purged with nitrogen. After the reaction mixture was heated to about 120 to 125° C. to melt the resorcinol, 200 grams (0.8 mole) of MONDUR® ML was added slowly into the molten resorcinol with good stirring over a period of about 1 to 2 hours at 130 to 160° C. At the end of the addition, the reaction mixture appeared as a viscous clear yellow solution. Stirring and heating were continued for an additional period of about 1 to 3 hours to complete the reaction between resorcinol and MONDUR® ML. Finally, the material was poured onto a tray and cooled. The final product appeared as a light yellow colored brittle resin, which was then crushed into white or faint yellow powder. The yield of Example 9 was 332.5 grams.

Example 9 was characterized by FT-IR, $^1$H-NMR and $^{13}$C-NMR. The following structures listed in Table 9 were identified and their relative amounts were measured semi-quantitatively by $^1$H-NMR (as solutions in DMSO-$d_6$).

TABLE 9

| Structure | Mole Ratio |
|---|---|
| Total MDI structures | 40 |
| Total Reacted Caprolactam | 35 |
| Unreacted Caprolactam | 4 |
| Unreacted resorcinol | <1 |
| Total Resorcinolic Monourethanes & Diurethanes | 10 |
| Unassigned MDI structures | 10 |

Example 9 exhibited infrared absorptions (FT-IR) indicative of aromatic urethanes as the major structural entities. Further, Example 9 exhibited three carbonyl absorptions located near 1750 wavenumbers (minor; assigned to "strained ring" carbonyl groups, e.g., "uret-dione" structures from the dimerization reaction of two NCO groups), 1710 wavenumbers (major; assigned to aromatic urethane carbonyl group), and 1650 wavenumbers (minor; assigned to free and reacted caprolactam groups).

Based on the FT-IR and $^1$H-NMR structural characterization, the reaction between resorcinol, caprolactam and MONDUR® ML in the presence of dibutyltin dilaurate yielded Example 9 which may comprise a mixture of at least Compounds (7) to (9) according Scheme D above.

A Differential Scanning Calorimetric (DSC) analysis of Example 9 was performed in a Perkin Elmer DSC 7 analyzer in the presence of nitrogen atmosphere and at a heating rate of 10° C./minute. The DSC thermogram curve showed a broad endothermic peak in the 70 to 130° C. range, with a major peak at 82° C. and two minor peaks at 96° C. and 109° C.

Examples 10-12

Examples 10-12 were prepared according to the procedure for Example 9 except that the molar ratios of MONDUR® ML, resorcinol and caprolactam in the reaction were different as shown in Table 10 below. Examples 10-12 were characterized by $^1$H-NMR. The following structures listed in Table 10 were identified and their relative amounts were measured semi-quantitatively by $^1$H-NMR

TABLE 10

| | Sample | | |
|---|---|---|---|
| | Ex. 10 | Ex. 11 | Ex. 12 |
| MONDUR ® ML/Resorcinol/ Caprolactam Mole Ratio | 1/0.5/1 | 1/0.75/0.5 | 1/0.25/1.5 |

TABLE 10-continued

| | Sample | | |
|---|---|---|---|
| | Ex. 10 | Ex. 11 | Ex. 12 |
| NMR Analysis, Structure (Mole Ratio) | | | |
| Total MDI structures | 44 | 47 | 42 |
| Total Reacted Caprolactam | 33 | 17 | 47 |
| Unreacted Caprolactam | 4 | 3 | 6 |
| Unreacted resorcinol | <1 | <1 | <1 |
| Total Resorcinolic Monourethanes & Diurethanes | 19 | 33 | 5 |
| Unassigned MDI structures | 2.6 | 1.6 | 3.3 |
| Free Resorcinol (LC/GC Analysis, wt %) | 0.28 | 0.3 | 0.5 |

Example 13

A mixture of resorcinol (0.6 mole, 66 grams), caprolactam (1.2 mole, 135.8 grams) and dibutyltin dilaurate (catalyst, 0.066 gram) was charged into a 500 ml four-necked glass reactor equipped with a mechanical stirrer, a thermometer, an addition funnel and a reflux condenser connected to a $CaCl_2$ guard tube. The reactor was then purged with nitrogen. After the reaction mixture was heated to about 120 to 125° C. to melt the resorcinol, 300 grams (1.2 mole) of MONDUR® ML was added slowly into the molten resorcinol with good stirring over a period of about 1 to 2 hours at 130 to 160° C. At the end of the addition, the reaction mixture appeared as a viscous clear yellow solution. Stirring and heating were continued for an additional period of about 1 to 3 hours to complete the reaction between resorcinol and MONDUR® ML. Finally, the material was poured onto a tray and cooled. The final product (i.e., Example 13) appeared as a light yellow colored brittle resin, which was then crushed into a white or faint yellow powder.

Example 13 was characterized by FT-IR, $^1$H-NMR and $^{13}$C-NMR. The following structures listed in Table 11 were identified and their relative amounts were measured semi-quantitatively by $^1$H-NMR (as solutions in DMSO-$d_6$).

TABLE 11

| Structure | Mole Ratio |
|---|---|
| Total MDI structures | 44 |
| Total Reacted Caprolactam | 34 |
| Unreacted Caprolactam | 3 |
| Unreacted resorcinol | <1 |
| Total Resorcinolic Monourethanes & Diurethanes | 9 |
| Unassigned MDI structures | 10 |

Example 14

Example 14 was prepared using an attritor according to the preparation procedure for Example 8 except that Example 5 was replaced with Example 13. The dispersion mixture in the attritor contained 200 grams of Example 13, 371.4 grams of distilled water, 22.8 grams of AEROSOL® OT surfactant, and 3 drops of AF 9000 silicone antifoam. The attritor ran for 5 hours at 700 rpm. The final particle size analysis was as follows: MV=3.724 μm, 90%<6.587 μm, 50%<3.307 μm. The final material (i.e., Example 14) was a stiff paste which would flow after some stirring.

Example 14 was used in the preparation of single- and double-step RFL dipping formulations and evaluation of its performance against GRILBOND® IL-6 (caprolactam-blocked 4,4'-MDI) in improving the adhesion of PET tire cords to rubber compounds.

Example 15

The formulation of the rubber composition used in the testing and evaluation of resorcinol-blocked diisocyanates against the commercially available GRILBOND® IL-6 and its cure properties are shown in Table 12.

TABLE 12

| Rubber Composition and Cure Properties. | |
|---|---|
| Rubber Composition, phr | |
| CV60 Natural Rubber | 70 |
| Styrene-Butadiene Rubber 1502 | 30 |
| N660 Carbon Black | 50 |
| Zinc Oxide | 4 |
| Stearic Acid | 2 |
| Naphthenic Oil | 5 |
| TMQ | 1.8 |
| Sulfur (80%) | 3.13 |
| MBTS | 0.8 |
| Cure Properties (MDR Cure @160° C.) | |
| $M_H$, dN-m | 12.43 |
| $M_L$, dN-m | 1.30 |
| $t_s2$, min | 2.08 |
| t' 50, min | 4.02 |
| t' 90, min | 9.22 |
| Cure Rate, dN-m/min | 1.12 |
| Mooney Viscosity, 100° C. | |
| Initial peak | 58.1 |
| ML (1 + 4) | 41.5 |
| Mooney Scorch, 125° C. | |
| Initial peak | 42.4 |
| ML | 30.3 |
| $t_5$ | 17.4 |
| $t_{35}$ | 22.1 |

Example 16

Single-step RFL adhesive dipping formulations prepared from GRILBOND® IL-6 and two resorcinol-blocked MONDUR® ML (2,4'- and 4,4'-MDI mixture) diisocyanate compounds and their compositions are shown in Table 13.

TABLE 13

| Single-Step Adhesive Dipping formulations for PET Cords. Composition (Formulation), grams | |
|---|---|
| Water | 85.16 |
| Sodium hydroxide (50%, aqueous) | 1.16 |
| PENACOLITE ® Resin R-50 (50%, aqueous) | 15.66 |
| Formaldehyde (37%, aqueous) | 3.22 |
| Resin Solution Total | 105.19 |
| GENTAC ® 118 (42.5%, aqueous) | 97.08 |
| Water | 6.48 |
| GRILBOND ® IL-6 or Blocked Isocyanate (diluted to 10% with water) | 41.26 |
| Total | 250.00 |
| Resin Solution Solids, % | 9.1 |
| F/R Molar Ratio | 1.21 |
| Total Solids, % | 21.99 |

TABLE 13-continued

Single-Step Adhesive Dipping formulations for PET Cords.
Composition (Formulation), grams

| | |
|---|---|
| GRILBOND ® (or) Blocked Isocyanate:Latex Ratio | 1:10 |
| Measured pH | 9.3–9.4 |

R = Resorcinol,
F = Formaldehyde
Blocked Isocyanates:
(1) Resorcinol-MONDUR ® ML (Example 8)
(2) Resorcinol-Caprolactam-MONDUR ® ML (Example 11)
(3) GRILBOND ® IL-6 (caprolactam-blocked 4,4'-MDI)

The non-adhesive activated PET cords from INVISTA, Wichita, Kans. (Cord Type 792, 1500/2, 10×10) were dipped in the single-step dipping formulations prepared according to the formulation listed in Table 13, and then dried and cured in air ovens set under the conditions shown in Table 14. These cords were then embedded in the uncured rubber compound having the composition shown in Table 12, vulcanized and tested for unaged H-pull adhesion per ASTM D 4776, which is incorporated herein by reference. The results obtained are summarized in Table 14.

The results in Table 14 indicate that the resorcinol-blocked compounds obtained from the MDI isomers can provide performance equal to or better than any caprolactam-blocked methylene-bis-(4-phenylisocyanate) such as GRILBOND® IL-6 when used as an additive in the RFL formulation in the place of the caprolactam-blocked methylene-bis-(4-phenyl-isocyanate). With resorcinol-blocked compounds, filament breakage has been observed in the H-pull adhesion tests. This strongly suggests that the adhesive strengths between the PET fiber and RFL adhesives containing resorcinol-blocked isocyanate can be much stronger.

Example 17

The details on the two step RFL adhesive formulations containing the resorcinol-blocked diisocyanate compounds and GRILBOND® IL-6 (control) are presented in Table 15.

TABLE 14

Single-Step Dip Adhesion Performance with Blocked Isocyanates.

| | Blocked Isocyanate Used: | | |
|---|---|---|---|
| | GRILBOND ® IL-6 | Example 8 | Example 11 |
| | Blocked Isocyanate Type: | | |
| | Caprolactam-blocked MDI | Resorcinol-blocked MONDUR ® ML | Resorcinol/Caprolactam - blocked MONDUR ® ML |
| H-Test Results - Unaged Adhesion (Cord T792: Non-adhesive activated PET cord from INVISTA, 1500/2, 10 × 10) | | | |
| 1st Oven: Temperature (° C.)/sec | 170/120 | 170/120 | 170/120 |
| 2nd Oven: Temperature (° C.)/sec | 230/60 | 230/60 | 230/60 |
| Isocyanate:Latex Ratio | 1:10 | 1:10 | 1:10 |
| Undesiccated Cord | | | |
| Number of pulls | 15 | 15 | 15 |
| Rubber Coverage, % | 85 | 80 | 80 |
| Peak Load, N | 126.9 | 127.6 | 115.4 |
| Energy, N-m | 0.91 | 0.94 | 0.86 |
| Broken Cords, % | 0 | 0 | 0 |
| Desiccated Cords (cords taken from beginning of run) | | | |
| Number of pulls | 10 | 10 | 10 |
| Rubber Coverage, % | 90 | 80* | 70* |
| Peak Load, N | 150.4 | 166.0 | 157.7 |
| Energy, N-m | 1.12 | 1.25 | 1.15 |
| Broken Cords, % | 0 | 0 | 0 |
| Desiccated Cords (cords taken from end of run) | | | |
| Number of pulls | 15 | 15 | 15 |
| Rubber Coverage, % | 90 | 60** | 80* |
| Peak Load, N | 166.2 | 174.7 | 162.2 |
| Energy, N-m | 1.26 | 1.36 | 1.26 |
| Broken Cords, % | 0 | 0 | 0 |

*Some filament breakage;
**Much filament breakage
H-Test Conditions: ⅜" mold; cure - 160° C./15 min; samples assembled in cold mold and cured next day

TABLE 15

Two Step Adhesive Dipping formulations for PET Cords.

| | Blocked Isocyanate Used: | |
|---|---|---|
| | GRILBOND ® IL-6 | Experimental Blocked Isocyanate* |
| Subcoat Formulation, g | | |
| Water | 86.17 | 82.75 |
| GRILBOND ® IL-6 (50%, aqueous) | 7.02 | 0.00 |
| Experimental Blocked Isocyanate* | 0.00 | 10.46 |
| DENACOL ® EX313 | 1.37 | 1.37 |
| AEROSOL ® OT (2.2%) | 5.44 | 5.42 |
| Subcoat Total | 100.00 | 100.00 |
| Topcoat Formulation | | |
| Water | | 78.51 |
| Sodium hydroxide (50%, aqueous) | | 0.42 |
| PENACOLITE ® Resin R-50 (50%, aqueous) | | 11.79 |
| Formaldehyde (37%, aqueous) | | 5.71 |
| Resin Solution Total | | 96.43 |
| GENTAC ® 118 (41%, aqueous) | | 114.17 |
| Water | | 33.78 |
| Ammonium Hydroxide (28%, aqueous) | | 5.61 |
| Topcoat Total | | 250.00 |
| Resin Solution Solids, % | | 8.5 |
| F/R Molar Ratio | | 2.03 |
| Total Solids, % | | 22.01 |
| Measured pH | | 10.1 |

*Example 8 or 11, 33.6%, aqueous
R = Resorcinol,
F = Formaldehyde

In the two-step RFL formulations, the subcoat formulations contained the blocked isocyanate compounds and the topcoat contained the standard RFL composition. Cord T792 was used in the adhesive performance evaluation. The cords were first coated with the subcoat, dried and then coated with the RFL topcoat. The drying and cure conditions of the oven are given in Table 16. The cords were then embedded in the uncured rubber compound having the composition shown in Table 12, vulcanized and tested for unaged H-pull adhesion. The results are presented in Table 16.

TABLE 16

Two Step Dip Adhesion Performance with Blocked Isocyanates.

| | Subcoat: | | |
|---|---|---|---|
| | GRILBOND ® IL-6/Epoxy | Resorcinol-MONDUR ® ML/Epoxy | Resorcinol-Caprolactam-MONDUR ® ML/Epoxy |
| | Type of Blocked Isocyanate: | | |
| | Caprolactam-MDI | Resorcinol-MONDUR ® ML | Resorcinol-Caprolactam-MONDUR ® ML |
| H-Test Results - Unaged Adhesion (Cord T792: Non-adhesive activated PET cord from INVISTA, 1500/2, 10 × 10) | | | |
| 1st Oven: Temperature (° C.)/sec | 170/120 | 170/120 | 170/120 |
| 2nd Oven: Temperature (° C.)/sec | 230/60 | 230/60 | 230/60 |
| Subcoat solids, % | 5 | 5 | 5 |
| Undesiccated Test Cord | | | |
| Number of pulls | 10 | 10 | 10 |
| Rubber Coverage, % | 30 | 90 | 80 |
| Peak Load, N | 81.5 | 140.1 | 118.1 |
| Energy, N-m | 0.51 | 1.15 | 0.87 |
| Broken Cords, % | 0 | 0 | 0 |
| Desiccated Test Cord (cords taken from end of run) | | | |
| Number of pulls | 12 | 13 | 14 |
| Rubber Coverage, % | 70 | 90 | 80 |
| Peak Load, N | 143.1 | 171.7 | 153.3 |
| Energy, N-m | 1.00 | 1.31 | 1.11 |
| Broken Cords, % | 0 | 0 | 0 |

H-Test Conditions: ⅜" Mold; Cure: 160° C./15 min.; samples assembled in cold mold and cured next day The results in Table 16 indicate that the resorcinol-blocked MDI isomers produced excellent adhesion properties when compared to the well-known and widely-used caprolactam-blocked 4,4'-MDI (GRILBOND® IL-6).

Example 18

A mixture of resorcinol (4.0 moles, 440.4 grams) and dibutyltin dilaurate (catalyst, 0.44 gram) was charged into a 1 liter four-necked glass reactor equipped with a mechanical stirrer, thermometer, addition funnel and reflux condenser connected to a CaCl$_2$ guard tube. The reactor was then purged with nitrogen. After the reaction mixture was heated to about 120 to 125° C. to melt the resorcinol, MONDUR ML (500 grams, 2.0 mole; a mixture of 2,4'- and 4,4'-diphenylmethane diisocyanate obtained from Bayer Corporation; the mole ratio of 4,4'- and 2,4'-MDI in the MONDUR® ML is 48:52) was added slowly into the molten resorcinol with good stirring over a period of about 1 to 2 hours at 130 to 160° C. At the end of MONDUR® ML addition, the reaction mixture appeared as a viscous clear orange solution. Stirring and heating were continued for an additional period of about 1 to 3 hours to complete the reaction. Next, the product was poured onto a tray and cooled. The product appeared as a yellow colored brittle resin, which was then crushed into a yellow powder (Example 18).

Example 18 obtained from the reaction of resorcinol with MONDUR® ML using dibutyltin dilaurate as the catalyst was characterized by FT-IR and $^1$H NMR. The FT-IR analysis indicated no unreacted NCO structure. The structures of Example 18, as shown in Table 17 below, were identified and measured semi-quantitatively by $^1$H NMR.

TABLE 17

| Structure | Mole Ratio |
| --- | --- |
| Total MDI structures | 34 |
| Unreacted resorcinol | 14 |
| Resorcinolic monourethanes | 37 |
| Resorcinolic diurethanes | 15 |

Differential Scanning Calorimetric (DSC) analysis of Example 18 was performed with a Perkin Elmer DSC 7 analyzer in nitrogen atmosphere and at a heating rate of 10° C./minute. The DSC thermogram showed endothermic peaks at 75° C. and 99° C. The peak appearing at 75° C. might be due to the presence of un-reacted resorcinol in the resorcinol blocked isocyanate compound.

Comparative Example A and Examples 19-22

Vulcanizable rubber compositions, i.e., Comparative Example A and Examples 19-22, were prepared according to the general rubber compound formulation disclosed in Table 18 with differences in the methylene acceptor, methylene donor, methylene acceptor/methylene donor ratio and cobalt salt amount listed in Table 19.

TABLE 18

General Vulcanizable Rubber Composition Formluation Used for Preparing Comparative Example A and Examples 19–22.

| Master Batch | Parts by Weight |
| --- | --- |
| First Stage | |
| 1. Natural Rubber | 100 |
| 2. Carbon Black | 55 |
| 3. Zinc Oxide | 8 |
| 4. Stearic Acid | 1 |
| 5. N-(1,3-Dimethylbutyl)-N'-Phenyl-p-Phenylene Diamine | 2 |
| 6. Pre-Vulcanization Inhibitor [N-(Cyclohexylthio) Phthalimide] | 0.2 |
| 7. Polymerized 1,2-Dihydro-2,2,4-Trimethyl Quinoline | 1 |
| Second Stage | |
| 8. Methylene Acceptor (See Table 19) | See Table 19 |
| 9. Cobalt Salt (MANOBOND ® 680C, 22.6% Co) | 0.44 |
| Third Stage (Final) | |
| 10. Insoluble Sulfur (80% Sulfur) | 5 |
| 11. N,N-Dicylohexyl-2-Benzenethiazole Sulfenamide | 1 |
| 12. Methylene Donor (HMMM, 72% Active) | See Table 19 |

TABLE 19

Specific Conditions Used for Preparing Comparative Example A and Examples 19–22.

| | Comparative Example A | Example 19 | Example 20 | Example 21 | Example 22 |
| --- | --- | --- | --- | --- | --- |
| Methylene Acceptor | PENACOLITE ® B-20-S | Example 18 | Example 18 | Example 18 | Example 18 |
| Methylene Donor | HMMM | HMMM | HMMM | None | HMMM |
| Acceptor/Donor, phr (Weight) | 3/2.78 | 3/2.78 | 3/4.17 | 3.0/None | 3/4.17 |
| Cobalt (MANOBOND ® 680 C., 22.6% Co) | 0.44 | 0.44 | 0.44 | 0.44 | None |

The vulcanizable rubber compositions were prepared using the following process. In the first stage, all the first stage ingredients listed in Table 18 were mixed to about 150° C. in a Banbury mixer to produce a masterbatch. In the second stage, a methylene acceptor (i.e., Example 18 or PENA-COLITE® B-20-S) and a cobalt salt were added to the masterbatch on a two-roll mill at about 121° C. In the third stage, insoluble sulfur, an accelerator (i.e., N,N-dicylohexyl-2-benzenethiazole sulfenamide) and a methylene donor (i.e., HMMM) were mixed with the mixture from the second stage at 95° C. The rubber compositions were conditioned overnight in a constant temperature room at about 23° C. and 50% relative humidity. The rubber compositions were then tested as described below.

Testing of Comparative Example A and Examples 19-22

The Mooney viscosity and Mooney Scorch properties of Comparative Example A and Examples 19-22 were measured using an Alpha Technologies MV2000 Mooney Viscometer according to ASTM D1646-04 which is incorporated herein by reference. Mooney viscosity is defined as the shearing torque resisting rotation of a cylindrical metal disk (or rotor) embedded in rubber within a cylindrical cavity. The cure properties of Comparative Example A and Examples 19-22 were measured with an Alpha Technologies MDR2000 Rheometer at 150° C., 0.50 arc and 1.67 Hz according to ASTM D 5289, which is incorporated herein by reference. The samples were cured at 100° C., 125° C. and 150° C., respectively for the Mooney viscosity, Mooney scorch and cure property measurement. The Mooney viscosity, Mooney scorch and cure properties of Comparative Example A and Examples 19-22 are shown in Table 20 below.

TABLE 20

The Viscosity, Scorch and Cure Properties of Comparative Example A and Examples 19–22.

|  | Comparative Example A | Example 19 | Example 20 | Example 21 | Example 22 |
|---|---|---|---|---|---|
| Mooney Viscosity, 100° C. | | | | | |
| Initial Peak | 69 | 76 | 72 | 76 | 69 |
| ML (1 + 4) | 59 | 56 | 55 | 59 | 53 |
| Mooney Scorch, 125° C. | | | | | |
| Initial Peak | 52.3 | 55.4 | 53.9 | 59.5 | 56.6 |
| ML | 43.3 | 42.7 | 42.4 | 42.6 | 38.4 |
| Scorch Time, $t_5$, minutes | 24.2 | 26.4 | 25.5 | 25.8 | 30.9 |
| Scorch Time, $t_{35}$, minutes | 33.5 | 35 | 35.1 | 32 | 41.4 |
| MDR Rheometer Sample Cured at 150° C. | | | | | |
| $M_H$, dN-m | 35.66 | 40.15 | 43.59 | 26.65 | 40.01 |
| $M_L$, dN-m | 2.51 | 2.62 | 2.49 | 2.64 | 2.35 |
| Scorch Time, $t_s2$, Minutes | 2.6 | 2.95 | 2.68 | 3.4 | 3.14 |
| Cure Time, t'90, Minutes | 19.61 | 18.45 | 19.9 | 16.35 | 27.72 |
| Cure Rate, dN-m/Min | 1.64 | 2.05 | 2.03 | 1.51 | 1.3 |

The adhesion properties of Comparative Example A and Examples 19-22 were measured according to ASTM D 2229-02 using brass plated steel cord (Wire: Bekaert 3×0.2+6×0.35 with 63.72% copper plating) embedded 19 mm into the rubber pad. The samples were cured to the Rheometer t' 100 plus seven minutes at 150° C. and then tested under unaged condition, steam-aged condition and humidity-aged condition. ASTM D 2229-02 is incorporated herein by reference. The steel cord adhesion properties of Comparative Example A and Examples 19-22 are shown in Table 21 below.

TABLE 21

The Steel Cord Adhesion Properties with t' 100 + 7 Cure of Comparative Example A and Examples 19–22.

|  | Comparative Example A | Example 19 | Example 20 | Example 21 | Example 22 |
|---|---|---|---|---|---|
| Unaged Adhesion | | | | | |
| Pullout Force, N | 1408 | 1304 | 1354 | 1334 | 696 |
| Rubber Coverage, % | 95 | 80 | 95 | 80 | 30 |

TABLE 21-continued

The Steel Cord Adhesion Properties with t' 100 + 7 Cure of Comparative Example A and Examples 19–22.

|  | Comparative Example A | Example 19 | Example 20 | Example 21 | Example 22 |
|---|---|---|---|---|---|
| Energy, N-m | 13.00 | 11.63 | 12.23 | 12.21 | 4.71 |
| Steam-Aged Adhesion (25.5 Hours, 120° C.) | | | | | |
| Pullout Force, N | 1210 | 824 | 1211 | 534 | 1240 |
| Rubber Coverage, % | 80 | 40 | 90 | 10 | 90 |
| Energy, N-m | 10.42 | 5.37 | 10.52 | 3.1 | 11.31 |
| Humidity-Aged Adhesion (21 Days, 85° C./95 RH) | | | | | |
| Pullout Force, N | 1188 | 994 | 1213 | 760 | 786 |
| Rubber Coverage, % | 80 | 70 | 85 | 30 | 60 |
| Energy, N-m | 8.76 | 6.32 | 9.22 | 4.51 | 3.99 |

The dynamic mechanical properties of Comparative Example A and Examples 19-22 were measured using a TA Instruments ARES-RDA at both 23° C. and 60° C. The tests were run at a frequency of 1.0 Hz and a strain of 0.2%, 2.0%, 5.0% and 9.8%. A rectangular specimen 18 mm long, 12 mm wide and 4 mm thick was used. The dynamic mechanical properties of Comparative Example A and Examples 19-22 at 23° C. and 60° C. are shown in Table 22 and Table 23, respectively.

TABLE 22

The Dynamic Mechanical Properties at 23° C. of Comparative Example A and Examples 19–22.

|  | Comparative Example A | Example 19 | Example 20 | Example 21 | Example 22 |
|---|---|---|---|---|---|
| Room Temperature (23° C.) At 0.2% Strain | | | | | |
| Storage Modulus, G' (MPa) | 21.64 | 27.04 | 28.81 | 20.39 | 25.29 |
| Tangent Delta, δ | 0.070 | 0.065 | 0.066 | 0.075 | 0.069 |
| At 2.0% Strain | | | | | |
| Storage Modulus, G' (MPa) | 13.90 | 17.20 | 18.44 | 12.77 | 15.94 |
| Tangent Delta, δ | 0.184 | 0.189 | 0.186 | 0.211 | 0.192 |
| At 5.0% Strain | | | | | |
| Storage Modulus, G' (MPa) | 9.98 | 12.27 | 13.26 | 8.94 | 11.49 |
| Tangent Delta, δ | 0.230 | 0.239 | 0.235 | 0.260 | 0.236 |
| At 9.8% Strain | | | | | |
| Storage Modulus, G' (MPa) | 7.90 | 9.59 | 10.40 | 6.87 | 9.04 |
| Tangent Delta, δ | 0.225 | 0.236 | 0.232 | 0.247 | 0.231 |

TABLE 23

The Dynamic Mechanical Properties at 60° C. of Comparative Example A and Examples 19–22.

|  | Comparative Example A | Example 19 | Example 20 | Example 21 | Example 22 |
|---|---|---|---|---|---|
| Elevated Temperature (60° C.) At 0.2% Strain | | | | | |
| Storage Modulus, G' (MPa) | 19.05 | 24.65 | 25.99 | 18.54 | 23.03 |
| Tangent Delta, δ | 0.071 | 0.65 | 0.066 | 0.084 | 0.069 |
| At 2.0% Strain | | | | | |
| Storage Modulus, G' (MPa) | 12.28 | 15.72 | 16.72 | 11.62 | 14.50 |
| Tangent Delta, δ | 0.176 | 0.179 | 0.176 | 0.214 | 0.183 |

TABLE 23-continued

The Dynamic Mechanical Properties at 60° C. of
Comparative Example A and Examples 19–22.

|  | Comparative Example A | Example 19 | Example 20 | Example 21 | Example 22 |
|---|---|---|---|---|---|
| At 5.0% Strain |  |  |  |  |  |
| Storage Modulus, G' (MPa) | 8.61 | 10.98 | 11.83 | 7.86 | 10.22 |
| Tangent Delta, δ | 0.224 | 0.232 | 0.226 | 0.271 | 0.231 |
| At 9.8% Strain |  |  |  |  |  |
| Storage Modulus, G' (MPa) | 6.68 | 8.41 | 9.16 | 5.85 | 7.89 |
| Tangent Delta, δ | 0.225 | 0.234 | 0.227 | 0.263 | 0.231 |

The DMA data in Table 22 and 23 indicate that the resorcinol-blocked isocyanate compositions, such as Example 18, can improve the storage modulus and tan δ of rubber compositions, such as Examples 19 and 20, over a wide range of strains at either 23° C. or 60° C.

The Shore A hardness of Comparative Example A and Examples 19-22 were measured according to ASTM-D2240-03, which is incorporated herein by reference. The tensile properties of Comparative Example A and Examples 19-22 were measured according to ASTM D412, which is incorporated herein by reference. The Die C Tear properties of Comparative Example A and Examples 19-22 were measured according to ASTM D624C, which is incorporated herein by reference. The Shore A hardness, tensile properties, and Die C Tear properties of Comparative Example A and Examples 19-22 are shown in Table 24 below.

TABLE 24

The Hardness, Tensile and Tear Properties of
Comparative Example A and Examples 19–22.

|  | Comparative Example A | Example 19 | Example 20 | Example 21 | Example 22 |
|---|---|---|---|---|---|
| Shore A Hardness | 83 | 85 | 87 | 81 | 86 |
| Tensile Properties |  |  |  |  |  |
| 100% Modulus (MPa) | 10.16 | 10.74 | 11.03 | 9.17 | 10.36 |
| 300% Modulus (MPa) | 16.77 | 17.20 | 17.65 | 14.89 | 16.79 |
| Tensile Strength (MPa) | 26.6 | 26.5 | 25.8 | 26.4 | 26.2 |
| Elongation (%) | 467 | 462 | 442 | 504 | 462 |
| Energy to Break, N-m | 24.1 | 26.5 | 23.4 | 25.5 | 23.3 |
| Tear Properties (Die C) |  |  |  |  |  |
| Peak Load/Thickness, N/mm | 115.3 | 116.4 | 103.7 | 119.5 | 117.5 |
| Energy to Peak Load, N-m | 21.1 | 21.1 | 16.8 | 25.9 | 23.2 |

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. The method of making the compositions may be described as comprising a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling within the scope of the invention.

What is claimed is:

1. A resorcinol-blocked isocyanate composition comprising:

(a) a first compound having Formula (IIA):

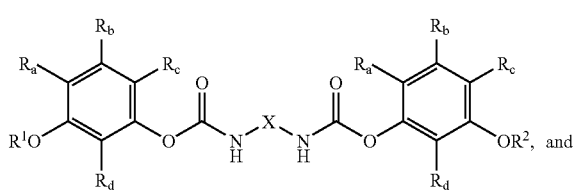

(IIA), and (b) a second compound having Formula (IIIA):

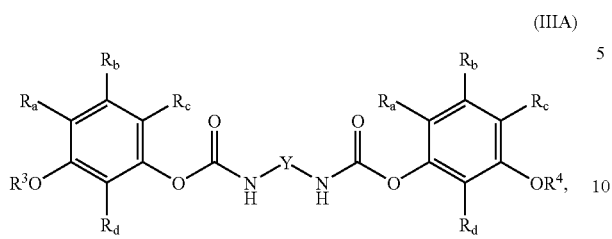
(IIIA)

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

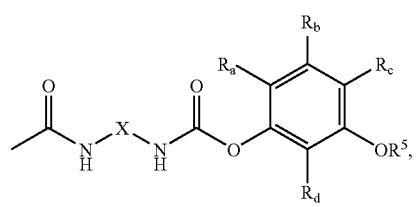
(IVA)

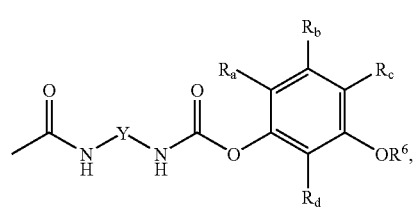
(IVB)

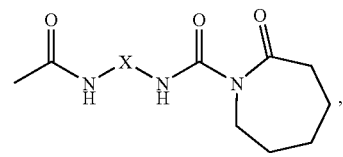
(IVC)

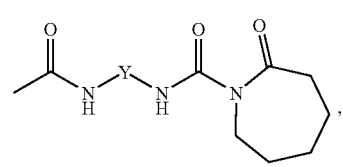
(IVD)

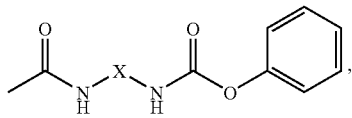
(IVE)

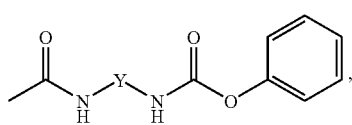
(IVF)

wherein each of $R^5$ and $R^6$ is independently H, acrylate, methacrylate, silyl ether, siloxanyl, aryl, aralkyl, acyl, alkyl or alkenyl.

2. The resorcinol-blocked isocyanate composition of claim 1, wherein each of X and Y is independently a divalent radical having one of the following formulae:

(A)

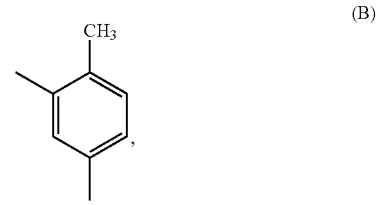
(B)

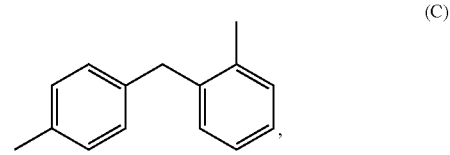
(C)

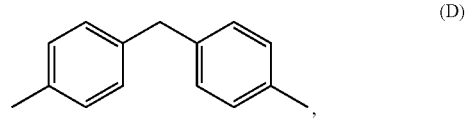
(D)

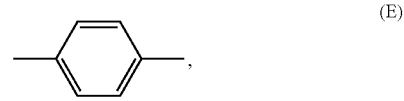
(E)

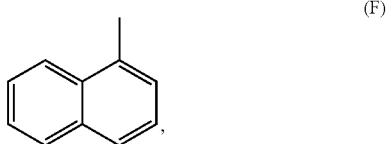
(F)

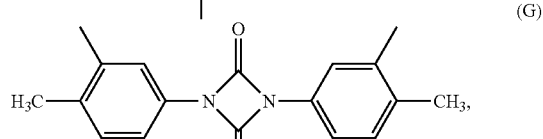
(G)

(H)

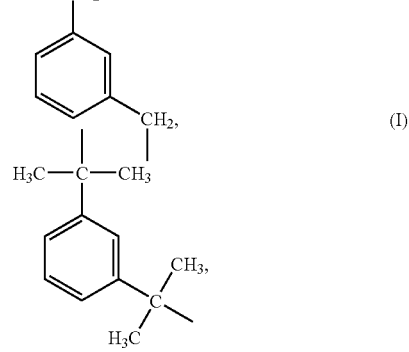
(I)

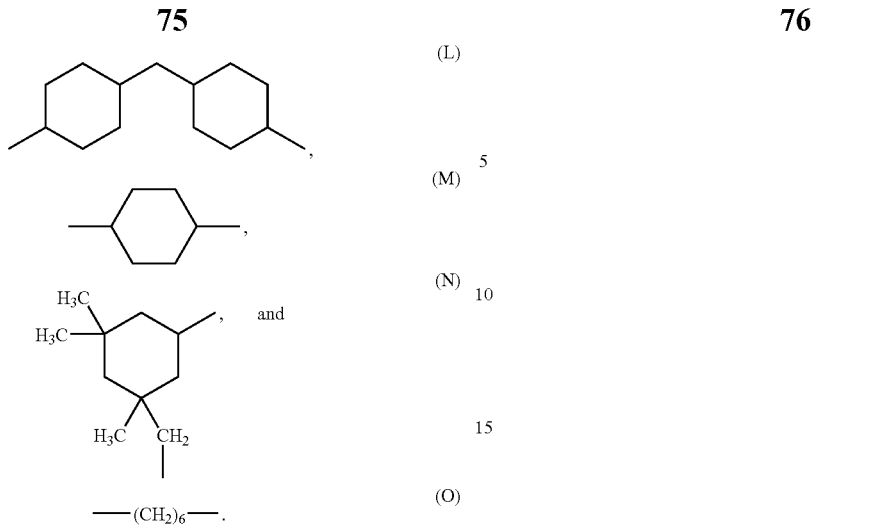

(L), (M), (N), (O)

3. The resorcinol-blocked isocyanate composition of claim 1 further comprising a third compound having Formula (IIB):

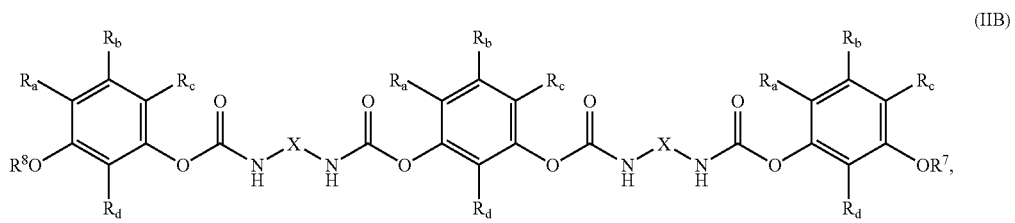

(IIB)

wherein X is alkylene, cycloalkylene, arylene, alkarylene, cycloalkarylene, aralkylene, heterocyclylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^7$ and $R^8$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF), with the proviso that Formula (IIA), Formula (IIB) and Formula (IIIA) are different from each other.

4. The resorcinol-blocked isocyanate composition of claim 3 further comprising a fourth compound having Formula (IIIB):

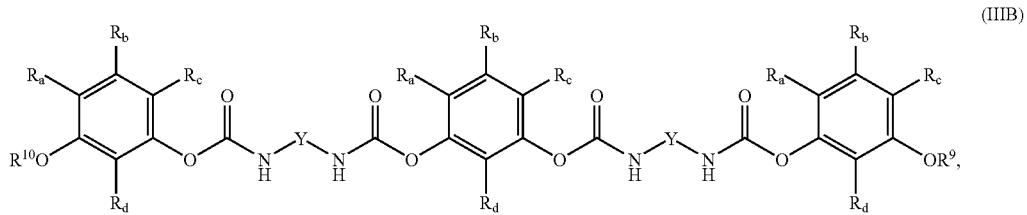

(IIIB)

wherein Y is alkylene, cycloalkylene, arylene, alkarylene, cycloalkarylene, aralkylene, heterocyclylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^9$ and $R^{10}$ is independently H, acrylate, methacrylate, silyl ether, siloxanyl, aryl, aralkyl, acyl, alkyl, alkenyl, Formula (IVA) or Formula (IVB), with the proviso that Formula (IIA), Formula (IIB), Formula (IIIA) and Formula (IIIB) are different from each other.

5. The resorcinol-blocked isocyanate composition of claim 4 further comprising a fifth compound having Formula (IIC):

or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, aryl, acyl, alkyl, aryl, aralkyl, or alkaryl; and each of $R^{11}$ and $R^{12}$ is independently H, acrylate, methacrylate, silyl ether, siloxanyl, aryl, aralkyl, acyl, alkyl, alkenyl, Formula (IVA) or Formula (IVB), with the proviso that Formula (IIA), Formula (IIB), Formula (IIC), Formula (IIIA) and Formula (IIIB) are different from each other.

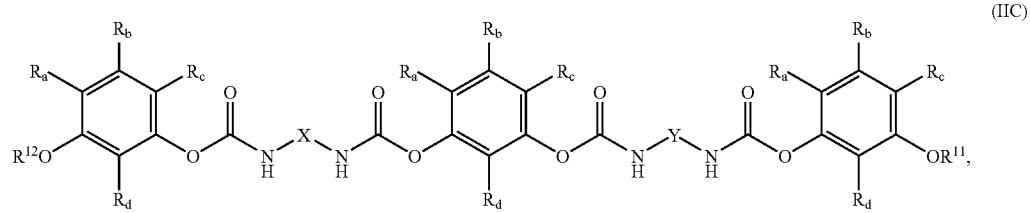

(IIC)

wherein X and Y are different and each of X and Y is independently alkylene, cycloalkylene, arylene, alkarylene, cycloalkarylene, aralkylene, heterocyclylene, heteroarylene 6. The resorcinol-blocked isocyanate composition of claim 5, wherein the resorcinol-blocked isocyanate composition comprises Compounds (1)-(5) having the formulae:

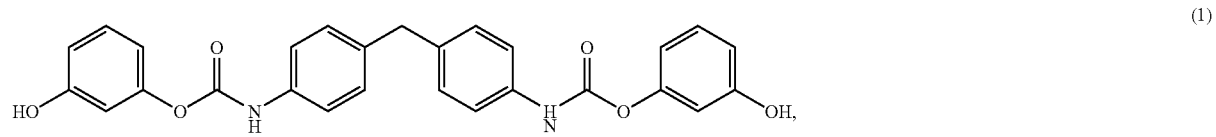

(1)

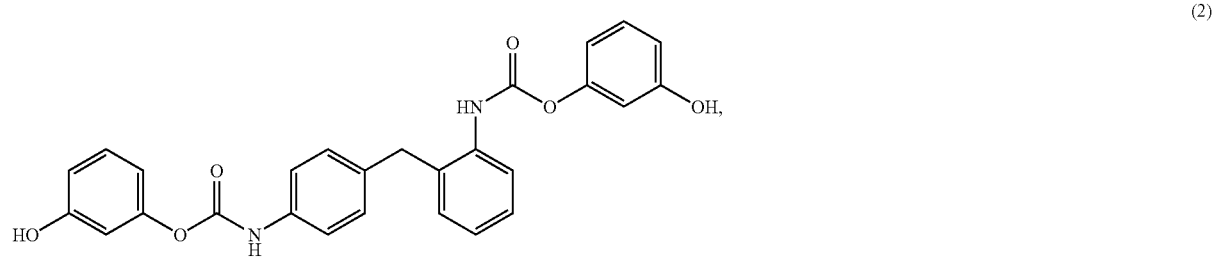

(2)

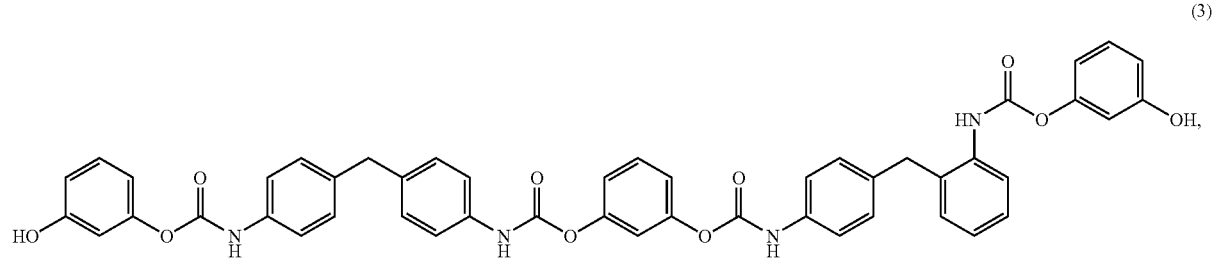

(3)

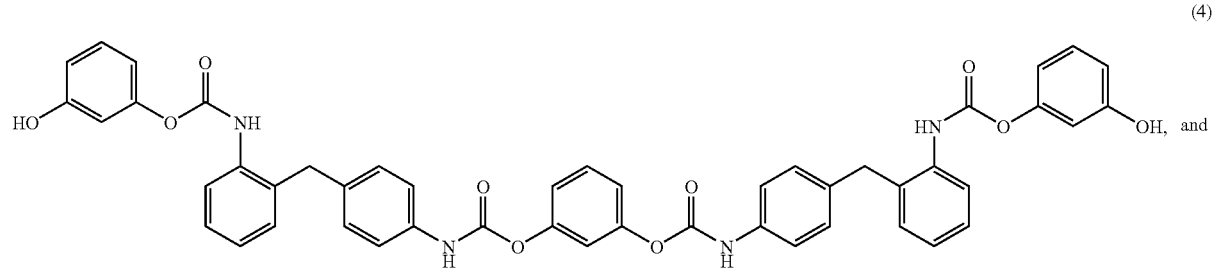

(4)

-continued

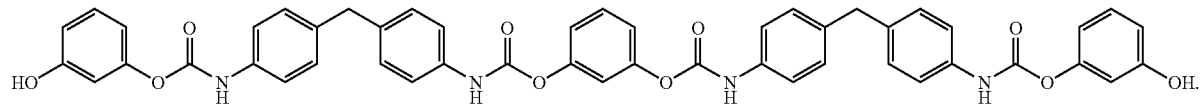
(5)

7. The resorcinol-blocked isocyanate composition of claim 6, wherein each of Compounds (1)-(5) is optionally substituted.

8. The resorcinol-blocked isocyanate composition of claim 6, wherein the resorcinol-blocked isocyanate composition has at least two melting temperatures.

9. The resorcinol-blocked isocyanate composition of claim 1, wherein the resorcinol-blocked isocyanate composition has at least two unblocking temperatures.

10. The resorcinol-blocked isocyanate composition of claim 1, wherein the mole ratio of Formula (IIA) to Formula (IIIA) is from about 10:90 to about 90:10.

11. The resorcinol-blocked isocyanate composition of claim 1, wherein the mole ratio of Formula (IIA) to Formula (IIIA) is from about 35:65 to about 65:35.

12. A process for preparing a resorcinol-blocked isocyanate composition comprising reacting at least two different isocyanate compounds with a resorcinol compound of Formula (I):

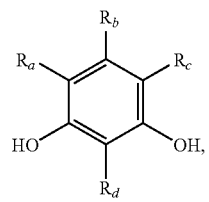
(I)

wherein the mole ratio of the resorcinol compound to the two or more isocyanate compounds is about x:1 where x is about 1.5, about 2.0, about 2.5 or about 3 and each of $R_a$, $R_b$, $R_c$ and $R_d$ is independently hydrogen, hydroxyl, halide, nitro, benzo, carboxy, acyl, alkyl, aryl, aralkyl, or alkaryl.

13. The process of claim 12, wherein the reaction occurs in the absence of a solvent.

14. The process of claim 12, wherein the reaction occurs in the presence of a catalyst.

15. The process of claim 14, wherein the catalyst is 3-methyl-1-phenyl-2-phospholene-1-oxide or dibutyltin dilaurate.

16. The process of claim 12, wherein the resorcinol compound is resorcinol.

17. The process of claim 12, wherein the at least two isocyanate compounds have the formulae O=C=N—X—N=C=O and O=C=N—Y—N=C=O wherein X and Y are different and each of X and Y is alkylene, cycloalkylene, arylene, alkarylene, cycloalkarylene, aralkylene, heterocyclylene, heteroarylene or a combination thereof.

18. The process of claim 17, wherein each of X and Y is independently a divalent radical having one of the following formulae:

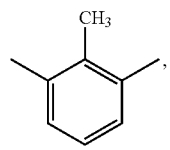
(A)

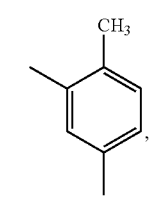
(B)

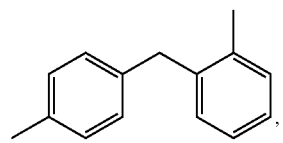
(C)

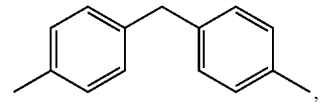
(D)

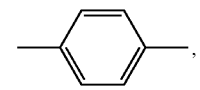
(E)

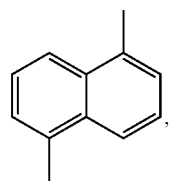
(F)

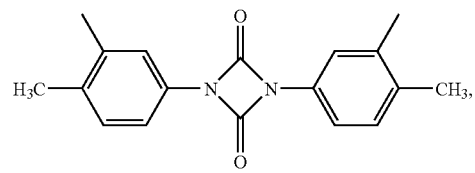
(G)

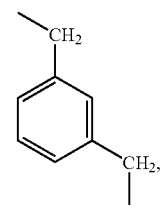
(H)

-continued

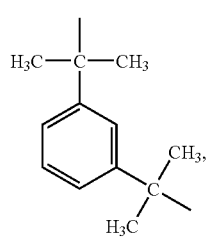
(I)

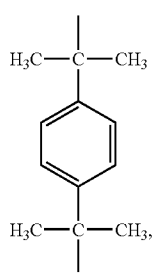
(J)

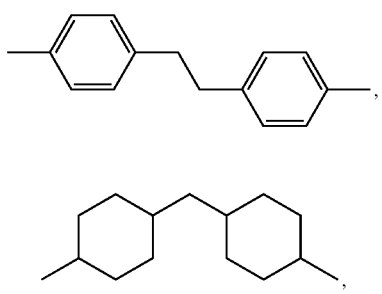
(K)

(L)

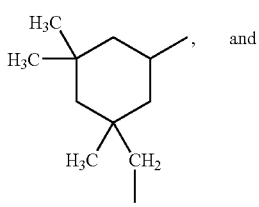
, and
(M)

—(CH₂)₆—.
(N)

19. The process of claim 12, wherein the reaction temperature is above the melting point of the resorcinol compound.

20. The process of claim 12, wherein at least a portion of the resorcinol compound of Formula (I) is replaced with a different blocking agent.

21. The process of claim 20, wherein the blocking agent is caprolactam, a phenol compound or a combination thereof.

22. The process of claim 21, wherein the phenol compound has Formula (IA):

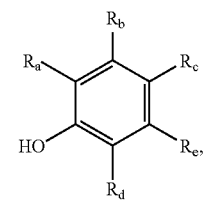
(IA)

wherein each of $R_a$, $R_b$, $R_c$, $R_d$ and $R_e$ of the phenol compound of Formula (IA) is independently hydrogen, halide, nitro, benzo, carboxy, acrylate, methacrylate, silyl ether, siloxanyl, acyl, alkyl, aryl, aralkyl, or alkaryl.

23. A vulcanizable rubber composition comprising or obtainable from a mixture comprising a rubber material, a methylene donor and a methylene acceptor comprising a resorcinol-blocked isocyanate composition, wherein the resorcinol-blocked isocyanate composition comprises:

(a) a first compound having Formula (IIA):

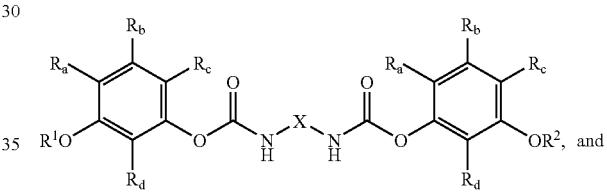
(IIA)

(b) a second compound having Formula (IIIA):

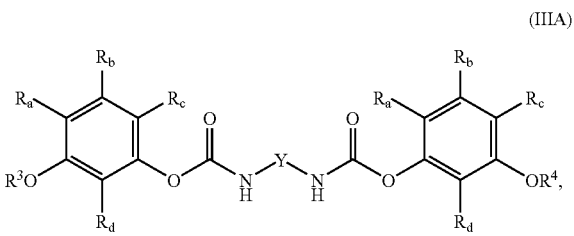
(IIIA)

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

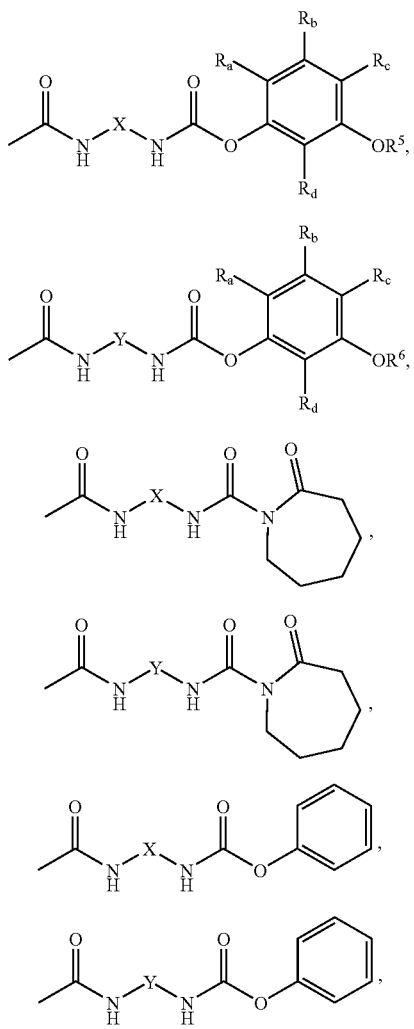

wherein each of $R^5$ and $R^6$ is independently H, acrylate, methacrylate, silyl ether, siloxanyl, aryl, aralkyl, acyl, alkyl or alkenyl.

24. The vulcanizable rubber composition of claim 23, wherein the rubber material is a natural or synthetic rubber.

25. The vulcanizable rubber composition of claim 23 further comprising a rubber reinforcement material.

26. The vulcanizable rubber composition of claim 25, wherein the rubber reinforcement material is in the form of fibers, filaments, fabrics or cords.

27. The vulcanizable rubber composition of claim 25, wherein the rubber reinforcing material is made of a polyester, a polyamide, carbon, glass, steel, polybenzoxazole or rayon.

28. The vulcanizable rubber composition of claim 27, wherein the reinforcing material is steel.

29. The vulcanizable rubber composition of claim 23 further comprising a vulcanizing agent.

30. The vulcanizable rubber composition of claim 23 further comprising at least an additive, wherein the additive is carbon black, zinc oxide, silica, an antioxidant, a stearate, an accelerator, an adhesion promoter, a cobalt salt, stearic acid, a filler, a plasticizer, a wax, a processing oil, a retarder, an antiozonant or a combination thereof.

31. A dipping formulation comprising the resorcinol-blocked isocyanate composition of claim 1.

32. The dipping formulation of claim 31 further comprising a solvent.

33. The dipping formulation of claim 31 further comprising an additive.

34. A dipping formulation comprising a resorcinol-blocked isocyanate composition and an additive, wherein the additive is an epoxy-containing compound, a thickener, an antifoam or a combination thereof, and wherein the resorcinol-blocked isocyanate composition comprises:

(a) a first compound having Formula (IIA):

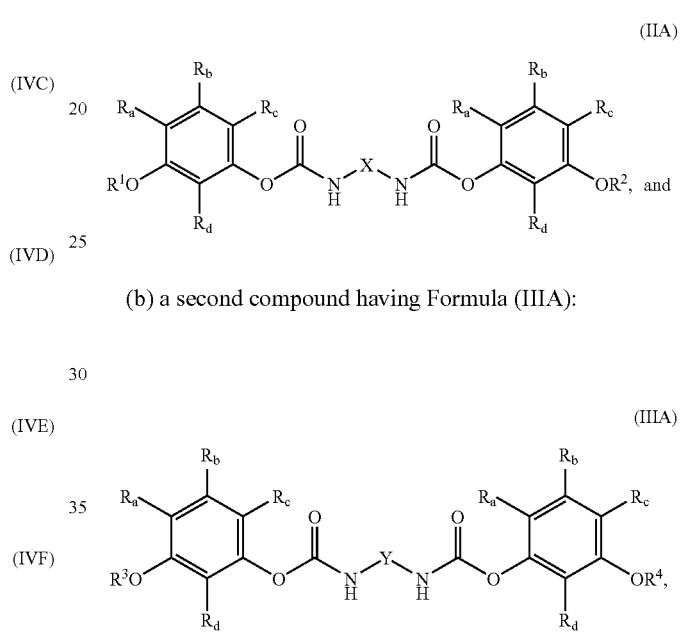

(b) a second compound having Formula (IIIA):

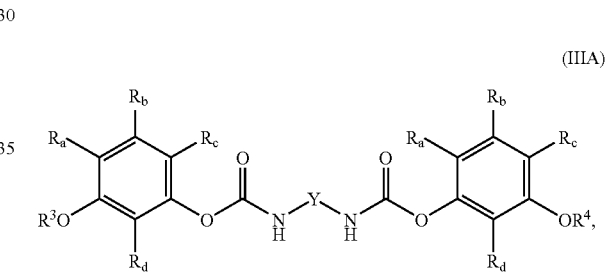

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

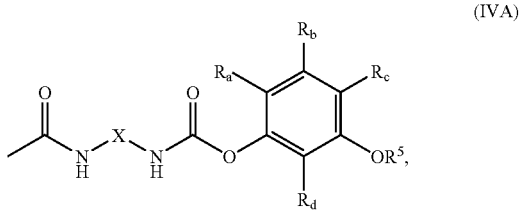

-continued

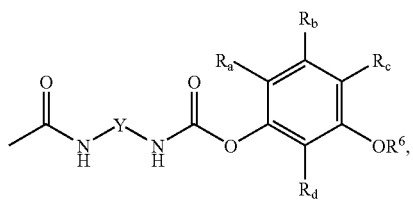
(IVB)

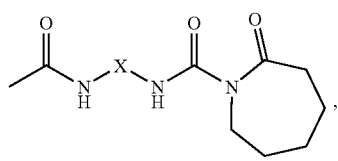
(IVC)

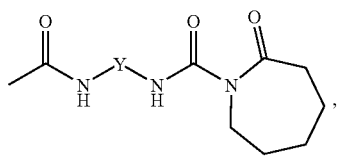
(IVD)

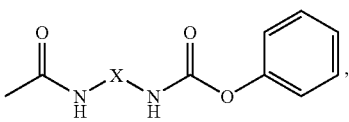
(IVE)

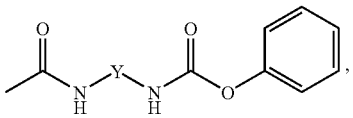
(IVF)

wherein each of $R^5$ and $R^6$ is independently H, acrylate, methacrylate, silyl ether, siloxanyl, aryl, aralkyl, acyl, alkyl or alkenyl.

35. A dipping formulation comprising a resorcinol-blocked isocyanate composition and a poly(vinyl pyridine/butadiene/styrene) latex, wherein the resorcinol-blocked isocyanate composition comprises:

(a) a first compound having Formula (IIA):

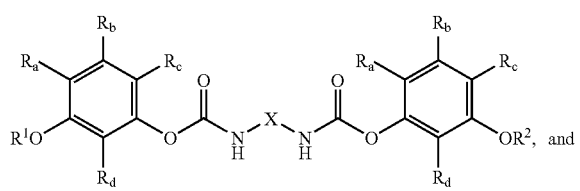
(IIA)

(b) a second compound having Formula (IIIA):

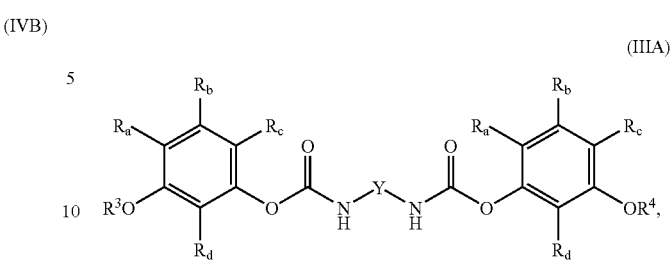
(IIIA)

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

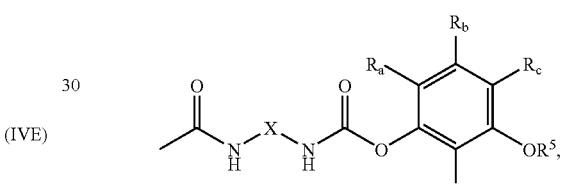
(IVA)

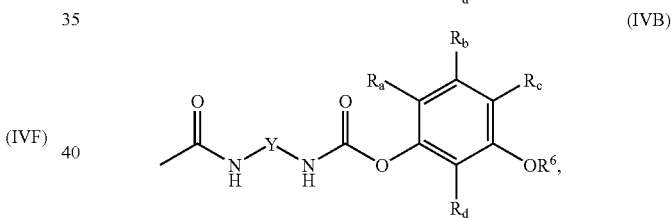
(IVB)

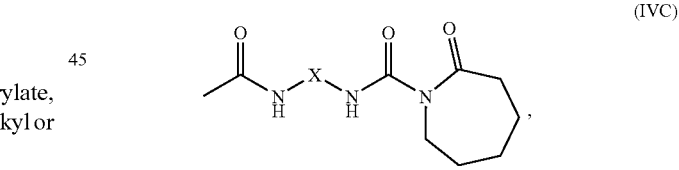
(IVC)

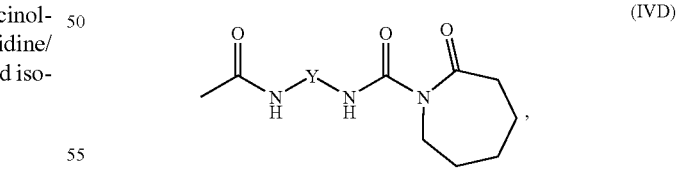
(IVD)

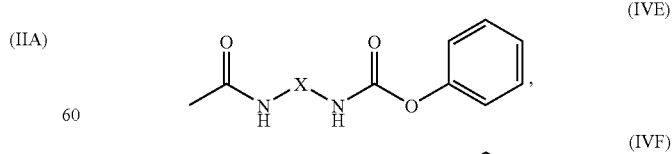
(IVE)

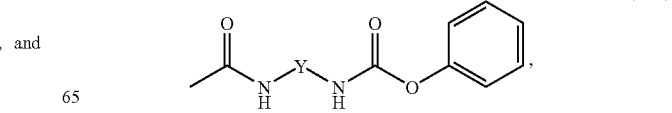
(IVF)

wherein each of $R^5$ and $R^6$ is independently H, acrylate, methacrylate, silyl ether, siloxanyl, aryl, aralkyl, acyl, alkyl or alkenyl.

36. A dipping formulation comprising a resorcinol-blocked isocyanate composition and a resin solution, wherein the resorcinol-blocked isocyanate composition comprises:

(a) a first compound having Formula (IIA):

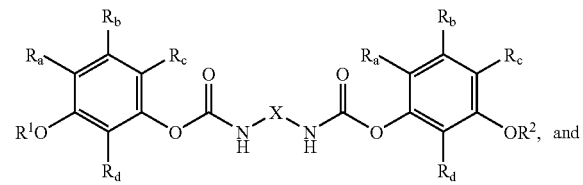

(IIA)

(b) a second compound having Formula (IIIA):

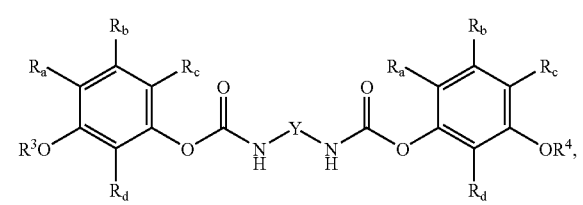

(IIIA)

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

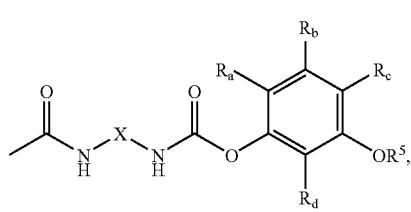

(IVA)

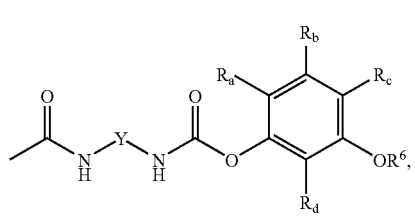

(IVB)

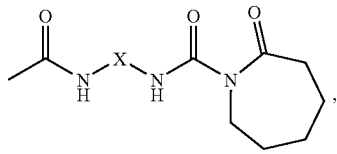

(IVC)

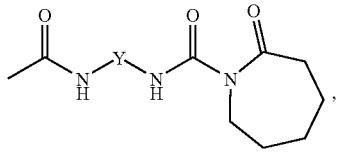

(IVD)

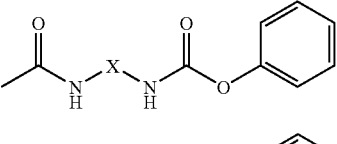

(IVE)

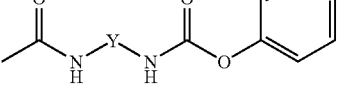

(IVF)

wherein each of $R^5$ and $R^6$ is independently H, acrylate, methacrylate, silyl ether, siloxanyl, aryl, aralkyl, acyl, alkyl or alkenyl.

37. The dipping formulation of claim 36, wherein the resin solution is a resorcinol-formaldehyde solution.

38. The dipping formulation of claim 37 further comprising an additive.

39. The dipping formulation of claim 38, wherein the additive is an antifoam.

40. A fabricated article comprising a rubber material and a rubber reinforcing material treated with a dipping formulation comprising a resorcinol-blocked isocyanate composition, wherein the resorcinol-blocked isocyanate composition comprises:

(a) a first compound having Formula (IIA):

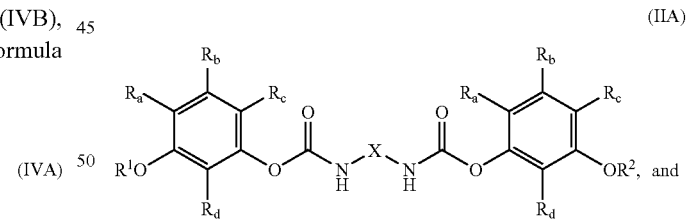

(IIA)

(b) a second compound having Formula (IIIA):

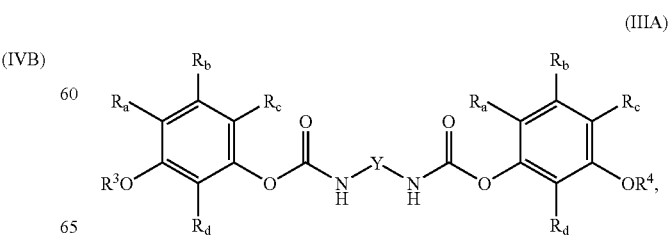

(IIIA)

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acrylate, methacrylate, silyl ether, siloxanyl, acyl, alkyl, aryl, aralkyl, or alkaryl; and each of $R^1$, $R^2$, $R^3$ and $R^4$ is independently H, acrylate, methacrylate, silyl ether, siloxanyl, aryl, aralkyl, acyl, alkyl, alkenyl, Formula (IVA), Formula (IVB), Formula (IVC), Formula (IVD), Formula (IVE) or Formula (IVF):

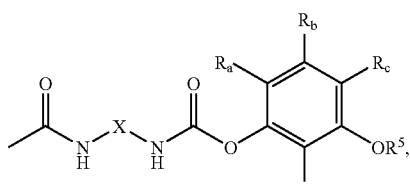

(IVA)

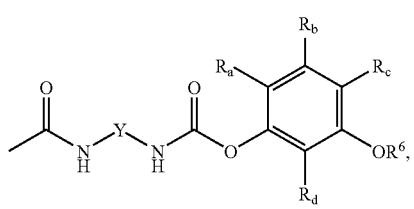

(IVB)

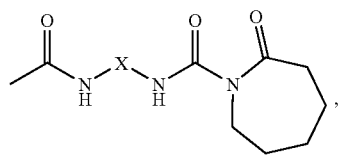

(IVC)

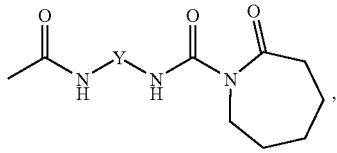

(IVD)

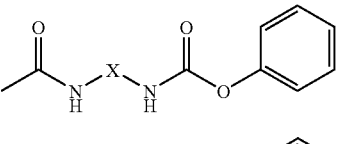

(IVE)

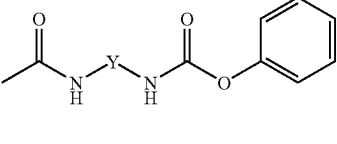

(IVF)

wherein each of $R_5$ and $R_6$ is independently H, acrylate, methacrylate, silyl ether, siloxanyl, aryl, aralkyl, acyl, alkyl or alkenyl.

41. The fabricated article of claim 40, wherein the rubber material is a natural or synthetic rubber.

42. The fabricated article of claim 40, wherein the rubber reinforcing material is in the form of fibers, filaments, fabrics or cords.

43. The fabricated article of claim 40, wherein the rubber reinforcing material is made of a polyester, a polyamide, carbon, glass, steel, a polybenzoxazole or rayon.

44. The fabricated article of claim 40, wherein the fabricated article is a tire, power transmission belt, conveyor belt, V-belt, hose printing roll, rubber shoe heel, rubber shoe sole, automobile floor mat, truck mud flap or ball mill liner.

45. A coating comprising a resin prepared by curing Formula (B), (B'), (C) or a combination thereof:

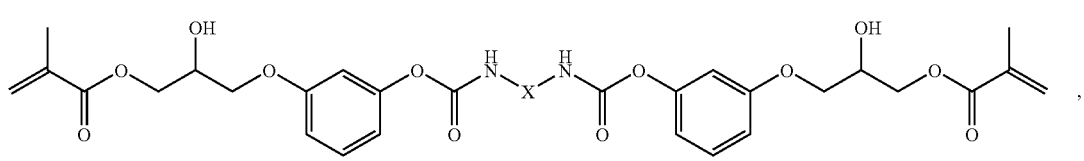

(B)

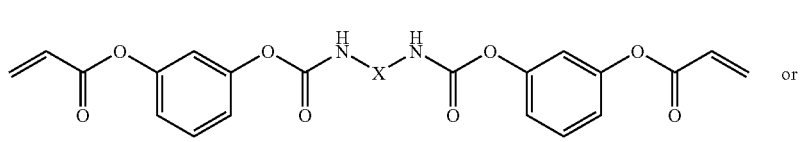

(B') or

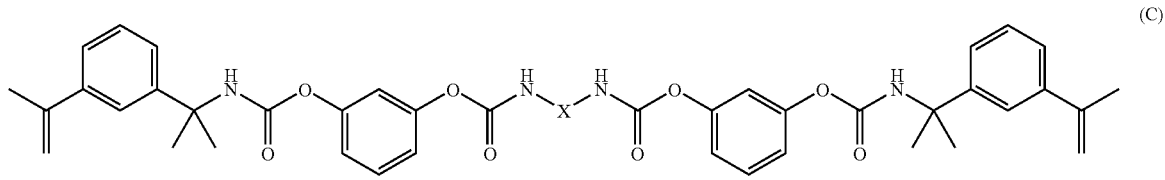

(C)

by heat, radiation or a combination thereof, wherein X is an alkylene, cycloalkylene, arylene, alkarylene, cycloalkarylene, aralkylene, heterocyclylene or a combination thereof.

46. The coating of claim 45, wherein the curing occurs in the presence of an initiator.

47. The coating of claim 45 further comprising an additive.

48. The coating of claim 47, wherein the additive is a filler, rheology modifier, thickener, surfactant, wetting agent, crosslinking agent, coupling agent, colorant, lubricant, leveling agent, antioxidant, UV stabilizer, plasticizer or a combination thereof.

49. A coating comprising a resin prepared by curing Formula (B), (E) or a combination thereof:

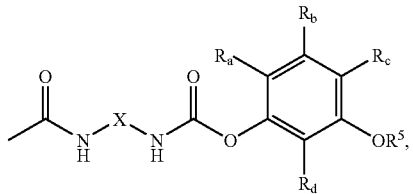

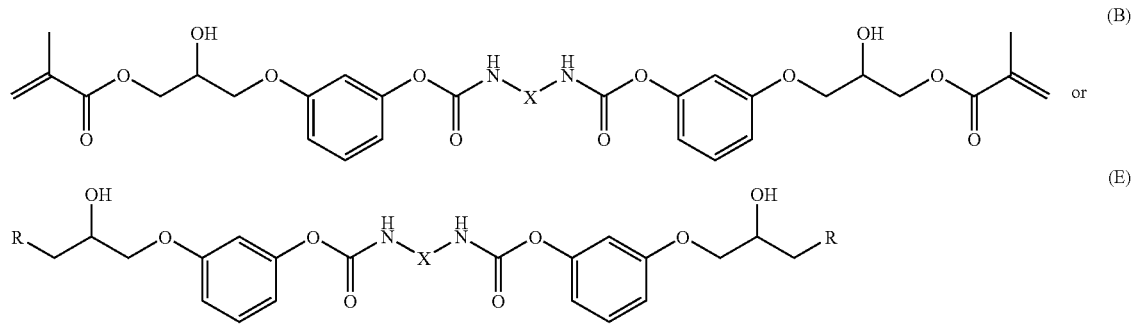

with a diisocyante, a polyisocyanate or a combination thereof, wherein X is an alkylene, cycloalkylene, arylene, alkarylene, cycloalkarylene, aralkylene, heterocyclylene or a combination thereof; and R is alkyl, aryl, aralkyl, siloxanyl, silyl ether or a combination thereof.

50. The coating of claim 49 further comprising an additive.

51. The coating of claim 50, wherein the additive is a filler, rheology modifier, thickener, surfactant, wetting agent, crosslinking agent, coupling agent, colorant, lubricant, leveling agent, antioxidant, UV stabilizer, plasticizer or a combination thereof.

52. A resorcinol-blocked isocyanate composition comprising a compound having Formula (IIC):

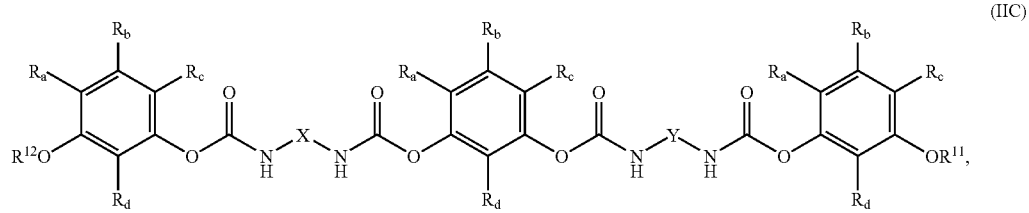

wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acyl, alkyl, aryl, aralkyl, or alkaryl; and each of $R^{11}$ and $R^{12}$ is independently H, acyl, alkyl, alkenyl, Formula (IV) or Formula (V):

-continued

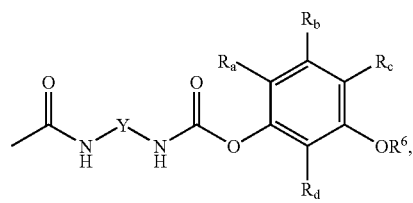

wherein each of $R^5$ and $R^6$ is independently H, acyl, alkyl or alkenyl.

53. The resorcinol-blocked isocyanate composition of claim 52, wherein the resorcinol-blocked isocyanate composition has at least two melting temperatures.

54. The resorcinol-blocked isocyanate composition of claim 52, wherein the resorcinol-blocked isocyanate composition has at least two unblocking temperatures.

55. The resorcinol-blocked isocyanate composition of claim 52 further comprising Formula (IIA), Formula (IIIA), Formula (IIB), Formula (IIIB):

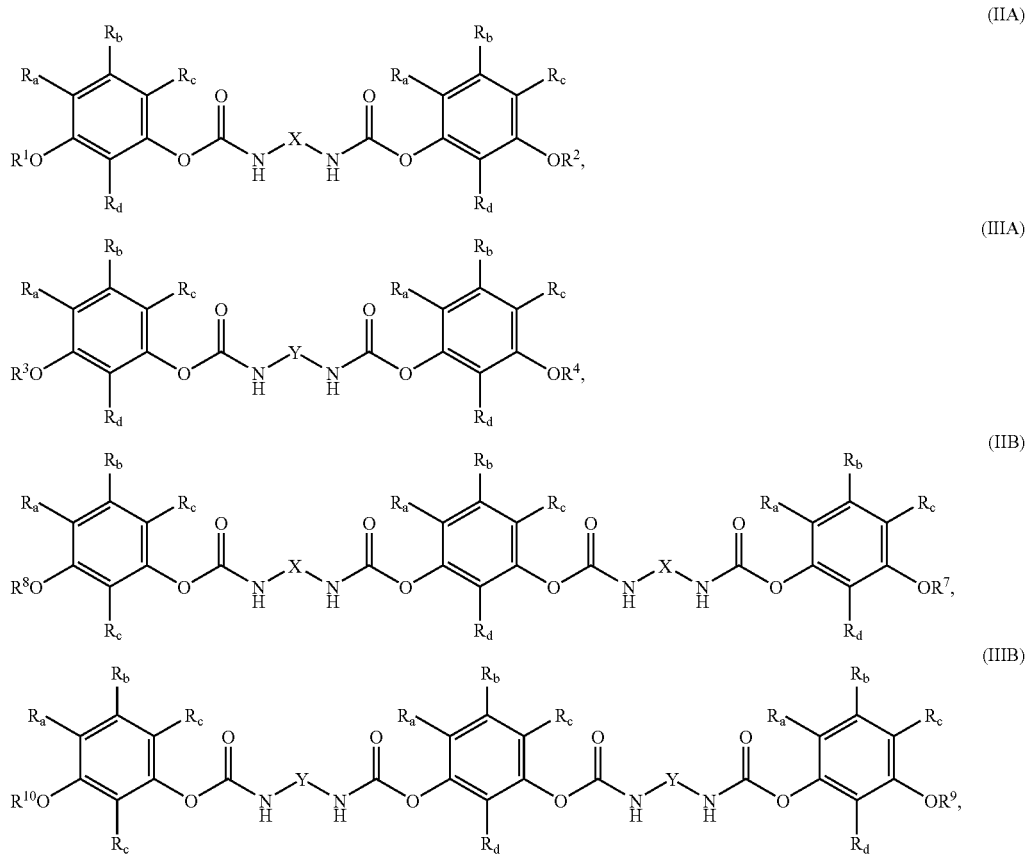

or a combination thereof; wherein X and Y are different and each of X and Y is independently alkylene, cycloalkylene, arylene, alkarylene, cycloalkarylene, aralkylene, heterocyclylene, heteroarylene or a combination thereof; each of $R_a$, $R_b$, $R_c$ and $R_d$ is independently hydrogen, hydroxyl, halide, nitro, benzo, carboxy, acyl, alkyl, aryl, aralkyl, or alkaryl; and each of $R^1$, $R^2$, $R^3$, $R^4$, $R^7$, $R^8$, $R^9$ and $R^{10}$ is independently H, acyl, alkyl, alkenyl, Formula (IV) or Formula (V).

56. The resorcinol-blocked isocyanate composition of claim 55, wherein the resorcinol-blocked isocyanate composition comprises Formula (IIC), Formula (IIA) and Formula (IIIA).

57. The resorcinol-blocked isocyanate composition of claim 56, wherein each of $R^{11}$, $R^{12}$, $R_a$, $R_b$, $R_c$ and $R_d$ is hydrogen.

58. The resorcinol-blocked isocyanate composition of claim 57, wherein X is a divalent radical having Formula (C) and Y is a divalent radical having Formula (D):

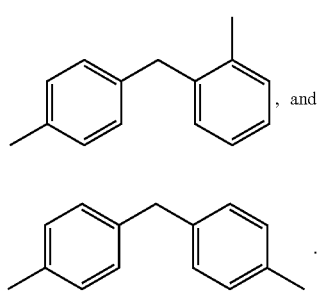

* * * * *

UNITED STATES PATENT AND TRADEMARK OFFICE
CERTIFICATE OF CORRECTION

PATENT NO. : 7,705,088 B2  Page 1 of 1
APPLICATION NO. : 11/564686
DATED : April 27, 2010
INVENTOR(S) : Durairaj et al.

It is certified that error appears in the above-identified patent and that said Letters Patent is hereby corrected as shown below:

In column 75, line 1, insert --

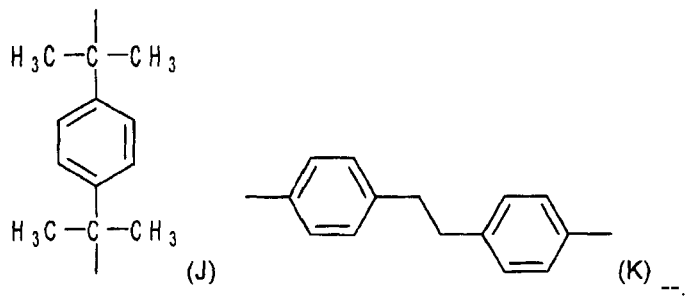

In column 93, delete the IIB and IIIB formulas and insert

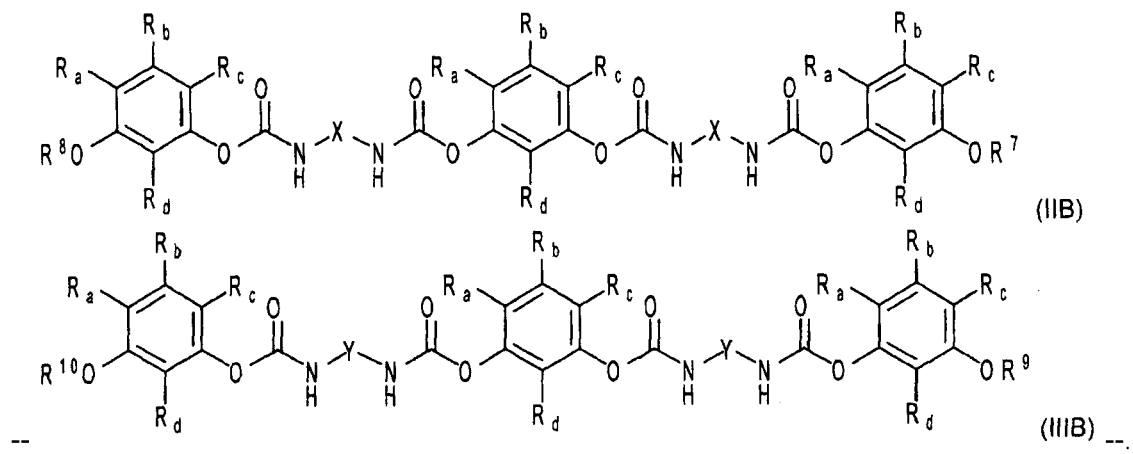

--

Signed and Sealed this

Thirty-first Day of August, 2010

David J. Kappos
*Director of the United States Patent and Trademark Office*